US011857599B2

(12) United States Patent
Kumar et al.

(10) Patent No.: US 11,857,599 B2
(45) Date of Patent: *Jan. 2, 2024

(54) COMPOSITIONS AND METHODS FOR TREATING SPINAL MUSCULAR ATROPHY

(71) Applicant: Acceleron Pharma Inc., Cambridge, MA (US)

(72) Inventors: Ravindra Kumar, Acton, MA (US); Rajasekhar Naga Venkata Sai Suragani, Wrentham, MA (US); Jia Li, Danvers, MA (US)

(73) Assignee: Acceleron Pharma Inc., Rahway, NJ (US)

( * ) Notice: Subject to any disclaimer, the term of this patent is extended or adjusted under 35 U.S.C. 154(b) by 322 days.

This patent is subject to a terminal disclaimer.

(21) Appl. No.: 16/499,098

(22) PCT Filed: Apr. 2, 2018

(86) PCT No.: PCT/US2018/025689

§ 371 (c)(1),
(2) Date: Sep. 27, 2019

(87) PCT Pub. No.: WO2018/187209

PCT Pub. Date: Oct. 11, 2018

(65) Prior Publication Data

US 2022/0088142 A1 Mar. 24, 2022

Related U.S. Application Data

(60) Provisional application No. 62/480,835, filed on Apr. 3, 2017.

(51) Int. Cl.

| | |
|---|---|
| ***A61K 38/18*** | (2006.01) |
| ***A61K 38/17*** | (2006.01) |
| ***A61P 21/00*** | (2006.01) |
| ***A61K 31/7125*** | (2006.01) |
| ***A61K 45/06*** | (2006.01) |
| ***C07K 14/71*** | (2006.01) |
| ***C12N 15/113*** | (2010.01) |

(52) U.S. Cl.

CPC ...... *A61K 38/1841* (2013.01); *A61K 31/7125* (2013.01); *A61K 38/18* (2013.01); *A61K 45/06* (2013.01); *A61P 21/00* (2018.01); *C07K 14/71* (2013.01); *C12N 15/113* (2013.01); *A61K 38/179* (2013.01); *C07K 2319/30* (2013.01); *C07K 2319/32* (2013.01); *C12N 2310/11* (2013.01); *C12N 2320/31* (2013.01)

(58) Field of Classification Search

None

See application file for complete search history.

(56) References Cited

U.S. PATENT DOCUMENTS

| | | | | |
|---|---|---|---|---|
| 5,288,931 A * | 2/1994 | Chang | C07K 1/1133 530/825 |
| 7,112,660 B1 * | 9/2006 | Domingues | A61P 37/08 424/85.2 |
| 10,738,098 B2 * | 8/2020 | Kumar | A61P 1/04 |
| 2003/0045474 A1 * | 3/2003 | Sailer | A61K 38/1875 514/8.8 |
| 2014/0154743 A1 * | 6/2014 | Levy | C07K 16/00 435/69.6 |

FOREIGN PATENT DOCUMENTS

| | | | |
|---|---|---|---|
| WO | WO-2012024242 A1 | | 2/2012 |
| WO | WO 2016/164497 A1 | * | 10/2016 |
| WO | WO-2016164497 A1 | | 10/2016 |
| WO | WO-2017218592 A1 | | 12/2017 |

OTHER PUBLICATIONS

Tokuriki et al., 2009, Curr. Opin. Struc. Biol. 19:596-604).*
Bhattacharya et al. (2017, PLoS ONE 12(3): e0171355, https://doi.org/10.1371/journal.pone.0171355.*
Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837).*
Bernier et al. (2004, Curr. Opin. Pharmacol. 4:528-533).*
Liu et al. (Nov. 2016, PLoS ONE 11(11):e0166803, doi:10.137/journal.pone.0166803; pp. 1-17).*
De Sanctis et al. (2016, Neuromuscular Disorder 26(11):754-759).*
Van et al. (2016, Current Opinion in Neurology 29.5:549-556).*
De Sanctis et al., "Developmental Milestones in Type I Spinal Muscular Atrophy," Neuromuscular Disord, 26(11): 754-759 (2016).
International Search Report and Written Opinion for International Application No. PCT/US2018/025689 dated Jul. 5, 2018.
Liu et al., "Activin Receptor Type IIB Inhibition Improves Muscle Phenotype and Function in a Mouse Model of Spinal Muscular Atrophy," PLOS ONE, 11(11): 5-6 (2016).
Van Alstyne et al., "Advances in Modeling and Treating Spinal Muscular Atrophy," Curr Opin Neurol, 29(5): 549-556 (2016).

* cited by examiner

*Primary Examiner* — Elizabeth C. Kemmerer
(74) *Attorney, Agent, or Firm* — Sanjeev K. Mahanta; Alysia Finnegan

(57) ABSTRACT

In certain aspects, the disclosure provides compositions and methods for treating spinal muscular atrophy. For example, in some embodiments, the disclosure provides ALK4:ActRIIB antagonists that may be used to treat spinal muscular atrophy, particularly treating one or more complications of spinal muscular atrophy including, for example, increasing muscle mass muscle strength, and bone mineral density.

30 Claims, 10 Drawing Sheets

Specification includes a Sequence Listing.

```
ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

           IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

           EVTQPTSNPV TPKPPT
           GGPEVTYEPP PTAPT
```

FIGURE 1

```
IgG1   -------THTCPPCPAPELLGGPSVFLFPPKPKDTLMISRTPEVTCVVVDVSHEDPEVKF 53
IgG4   ---ESKYGPPCPSCPAPEFLGGPSVFLFPPKPKDTLMISRTPEVTCVVVDVSQEDPEVQF 57
IgG2   --------VECPPCPAPPVAG-PSVFLFPPKPKDTLMISRTPEVTCVVVDVSHEDPEVQF 51
IgG3   EPKSCDTPPPCPRCPAPELLGGPSVFLFPPKPKDTLMISRTPEVTCVVVDVSHEDPEVQF 60
                 ** ****  . * ******************************:*****:*

IgG1   NWYVDGVEVHNAKTKPREEQYNSTYRVVSVLTVLHQDWLNGKEYKCKVSNKALPAPIEKT 113
IgG4   NWYVDGVEVHNAKTKPREEQFNSTYRVVSVLTVLHQDWLNGKEYKCKVSNKGLPSSIEKT 117
IgG2   NWYVDGVEVHNAKTKPREEQFNSTFRVVSVLTVVHQDWLNGKEYKCKVSNKGLPAPIEKT 111
IgG3   KWYVDGVEVHNAKTKPREEQYNSTFRVVSVLTVLHQDWLNGKEYKCKVSNKALPAPIEKT 120
       :*******************:***:********:*****************.**:.****

IgG1   ISKAKGQPREPQVYTLPPSREEMTKNQVSLTCLVKGFYPSDIAVEWESNGQPENNYKTTP 173
IgG4   ISKAKGQPREPQVYTLPPSQEEMTKNQVSLTCLVKGFYPSDIAVEWESNGQPENNYKTTP 177
IgG2   ISKTKGQPREPQVYTLPPSREEMTKNQVSLTCLVKGFYPSDIAVEWESNGQPENNYKTTP 171
IgG3   ISKTKGQPREPQVYTLPPSREEMTKNQVSLTCLVKGFYPSDIAVEWESSGQPENNYNTTP 180
       ***:***************:****************************.*******:***

IgG1   PVLDSDGSFFLYSKLTVDKSRWQQGNVFSCSVMHEALHNHYTQKSLSLSPGK 225
IgG4   PVLDSDGSFFLYSRLTVDKSRWQEGNVFSCSVMHEALHNHYTQKSLSLSLGK 229
IgG2   PMLDSDGSFFLYSKLTVDKSRWQQGNVFSCSVMHEALHNHYTQKSLSLSPGK 223
IgG3   PMLDSDGSFFLYSKLTVDKSRWQQGNIFSCSVMHEALHNRFTQKSLSLSPGK 232
       *:***********:*********:**:************::******** **
```

FIGURE 3

SEQUENCE LISTING

```
<160> NUMBER OF SEQ ID NOS: 91

<210> SEQ ID NO 1
<211> LENGTH: 512
<212> TYPE: PRT
<213> ORGANISM: Homo sapiens

<400> SEQUENCE: 1

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
```

```
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510


<210> SEQ ID NO 2
<211> LENGTH: 115
<212> TYPE: PRT
<213> ORGANISM: Homo sapiens

<400> SEQUENCE: 2

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45
```

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 3
<211> LENGTH: 100
<212> TYPE: PRT
<213> ORGANISM: Homo sapiens

<400> SEQUENCE: 3

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100

<210> SEQ ID NO 4
<211> LENGTH: 512
<212> TYPE: PRT
<213> ORGANISM: Homo sapiens

<400> SEQUENCE: 4

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

-continued

```
Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510
```

<210> SEQ ID NO 5
<211> LENGTH: 115
<212> TYPE: PRT
<213> ORGANISM: Homo sapiens

<400> SEQUENCE: 5

```
Gly Arg Gly Glu Ala Glu Thr Arg Glu Cys Ile Tyr Tyr Asn Ala Asn
1               5                   10                  15
```

```
Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115


<210> SEQ ID NO 6
<211> LENGTH: 100
<212> TYPE: PRT
<213> ORGANISM: Homo sapiens

<400> SEQUENCE: 6

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100


<210> SEQ ID NO 7
<211> LENGTH: 1536
<212> TYPE: DNA
<213> ORGANISM: Homo sapiens

<400> SEQUENCE: 7

atgacggcgc cctgggtggc cctcgccctc ctctggggat cgctgtgcgc cggctctggg      60

cgtggggagg ctgagacacg ggagtgcatc tactacaacg ccaactggga gctggagcgc     120

accaaccaga gcggcctgga gcgctgcgaa ggcgagcagg acaagcggct gcactgctac     180

gcctcctggc gcaacagctc tggcaccatc gagctcgtga agaagggctg ctggctagat     240

gacttcaact gctacgatag gcaggagtgt gtggccactg aggagaaccc ccaggtgtac     300

ttctgctgct gtgaaggcaa cttctgcaac gaacgcttca ctcatttgcc agaggctggg     360

ggcccggaag tcacgtacga gccacccccg acagccccca ccctgctcac ggtgctggcc     420

tactcactgc tgcccatcgg gggcctttcc ctcatcgtcc tgctggcctt ttggatgtac     480

cggcatcgca agcccccta cggtcatgtg gacatccatg aggaccctgg gcctccacca     540

ccatcccctc tggtgggcct gaagccactg cagctgctgg agatcaaggc tcgggggcgc     600
```

-continued

```
tttggctgtg tctggaaggc ccagctcatg aatgactttg tagctgtcaa gatcttccca     660

ctccaggaca agcagtcgtg gcagagtgaa cgggagatct tcagcacacc tggcatgaag     720

cacgagaacc tgctacagtt cattgctgcc gagaagcgag gctccaacct cgaagtagag     780

ctgtggctca tcacggcctt ccatgacaag ggctccctca cggattacct caaggggaac     840

atcatcacat ggaacgaact gtgtcatgta gcagagacga tgtcacgagg cctctcatac     900

ctgcatgagg atgtgccctg gtgccgtggc gagggccaca agccgtctat tgcccacagg     960

gactttaaaa gtaagaatgt attgctgaag agcgacctca cagccgtgct ggctgacttt    1020

ggcttggctg ttcgatttga gccagggaaa cctccagggg acacccacgg acaggtaggc    1080

acgagacggt acatggctcc tgaggtgctc gagggagcca tcaacttcca gagagatgcc    1140

ttcctgcgca ttgacatgta tgccatgggg ttggtgctgt gggagcttgt gtctcgctgc    1200

aaggctgcag acggacccgt ggatgagtac atgctgccct ttgaggaaga gattggccag    1260

caccccttcgt tggaggagct gcaggaggtg gtggtgcaca agaagatgag gcccaccatt    1320

aaagatcact ggttgaaaca cccgggcctg gcccagcttt gtgtgaccat cgaggagtgc    1380

tgggaccatg atgcagaggc tcgcttgtcc gcgggctgtg tggaggagcg ggtgtccctg    1440

attcggaggt cggtcaacgg cactacctcg gactgtctcg tttccctggt gacctctgtc    1500

accaatgtgg acctgccccc taaagagtca agcatc                              1536
```

<210> SEQ ID NO 8
<211> LENGTH: 345
<212> TYPE: DNA
<213> ORGANISM: Homo sapiens

<400> SEQUENCE: 8

```
gggcgtgggg aggctgagac acgggagtgc atctactaca acgccaactg ggagctggag      60

cgcaccaacc agagcggcct ggagcgctgc gaaggcgagc aggacaagcg gctgcactgc     120

tacgcctcct ggcgcaacag ctctggcacc atcgagctcg tgaagaaggg ctgctggcta     180

gatgacttca actgctacga taggcaggag tgtgtggcca ctgaggagaa cccccaggtg     240

tacttctgct gctgtgaagg caacttctgc aacgaacgct tcactcattt gccagaggct     300

gggggcccgg aagtcacgta cgagccaccc ccgacagccc ccacc                    345
```

<210> SEQ ID NO 9
<211> LENGTH: 505
<212> TYPE: PRT
<213> ORGANISM: Homo sapiens

<400> SEQUENCE: 9

```
Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
```

```
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285

Ser Leu Phe Asp Tyr Leu Asn Arg Tyr Thr Val Thr Ile Glu Gly Met
    290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
        355                 360                 365

Ile Ala Pro Asn Gln Arg Val Gly Thr Lys Arg Tyr Met Ala Pro Glu
    370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
                405                 410                 415

Cys Asn Ser Gly Gly Val His Glu Glu Tyr Gln Leu Pro Tyr Tyr Asp
            420                 425                 430

Leu Val Pro Ser Asp Pro Ser Ile Glu Glu Met Arg Lys Val Val Cys
        435                 440                 445

Asp Gln Lys Leu Arg Pro Asn Ile Pro Asn Trp Trp Gln Ser Tyr Glu
    450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
            500                 505

<210> SEQ ID NO 10
```

<211> LENGTH: 103
<212> TYPE: PRT
<213> ORGANISM: Homo sapiens

<400> SEQUENCE: 10

```
Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100
```

<210> SEQ ID NO 11
<211> LENGTH: 1515
<212> TYPE: DNA
<213> ORGANISM: Homo sapiens

<400> SEQUENCE: 11

```
atggcggagt cggccggagc ctcctccttc ttccccccttg ttgtcctcct gctcgccggc      60

agcggcgggt ccgggccccg gggggtccag gctctgctgt gtgcgtgcac cagctgcctc     120

caggccaact acacgtgtga gacagatggg gcctgcatgg tttccatttt caatctggat     180

gggatggagc accatgtgcg cacctgcatc cccaaagtgg agctggtccc tgccgggaag     240

cccttctact gcctgagctc ggaggacctg cgcaacaccc actgctgcta cactgactac     300

tgcaacagga tcgacttgag ggtgcccagt ggtcacctca aggagcctga gcacccgtcc     360

atgtggggcc cggtggagct ggtaggcatc atcgccggcc cggtgttcct cctgttcctc     420

atcatcatca ttgttttcct tgtcattaac tatcatcagc gtgtctatca caaccgccag     480

agactggaca tggaagatcc ctcatgtgag atgtgtctct ccaaagacaa gacgctccag     540

gatcttgtct acgatctctc cacctcaggg tctggctcag ggttacccct ctttgtccag     600

cgcacagtgg cccgaaccat cgttttacaa gagattattg gcaagggtcg gtttggggaa     660

gtatggcggg gccgctggag gggtggtgat gtggctgtga aaatattctc ttctcgtgaa     720

gaacggtctt ggttcaggga agcagagata taccagacgg tcatgctgcg ccatgaaaac     780

atccttggat ttattgctgc tgacaataaa gataatggca cctggacaca gctgtggctt     840

gtttctgact atcatgagca cgggtccctg tttgattatc tgaaccggta cacagtgaca     900

attgagggga tgattaagct ggccttgtct gctgctagtg ggctggcaca cctgcacatg     960

gagatcgtgg gcacccaagg gaagcctgga attgctcatc gagacttaaa gtcaaagaac    1020

attctggtga agaaaaatgg catgtgtgcc atagcagacc tgggcctggc tgtccgtcat    1080

gatgcagtca ctgacaccat tgacattgcc ccgaatcaga gggtggggac caaacgatac    1140

atggcccctg aagtacttga tgaaaccatt aatatgaaac actttgactc ctttaaatgt    1200

gctgatattt atgccctcgg gcttgtatat tgggagattg ctcgaagatg caattctgga    1260

ggagtccatg aagaatatca gctgccatat tacgacttag tgccctctga cccttccatt    1320
```

gaggaaatgc gaaaggttgt atgtgatcag aagctgcgtc ccaacatccc caactggtgg 1380
cagagttatg aggcactgcg ggtgatgggg aagatgatgc gagagtgttg gtatgccaac 1440
ggcgcagccc gcctgacggc cctgcgcatc aagaagaccc tctcccagct cagcgtgcag 1500
gaagacgtga agatc 1515

<210> SEQ ID NO 12
<211> LENGTH: 309
<212> TYPE: DNA
<213> ORGANISM: Homo sapiens

<400> SEQUENCE: 12
tccgggcccc ggggggtcca ggctctgctg tgtgcgtgca ccagctgcct ccaggccaac 60
tacacgtgtg agacagatgg ggcctgcatg gtttccattt tcaatctgga tgggatggag 120
caccatgtgc gcacctgcat ccccaaagtg gagctggtcc ctgccgggaa gcccttctac 180
tgcctgagct cggaggacct gcgcaacacc cactgctgct acactgacta ctgcaacagg 240
atcgacttga gggtgcccag tggtcacctc aaggagcctg agcacccgtc catgtggggc 300
ccggtggag 309

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Gly Gly Gly
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Gly Gly Gly Gly
1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Thr Gly Gly Gly Gly
1 5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Ser Gly Gly Gly Gly
1 5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Thr Gly Gly Gly
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Ser Gly Gly Gly
1

<210> SEQ ID NO 19
<211> LENGTH: 546
<212> TYPE: PRT
<213> ORGANISM: Homo sapiens

<400> SEQUENCE: 19

Met Ala Glu Ser Ala Gly Ala Ser Ser Phe Phe Pro Leu Val Val Leu
1 5 10 15

Leu Leu Ala Gly Ser Gly Gly Ser Gly Pro Arg Gly Val Gln Ala Leu
20 25 30

Leu Cys Ala Cys Thr Ser Cys Leu Gln Ala Asn Tyr Thr Cys Glu Thr
35 40 45

Asp Gly Ala Cys Met Val Ser Ile Phe Asn Leu Asp Gly Met Glu His
50 55 60

His Val Arg Thr Cys Ile Pro Lys Val Glu Leu Val Pro Ala Gly Lys
65 70 75 80

Pro Phe Tyr Cys Leu Ser Ser Glu Asp Leu Arg Asn Thr His Cys Cys
85 90 95

Tyr Thr Asp Tyr Cys Asn Arg Ile Asp Leu Arg Val Pro Ser Gly His
100 105 110

Leu Lys Glu Pro Glu His Pro Ser Met Trp Gly Pro Val Glu Leu Val
115 120 125

Gly Ile Ile Ala Gly Pro Val Phe Leu Leu Phe Leu Ile Ile Ile Ile
130 135 140

Val Phe Leu Val Ile Asn Tyr His Gln Arg Val Tyr His Asn Arg Gln
145 150 155 160

Arg Leu Asp Met Glu Asp Pro Ser Cys Glu Met Cys Leu Ser Lys Asp
165 170 175

Lys Thr Leu Gln Asp Leu Val Tyr Asp Leu Ser Thr Ser Gly Ser Gly
180 185 190

Ser Gly Leu Pro Leu Phe Val Gln Arg Thr Val Ala Arg Thr Ile Val
195 200 205

```
Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Ala Asp
            260                 265                 270

Cys Ser Phe Leu Thr Leu Pro Trp Glu Val Val Met Val Ser Ala Ala
        275                 280                 285

Pro Lys Leu Arg Ser Leu Arg Leu Gln Tyr Lys Gly Gly Arg Gly Arg
    290                 295                 300

Ala Arg Phe Leu Phe Pro Leu Asn Asn Gly Thr Trp Thr Gln Leu Trp
305                 310                 315                 320

Leu Val Ser Asp Tyr His Glu His Gly Ser Leu Phe Asp Tyr Leu Asn
                325                 330                 335

Arg Tyr Thr Val Thr Ile Glu Gly Met Ile Lys Leu Ala Leu Ser Ala
            340                 345                 350

Ala Ser Gly Leu Ala His Leu His Met Glu Ile Val Gly Thr Gln Gly
        355                 360                 365

Lys Pro Gly Ile Ala His Arg Asp Leu Lys Ser Lys Asn Ile Leu Val
    370                 375                 380

Lys Lys Asn Gly Met Cys Ala Ile Ala Asp Leu Gly Leu Ala Val Arg
385                 390                 395                 400

His Asp Ala Val Thr Asp Thr Ile Asp Ile Ala Pro Asn Gln Arg Val
                405                 410                 415

Gly Thr Lys Arg Tyr Met Ala Pro Glu Val Leu Asp Glu Thr Ile Asn
            420                 425                 430

Met Lys His Phe Asp Ser Phe Lys Cys Ala Asp Ile Tyr Ala Leu Gly
        435                 440                 445

Leu Val Tyr Trp Glu Ile Ala Arg Arg Cys Asn Ser Gly Gly Val His
    450                 455                 460

Glu Glu Tyr Gln Leu Pro Tyr Tyr Asp Leu Val Pro Ser Asp Pro Ser
465                 470                 475                 480

Ile Glu Glu Met Arg Lys Val Val Cys Asp Gln Lys Leu Arg Pro Asn
                485                 490                 495

Ile Pro Asn Trp Trp Gln Ser Tyr Glu Ala Leu Arg Val Met Gly Lys
            500                 505                 510

Met Met Arg Glu Cys Trp Tyr Ala Asn Gly Ala Ala Arg Leu Thr Ala
        515                 520                 525

Leu Arg Ile Lys Lys Thr Leu Ser Gln Leu Ser Val Gln Glu Asp Val
    530                 535                 540

Lys Ile
545
```

<210> SEQ ID NO 20
<211> LENGTH: 103
<212> TYPE: PRT
<213> ORGANISM: Homo sapiens

<400> SEQUENCE: 20

```
Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
```

-continued

```
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100


<210> SEQ ID NO 21
<211> LENGTH: 1638
<212> TYPE: DNA
<213> ORGANISM: Homo sapiens

<400> SEQUENCE: 21

atggcggagt cggccggagc ctcctccttc ttccccccttg ttgtcctcct gctcgccggc     60

agcggcgggt ccgggccccg gggggtccag gctctgctgt gtgcgtgcac cagctgcctc    120

caggccaact acacgtgtga gacagatggg gcctgcatgg tttccatttt caatctggat    180

gggatggagc accatgtgcg cacctgcatc cccaaagtgg agctggtccc tgccgggaag    240

cccttctact gcctgagctc ggaggacctg cgcaacaccc actgctgcta cactgactac    300

tgcaacagga tcgacttgag ggtgcccagt ggtcacctca aggagcctga gcacccgtcc    360

atgtggggcc cggtggagct ggtaggcatc atcgccggcc cggtgttcct cctgttcctc    420

atcatcatca ttgttttcct tgtcattaac tatcatcagc gtgtctatca caaccgccag    480

agactggaca tggaagatcc ctcatgtgag atgtgtctct ccaaagacaa gacgctccag    540

gatcttgtct acgatctctc cacctcaggg tctggctcag ggttacccct ctttgtccag    600

cgcacagtgg cccgaaccat cgttttacaa gagattattg gcaagggtcg gtttggggaa    660

gtatggcggg gccgctggag gggtggtgat gtggctgtga aaatattctc ttctcgtgaa    720

gaacggtctt ggttcaggga agcagagata taccagacgg tcatgctgcg ccatgaaaac    780

atccttggat ttattgctgc tgacaataaa gcagactgct cattcctcac attgccatgg    840

gaagttgtaa tggtctctgc tgcccccaag ctgaggagcc ttagactcca atacaaggga    900

ggaaggggaa gagcaagatt tttattccca ctgaataatg gcacctggac acagctgtgg    960

cttgtttctg actatcatga gcacgggtcc ctgtttgatt atctgaaccg gtacacagtg   1020

acaattgagg ggatgattaa gctggccttg tctgctgcta gtgggctggc acacctgcac   1080

atggagatcg tgggcaccca agggaagcct ggaattgctc atcgagactt aaagtcaaag   1140

aacattctgg tgaagaaaaa tggcatgtgt gccatagcag acctgggcct ggctgtccgt   1200

catgatgcag tcactgacac cattgacatt gccccgaatc agagggtggg gaccaaacga   1260

tacatggccc ctgaagtact tgatgaaacc attaatatga aacactttga ctcctttaaa   1320

tgtgctgata tttatgccct cgggcttgta tattgggaga ttgctcgaag atgcaattct   1380

ggaggagtcc atgaagaata tcagctgcca tattacgact tagtgccctc tgacccttcc   1440

attgaggaaa tgcgaaaggt tgtatgtgat cagaagctgc gtcccaacat ccccaactgg   1500

tggcagagtt atgaggcact gcgggtgatg gggaagatga tgcgagagtg ttggtatgcc   1560

aacggcgcag cccgcctgac ggccctgcgc atcaagaaga ccctctccca gctcagcgtg   1620
```

caggaagacg tgaagatc 1638

<210> SEQ ID NO 22
<211> LENGTH: 309
<212> TYPE: DNA
<213> ORGANISM: Homo sapiens

<400> SEQUENCE: 22
tccgggcccc ggggggtcca ggctctgctg tgtgcgtgca ccagctgcct ccaggccaac 60
tacacgtgtg agacagatgg ggcctgcatg gtttccattt tcaatctgga tgggatggag 120
caccatgtgc gcacctgcat ccccaaagtg gagctggtcc ctgccgggaa gcccttctac 180
tgcctgagct cggaggacct gcgcaacacc cactgctgct acactgacta ctgcaacagg 240
atcgacttga gggtgcccag tggtcacctc aaggagcctg agcacccgtc catgtggggc 300
ccggtggag 309

<210> SEQ ID NO 23
<211> LENGTH: 225
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 23

Thr His Thr Cys Pro Pro Cys Pro Ala Pro Glu Leu Leu Gly Gly Pro
1 5 10 15

Ser Val Phe Leu Phe Pro Pro Lys Pro Lys Asp Thr Leu Met Ile Ser
20 25 30

Arg Thr Pro Glu Val Thr Cys Val Val Val Asp Val Ser His Glu Asp
35 40 45

Pro Glu Val Lys Phe Asn Trp Tyr Val Asp Gly Val Glu Val His Asn
50 55 60

Ala Lys Thr Lys Pro Arg Glu Glu Gln Tyr Asn Ser Thr Tyr Arg Val
65 70 75 80

Val Ser Val Leu Thr Val Leu His Gln Asp Trp Leu Asn Gly Lys Glu
85 90 95

Tyr Lys Cys Lys Val Ser Asn Lys Ala Leu Pro Ala Pro Ile Glu Lys
100 105 110

Thr Ile Ser Lys Ala Lys Gly Gln Pro Arg Glu Pro Gln Val Tyr Thr
115 120 125

Leu Pro Pro Ser Arg Lys Glu Met Thr Lys Asn Gln Val Ser Leu Thr
130 135 140

Cys Leu Val Lys Gly Phe Tyr Pro Ser Asp Ile Ala Val Glu Trp Glu
145 150 155 160

Ser Asn Gly Gln Pro Glu Asn Asn Tyr Lys Thr Thr Pro Pro Val Leu
165 170 175

Lys Ser Asp Gly Ser Phe Phe Leu Tyr Ser Lys Leu Thr Val Asp Lys
180 185 190

Ser Arg Trp Gln Gln Gly Asn Val Phe Ser Cys Ser Val Met His Glu
195 200 205

Ala Leu His Asn His Tyr Thr Gln Lys Ser Leu Ser Leu Ser Pro Gly
210 215 220

Lys
225

<210> SEQ ID NO 24
<211> LENGTH: 225
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 24

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Asp Thr Thr Pro Pro Val Leu
                165                 170                 175

Asp Ser Asp Gly Ser Phe Phe Leu Tyr Ser Asp Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 25
<211> LENGTH: 225
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
```

-continued

```
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Tyr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225


<210> SEQ ID NO 26
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Thr Ser Lys Leu Thr Val Asp Lys
            180                 185                 190
```

-continued

```
Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225


<210> SEQ ID NO 27
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Glu Glu Met Thr Lys Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225


<210> SEQ ID NO 28
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Thr His Thr Cys Pro Pro Cys Pro Ala Pro Glu Leu Leu Gly Gly Pro
1               5                   10                  15
```

-continued

```
Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
        115                 120                 125

Leu Pro Pro Ser Arg Glu Glu Met Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225


<210> SEQ ID NO 29
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Phe Arg Pro Glu Val His Leu
        115                 120                 125

Leu Pro Pro Ser Arg Glu Glu Met Thr Lys Asn Gln Val Ser Leu Thr
    130                 135                 140
```

```
Cys Leu Ala Arg Gly Phe Tyr Pro Lys Asp Ile Ala Val Glu Trp Glu
145                 150                 155                 160

Ser Asn Gly Gln Pro Glu Asn Asn Tyr Lys Thr Thr Pro Ser Arg Gln
                165                 170                 175

Glu Pro Ser Gln Gly Thr Thr Thr Phe Ala Val Thr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Thr Ile Ser Leu
    210                 215                 220

Ser Pro Gly Lys
225


<210> SEQ ID NO 30
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Pro Ser Glu Glu Leu Ala Leu Asn Glu Leu Val Thr Leu
    130                 135                 140

Thr Cys Leu Val Lys Gly Phe Tyr Pro Ser Asp Ile Ala Val Glu Trp
145                 150                 155                 160

Glu Ser Asn Gly Gln Glu Leu Pro Arg Glu Lys Tyr Leu Thr Trp Ala
                165                 170                 175

Pro Val Leu Asp Ser Asp Gly Ser Phe Phe Leu Tyr Ser Ile Leu Arg
            180                 185                 190

Val Ala Ala Glu Asp Trp Lys Lys Gly Asp Thr Phe Ser Cys Ser Val
        195                 200                 205

Met His Glu Ala Leu His Asn His Tyr Thr Gln Lys Ser Leu Asp Arg
    210                 215                 220

Ser Pro Gly Lys
225


<210> SEQ ID NO 31
<211> LENGTH: 225
<212> TYPE: PRT
```

<213> ORGANISM: Homo sapiens

<400> SEQUENCE: 31

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 32
<211> LENGTH: 223
<212> TYPE: PRT
<213> ORGANISM: Homo sapiens

<400> SEQUENCE: 32

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro

-continued

```
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220


<210> SEQ ID NO 33
<211> LENGTH: 232
<212> TYPE: PRT
<213> ORGANISM: Homo sapiens

<400> SEQUENCE: 33

Glu Pro Lys Ser Cys Asp Thr Pro Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Lys Trp Tyr Val
    50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
    210                 215                 220

Ser Leu Ser Leu Ser Pro Gly Lys
225                 230


<210> SEQ ID NO 34
<211> LENGTH: 279
<212> TYPE: PRT
<213> ORGANISM: Homo sapiens
```

<400> SEQUENCE: 34

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275
```

<210> SEQ ID NO 35
<211> LENGTH: 229
<212> TYPE: PRT
<213> ORGANISM: Homo sapiens

<400> SEQUENCE: 35

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80
```

-continued

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 36
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205
```

```
Ala Leu His Asn His Tyr Thr Gln Lys Ser Leu Ser Leu Ser Pro Gly
    210                 215                 220

Lys Gly Gly Ser Ala Gln Leu Glu Lys Glu Leu Gln Ala Leu Glu Lys
225                 230                 235                 240

Glu Asn Ala Gln Leu Glu Trp Glu Leu Gln Ala Leu Glu Lys Glu Leu
                245                 250                 255

Ala Gln Gly Ala Thr
            260


<210> SEQ ID NO 37
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Ser Ala Gln Leu Lys Lys Lys Leu Gln Ala Leu Lys Lys
225                 230                 235                 240

Lys Asn Ala Gln Leu Lys Trp Lys Leu Gln Ala Leu Lys Lys Lys Leu
                245                 250                 255

Ala Gln Gly Ala Thr
            260


<210> SEQ ID NO 38
<211> LENGTH: 22
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 38

Met Asp Ala Met Lys Arg Gly Leu Cys Cys Val Leu Leu Leu Cys Gly
1 5 10 15

Ala Val Phe Val Ser Pro
20

<210> SEQ ID NO 39
<211> LENGTH: 368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

Met Asp Ala Met Lys Arg Gly Leu Cys Cys Val Leu Leu Leu Cys Gly
1 5 10 15

Ala Val Phe Val Ser Pro Gly Ala Ser Gly Arg Gly Glu Ala Glu Thr
20 25 30

Arg Glu Cys Ile Tyr Tyr Asn Ala Asn Trp Glu Leu Glu Arg Thr Asn
35 40 45

Gln Ser Gly Leu Glu Arg Cys Glu Gly Glu Gln Asp Lys Arg Leu His
50 55 60

Cys Tyr Ala Ser Trp Arg Asn Ser Ser Gly Thr Ile Glu Leu Val Lys
65 70 75 80

Lys Gly Cys Trp Leu Asp Asp Phe Asn Cys Tyr Asp Arg Gln Glu Cys
85 90 95

Val Ala Thr Glu Glu Asn Pro Gln Val Tyr Phe Cys Cys Cys Glu Gly
100 105 110

Asn Phe Cys Asn Glu Arg Phe Thr His Leu Pro Glu Ala Gly Gly Pro
115 120 125

Glu Val Thr Tyr Glu Pro Pro Pro Thr Ala Pro Thr Gly Gly Gly Thr
130 135 140

His Thr Cys Pro Pro Cys Pro Ala Pro Glu Leu Leu Gly Gly Pro Ser
145 150 155 160

Val Phe Leu Phe Pro Pro Lys Pro Lys Asp Thr Leu Met Ile Ser Arg
165 170 175

Thr Pro Glu Val Thr Cys Val Val Val Asp Val Ser His Glu Asp Pro
180 185 190

Glu Val Lys Phe Asn Trp Tyr Val Asp Gly Val Glu Val His Asn Ala
195 200 205

Lys Thr Lys Pro Arg Glu Glu Gln Tyr Asn Ser Thr Tyr Arg Val Val
210 215 220

Ser Val Leu Thr Val Leu His Gln Asp Trp Leu Asn Gly Lys Glu Tyr
225 230 235 240

Lys Cys Lys Val Ser Asn Lys Ala Leu Pro Ala Pro Ile Glu Lys Thr
245 250 255

Ile Ser Lys Ala Lys Gly Gln Pro Arg Glu Pro Gln Val Tyr Thr Leu
260 265 270

Pro Pro Ser Arg Lys Glu Met Thr Lys Asn Gln Val Ser Leu Thr Cys
275 280 285

Leu Val Lys Gly Phe Tyr Pro Ser Asp Ile Ala Val Glu Trp Glu Ser

```
    290                 295                 300

Asn Gly Gln Pro Glu Asn Asn Tyr Lys Thr Thr Pro Pro Val Leu Lys
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365
```

<210> SEQ ID NO 40
<211> LENGTH: 1104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
atggatgcaa tgaagagagg gctctgctgt gtgctgctgc tgtgtggagc agtcttcgtt      60

tcgcccggcg cctctgggcg tggggaggct gagacacggg agtgcatcta ctacaacgcc     120

aactgggagc tggagcgcac caaccagagc ggcctggagc gctgcgaagg cgagcaggac     180

aagcggctgc actgctacgc ctcctggcgc aacagctctg gcaccatcga gctcgtgaag     240

aagggctgct ggctagatga cttcaactgc tacgataggc aggagtgtgt ggccactgag     300

gagaaccccc aggtgtactt ctgctgctgt gaaggcaact tctgcaacga gcgcttcact     360

catttgccag aggctggggg cccggaagtc acgtacgagc caccccccgac agcccccacc     420

ggtggtggaa ctcacacatg cccaccgtgc ccagcacctg aactcctggg gggaccgtca     480

gtcttcctct tccccccaaa acccaaggac accctcatga tctcccggac ccctgaggtc     540

acatgcgtgg tggtggacgt gagccacgaa gaccctgagg tcaagttcaa ctggtacgtg     600

gacggcgtgg aggtgcataa tgccaagaca aagccgcggg aggagcagta caacagcacg     660

taccgtgtgg tcagcgtcct caccgtcctg caccaggact ggctgaatgg caaggagtac     720

aagtgcaagg tctccaacaa agccctccca gcccccatcg agaaaaccat ctccaaagcc     780

aaagggcagc cccgagaacc acaggtgtac accctgcccc catcccggaa ggagatgacc     840

aagaaccagg tcagcctgac ctgcctggtc aaaggcttct atcccagcga catcgccgtg     900

gagtgggaga gcaatgggca gccggagaac aactacaaga ccacgcctcc cgtgctgaag     960

tccgacggct ccttcttcct ctatagcaag ctcaccgtgg acaagagcag gtggcagcag    1020

gggaacgtct tctcatgctc cgtgatgcat gaggctctgc acaaccacta cacgcagaag    1080

agcctctccc tgtctccggg taaa                                           1104
```

<210> SEQ ID NO 41
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30
```

```
Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Lys Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Lys Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340


<210> SEQ ID NO 42
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
```

```
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Asp Thr Thr Pro
    290                 295                 300

Pro Val Leu Asp Ser Asp Gly Ser Phe Phe Leu Tyr Ser Asp Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly
        355


<210> SEQ ID NO 43
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

atggatgcaa tgaagagagg gctctgctgt gtgctgctgc tgtgtggagc agtcttcgtt      60

tcgcccggcg cctccgggcc ccggggggtc caggctctgc tgtgtgcgtg caccagctgc     120

ctccaggcca actacacgtg tgagacagat ggggcctgca tggtttccat tttcaatctg     180
```

-continued

```
gatgggatgg agcaccatgt gcgcacctgc atccccaaag tggagctggt ccctgccggg    240

aagcccttct actgcctgag ctcggaggac ctgcgcaaca cccactgctg ctacactgac    300

tactgcaaca ggatcgactt gagggtgccc agtggtcacc tcaaggagcc tgagcacccg    360

tccatgtggg gcccggtgga gaccggtggt ggaactcaca catgcccacc gtgcccagca    420

cctgaactcc tggggggacc gtcagtcttc ctcttccccc caaaacccaa ggacaccctc    480

atgatctccc ggacccctga ggtcacatgc gtggtggtgg acgtgagcca cgaagaccct    540

gaggtcaagt tcaactggta cgtggacggc gtggaggtgc ataatgccaa gacaaagccg    600

cgggaggagc agtacaacag cacgtaccgt gtggtcagcg tcctcaccgt cctgcaccag    660

gactggctga atggcaagga gtacaagtgc aaggtctcca acaaagccct cccagccccc    720

atcgagaaaa ccatctccaa agccaaaggg cagccccgag aaccacaggt gtacaccctg    780

cccccatccc gggaggagat gaccaagaac caggtcagcc tgacctgcct ggtcaaaggc    840

ttctatccca gcgacatcgc cgtggagtgg gagagcaatg ggcagccgga gaacaactac    900

gacaccacgc ctcccgtgct ggactccgac ggctccttct tcctctatag cgacctcacc    960

gtggacaaga gcaggtggca gcaggggaac gtcttctcat gctccgtgat gcatgaggct   1020

ctgcacaacc actacacgca gaagagcctc tccctgtctc cgggt                   1065
```

```
<210> SEQ ID NO 44
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205
```

```
Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Asp Thr Thr Pro Pro Val Leu Asp Ser Asp Gly Ser
        275                 280                 285

Phe Phe Leu Tyr Ser Asp Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly
                325                 330


<210> SEQ ID NO 45
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
```

-continued 225 230 235 240

Lys Cys Lys Val Ser Asn Lys Ala Leu Pro Ala Pro Ile Glu Lys Thr
245 250 255

Ile Ser Lys Ala Lys Gly Gln Pro Arg Glu Pro Gln Val Tyr Thr Leu
260 265 270

Pro Pro Cys Arg Glu Glu Met Thr Lys Asn Gln Val Ser Leu Trp Cys
275 280 285

Leu Val Lys Gly Phe Tyr Pro Ser Asp Ile Ala Val Glu Trp Glu Ser
290 295 300

Asn Gly Gln Pro Glu Asn Asn Tyr Lys Thr Thr Pro Pro Val Leu Asp
305 310 315 320

Ser Asp Gly Ser Phe Phe Leu Tyr Ser Lys Leu Thr Val Asp Lys Ser
325 330 335

Arg Trp Gln Gln Gly Asn Val Phe Ser Cys Ser Val Met His Glu Ala
340 345 350

Leu His Asn His Tyr Thr Gln Lys Ser Leu Ser Leu Ser Pro Gly Lys
355 360 365

<210> SEQ ID NO 46
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Gly Arg Gly Glu Ala Glu Thr Arg Glu Cys Ile Tyr Tyr Asn Ala Asn
1 5 10 15

Trp Glu Leu Glu Arg Thr Asn Gln Ser Gly Leu Glu Arg Cys Glu Gly
20 25 30

Glu Gln Asp Lys Arg Leu His Cys Tyr Ala Ser Trp Arg Asn Ser Ser
35 40 45

Gly Thr Ile Glu Leu Val Lys Lys Gly Cys Trp Leu Asp Asp Phe Asn
50 55 60

Cys Tyr Asp Arg Gln Glu Cys Val Ala Thr Glu Glu Asn Pro Gln Val
65 70 75 80

Tyr Phe Cys Cys Cys Glu Gly Asn Phe Cys Asn Glu Arg Phe Thr His
85 90 95

Leu Pro Glu Ala Gly Gly Pro Glu Val Thr Tyr Glu Pro Pro Pro Thr
100 105 110

Ala Pro Thr Gly Gly Gly Thr His Thr Cys Pro Pro Cys Pro Ala Pro
115 120 125

Glu Leu Leu Gly Gly Pro Ser Val Phe Leu Phe Pro Pro Lys Pro Lys
130 135 140

Asp Thr Leu Met Ile Ser Arg Thr Pro Glu Val Thr Cys Val Val Val
145 150 155 160

Asp Val Ser His Glu Asp Pro Glu Val Lys Phe Asn Trp Tyr Val Asp
165 170 175

Gly Val Glu Val His Asn Ala Lys Thr Lys Pro Arg Glu Glu Gln Tyr
180 185 190

Asn Ser Thr Tyr Arg Val Val Ser Val Leu Thr Val Leu His Gln Asp
195 200 205

Trp Leu Asn Gly Lys Glu Tyr Lys Cys Lys Val Ser Asn Lys Ala Leu
210 215 220

-continued

Pro Ala Pro Ile Glu Lys Thr Ile Ser Lys Ala Lys Gly Gln Pro Arg
225 230 235 240

Glu Pro Gln Val Tyr Thr Leu Pro Pro Cys Arg Glu Glu Met Thr Lys
245 250 255

Asn Gln Val Ser Leu Trp Cys Leu Val Lys Gly Phe Tyr Pro Ser Asp
260 265 270

Ile Ala Val Glu Trp Glu Ser Asn Gly Gln Pro Glu Asn Asn Tyr Lys
275 280 285

Thr Thr Pro Pro Val Leu Asp Ser Asp Gly Ser Phe Phe Leu Tyr Ser
290 295 300

Lys Leu Thr Val Asp Lys Ser Arg Trp Gln Gln Gly Asn Val Phe Ser
305 310 315 320

Cys Ser Val Met His Glu Ala Leu His Asn His Tyr Thr Gln Lys Ser
325 330 335

Leu Ser Leu Ser Pro Gly Lys
340

<210> SEQ ID NO 47
<211> LENGTH: 356
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Met Asp Ala Met Lys Arg Gly Leu Cys Cys Val Leu Leu Leu Cys Gly
1 5 10 15

Ala Val Phe Val Ser Pro Gly Ala Ser Gly Pro Arg Gly Val Gln Ala
20 25 30

Leu Leu Cys Ala Cys Thr Ser Cys Leu Gln Ala Asn Tyr Thr Cys Glu
35 40 45

Thr Asp Gly Ala Cys Met Val Ser Ile Phe Asn Leu Asp Gly Met Glu
50 55 60

His His Val Arg Thr Cys Ile Pro Lys Val Glu Leu Val Pro Ala Gly
65 70 75 80

Lys Pro Phe Tyr Cys Leu Ser Ser Glu Asp Leu Arg Asn Thr His Cys
85 90 95

Cys Tyr Thr Asp Tyr Cys Asn Arg Ile Asp Leu Arg Val Pro Ser Gly
100 105 110

His Leu Lys Glu Pro Glu His Pro Ser Met Trp Gly Pro Val Glu Thr
115 120 125

Gly Gly Gly Thr His Thr Cys Pro Pro Cys Pro Ala Pro Glu Leu Leu
130 135 140

Gly Gly Pro Ser Val Phe Leu Phe Pro Pro Lys Pro Lys Asp Thr Leu
145 150 155 160

Met Ile Ser Arg Thr Pro Glu Val Thr Cys Val Val Val Asp Val Ser
165 170 175

His Glu Asp Pro Glu Val Lys Phe Asn Trp Tyr Val Asp Gly Val Glu
180 185 190

Val His Asn Ala Lys Thr Lys Pro Arg Glu Glu Gln Tyr Asn Ser Thr
195 200 205

Tyr Arg Val Val Ser Val Leu Thr Val Leu His Gln Asp Trp Leu Asn
210 215 220

Gly Lys Glu Tyr Lys Cys Lys Val Ser Asn Lys Ala Leu Pro Ala Pro
225 230 235 240

```
Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355


<210> SEQ ID NO 48
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
```

-continued

```
225                 230                 235                 240

Glu Glu Met Thr Lys Asn Gln Val Ser Leu Ser Cys Ala Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Val Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330


<210> SEQ ID NO 49
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115


<210> SEQ ID NO 50
<211> LENGTH: 150
<212> TYPE: PRT
<213> ORGANISM: Rattus norvegicus

<400> SEQUENCE: 50

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
```

```
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 51
<211> LENGTH: 150
<212> TYPE: PRT
<213> ORGANISM: Sus scrofa

<400> SEQUENCE: 51

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 52
<211> LENGTH: 150
<212> TYPE: PRT
<213> ORGANISM: Mus musculus

<400> SEQUENCE: 52

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
```

```
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 53
<211> LENGTH: 150
<212> TYPE: PRT
<213> ORGANISM: Homo sapiens

<400> SEQUENCE: 53

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 54
<211> LENGTH: 150
<212> TYPE: PRT
<213> ORGANISM: Bos taurus

<400> SEQUENCE: 54

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Arg Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
```

```
        115                 120                 125

Pro Pro Thr Ala Pro Thr Leu Leu Thr Val Leu Ala Tyr Ser Leu Leu
    130                 135                 140

Pro Val Gly Gly Leu Ser
145                 150


<210> SEQ ID NO 55
<211> LENGTH: 150
<212> TYPE: PRT
<213> ORGANISM: Xenopus sp.

<400> SEQUENCE: 55

Met Gly Ala Ser Val Ala Leu Thr Phe Leu Leu Leu Leu Ala Thr Phe
1               5                   10                  15

Arg Ala Gly Ser Gly His Asp Glu Val Glu Thr Arg Glu Cys Ile Tyr
            20                  25                  30

Tyr Asn Ala Asn Trp Glu Leu Glu Lys Thr Asn Gln Ser Gly Val Glu
        35                  40                  45

Arg Leu Val Glu Gly Lys Lys Asp Lys Arg Leu His Cys Tyr Ala Ser
    50                  55                  60

Trp Arg Asn Asn Ser Gly Phe Ile Glu Leu Val Lys Lys Gly Cys Trp
65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Cys Glu Gly Asn Tyr Cys Asn
            100                 105                 110

Lys Lys Phe Thr His Leu Pro Glu Val Glu Thr Phe Asp Pro Lys Pro
        115                 120                 125

Gln Pro Ser Ala Ser Val Leu Asn Ile Leu Ile Tyr Ser Leu Leu Pro
    130                 135                 140

Ile Val Gly Leu Ser Met
145                 150


<210> SEQ ID NO 56
<211> LENGTH: 150
<212> TYPE: PRT
<213> ORGANISM: Homo sapiens

<400> SEQUENCE: 56

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
```

```
    130                 135                 140

Val Pro Leu Met Leu Ile
145                 150


<210> SEQ ID NO 57
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Thr, Ala or absent
<220> FEATURE:
<221> NAME/KEY: MOD_RES
<222> LOCATION: (121)..(121)
<223> OTHER INFORMATION: Pro, Ala, Val or Met

<400> SEQUENCE: 57

Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Glu Gln Asp Lys Arg Leu His Cys Tyr Ala Ser
    50                  55                  60

Trp Arg Asn Ser Ser Gly Thr Ile Glu Leu Val Lys Lys Gly Cys Trp
65                  70                  75                  80

Leu Asp Asp Phe Asn Cys Tyr Asp Arg Gln Glu Cys Val Ala Thr Glu
                85                  90                  95

Glu Asn Pro Gln Val Tyr Phe Cys Cys Cys Glu Gly Asn Phe Cys Asn
            100                 105                 110

Glu Arg Phe Thr His Leu Pro Glu Xaa Gly Gly Pro Glu Val Thr Tyr
        115                 120                 125

Glu Pro Lys Pro Pro Thr Ala Pro Thr Leu Leu Thr Val Leu Ala Tyr
    130                 135                 140

Ser Leu Leu Pro Ile Gly Gly Leu Ser Met
145                 150


<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Gly Gly Ser
1               5


<210> SEQ ID NO 59
<211> LENGTH: 103
<212> TYPE: PRT
<213> ORGANISM: Homo sapiens

<400> SEQUENCE: 59

Ser Gly Pro Arg Gly Val Gln Ala Leu Leu Cys Ala Cys Thr Ser Cys
1               5                   10                  15
```

-continued

```
Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100


<210> SEQ ID NO 60
<211> LENGTH: 103
<212> TYPE: PRT
<213> ORGANISM: Condylura cristata

<400> SEQUENCE: 60

Ser Gly Pro Arg Gly Ile Gln Ala Leu Leu Cys Ala Cys Thr Ser Cys
1               5                   10                  15

Leu Gln Ala Asn Leu Thr Cys Glu Thr Asp Gly Ala Cys Met Val Ser
            20                  25                  30

Ile Phe Asn Leu Asp Gly Leu Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Phe Cys Asn Lys
65                  70                  75                  80

Ile Asp Leu Arg Val Pro Ser Gly His Val Lys Glu Pro Glu Arg Pro
                85                  90                  95

Ser Val Trp Gly Pro Val Glu
            100


<210> SEQ ID NO 61
<211> LENGTH: 103
<212> TYPE: PRT
<213> ORGANISM: Erinaceus europaeus

<400> SEQUENCE: 61

Ser Gly Pro Arg Gly Ile Gln Ala Leu Leu Cys Ala Cys Thr Ser Cys
1               5                   10                  15

Leu Gln Thr Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Phe Cys Asn Arg
65                  70                  75                  80

Ile Asp Leu Arg Val Pro Ser Gly His Pro Lys Glu Ser Glu Gln Ala
                85                  90                  95

Ser Met Trp Gly Pro Val Glu
            100


<210> SEQ ID NO 62
<211> LENGTH: 102
```

```
<212> TYPE: PRT
<213> ORGANISM: Gallus gallus

<400> SEQUENCE: 62

Ala Pro Gly Gly Ala Arg Ala Leu Thr Cys Leu Cys Ser Asp Cys Lys
1               5                   10                  15

Gln Ala Asn Ser Thr Cys Glu Thr Asp Gly Ala Cys Met Val Ser Val
            20                  25                  30

Phe Asn Leu Asp Gly Val Lys His His Val Arg Thr Cys Ile Pro Glu
        35                  40                  45

Ala Lys Leu Ile Pro Ala Gly Lys Pro Phe Tyr Cys Leu Ser Ser Glu
    50                  55                  60

Asp Leu Arg Asn Thr His Cys Cys Tyr Ser Asp Phe Cys Asn Lys Ile
65                  70                  75                  80

Asp Leu Met Val Pro Ser Gly His Leu Lys Asp Asn Glu Pro Pro Ser
                85                  90                  95

Ser Trp Gly Pro Val Glu
            100


<210> SEQ ID NO 63
<211> LENGTH: 103
<212> TYPE: PRT
<213> ORGANISM: Mus musculus

<400> SEQUENCE: 63

Ser Gly Pro Arg Gly Ile Gln Ala Leu Leu Cys Ala Cys Thr Ser Cys
1               5                   10                  15

Leu Gln Thr Asn Tyr Thr Cys Glu Thr Asp Gly Ala Cys Met Val Ser
            20                  25                  30

Ile Phe Asn Leu Asp Gly Val Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Ile Asp Phe Cys Asn Lys
65                  70                  75                  80

Ile Asp Leu Arg Val Pro Ser Gly His Leu Lys Glu Pro Ala His Pro
                85                  90                  95

Ser Met Trp Gly Pro Val Glu
            100


<210> SEQ ID NO 64
<211> LENGTH: 103
<212> TYPE: PRT
<213> ORGANISM: Sus scrofa

<400> SEQUENCE: 64

Ser Gly Pro Arg Gly Ile Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Phe Cys Asn Lys
65                  70                  75                  80

Ile Asp Leu Arg Val Pro Ser Gly His Leu Lys Glu Pro Glu His Pro
```

-continued

```
                85                  90                  95

Ser Met Trp Gly Pro Val Glu
            100


<210> SEQ ID NO 65
<211> LENGTH: 103
<212> TYPE: PRT
<213> ORGANISM: Rattus norvegicus

<400> SEQUENCE: 65

Ser Gly Pro Arg Gly Ile Gln Ala Leu Leu Cys Ala Cys Thr Ser Cys
1               5                   10                  15

Leu Gln Thr Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Ile Asp Phe Cys Asn Lys
65                  70                  75                  80

Ile Asp Leu Arg Val Pro Ser Gly His Leu Lys Glu Pro Glu His Pro
                85                  90                  95

Ser Met Trp Gly Pro Val Glu
            100


<210> SEQ ID NO 66
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Glu Glu Met Thr Glu Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
```

```
            180                 185                 190

Ser Arg Trp Gln Gln Gly Asn Val Phe Ser Cys Ser Val Met His Glu
        195                 200                 205

Ala Leu His Asn His Tyr Thr Gln Asp Ser Leu Ser Leu Ser Pro Gly
    210                 215                 220

Lys
225


<210> SEQ ID NO 67
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
        115                 120                 125

Leu Pro Pro Ser Arg Glu Glu Met Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Arg Gly Gln Pro Glu Asn Asn Tyr Lys Thr Thr Pro Pro Val Leu
                165                 170                 175

Asp Ser Arg Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225


<210> SEQ ID NO 68
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Thr His Thr Cys Pro Pro Cys Pro Ala Pro Glu Leu Leu Gly Gly Pro
```

-continued

```
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Glu Glu Met Thr Lys Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn Arg Tyr Thr Gln Lys Ser Leu Ser Leu Ser Pro Gly
    210                 215                 220

Lys
225


<210> SEQ ID NO 69

<400> SEQUENCE: 69

000


<210> SEQ ID NO 70
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95
```

-continued

```
Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Cys Arg Glu Glu Met Thr Glu Asn Gln Val Ser Leu Trp Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Asp Ser Leu Ser Leu Ser Pro Gly
        355                 360                 365
```

<210> SEQ ID NO 71
<211> LENGTH: 1101
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
atggatgcaa tgaagagagg gctctgctgt gtgctgctgc tgtgtggagc agtcttcgtt      60

tcgcccggcg cctctgggcg tggggaggct gagacacggg agtgcatcta ctacaacgcc     120

aactgggagc tggagcgcac caaccagagc ggcctggagc gctgcgaagg cgagcaggac     180

aagcggctgc actgctacgc ctcctggcgc aacagctctg gcaccatcga gctcgtgaag     240

aagggctgct ggctagatga cttcaactgc tacgataggc aggagtgtgt ggccactgag     300

gagaaccccc aggtgtactt ctgctgctgt gaaggcaact tctgcaacga gcgcttcact     360

catttgccag aggctggggg cccggaagtc acgtacgagc cacccccgac agcccccacc     420

ggtggtggaa ctcacacatg cccaccgtgc ccagcacctg aactcctggg gggaccgtca     480
```

```
gtcttcctct tcccccaaa acccaaggac accctcatga tctcccggac ccctgaggtc    540

acatgcgtgg tggtggacgt gagccacgaa gaccctgagg tcaagttcaa ctggtacgtg    600

gacggcgtgg aggtgcataa tgccaagaca aagccgcggg aggagcagta caacagcacg    660

taccgtgtgg tcagcgtcct caccgtcctg caccaggact ggctgaatgg caaggagtac    720

aagtgcaagg tctccaacaa agccctccca gcccccatcg agaaaaccat ctccaaagcc    780

aaagggcagc cccgagaacc acaggtgtac accctgcccc catgccggga ggagatgacc    840

gagaaccagg tcagcctgtg gtgcctggtc aaaggcttct atcccagcga catcgccgtg    900

gagtgggaga gcaatgggca gccggagaac aactacaaga ccacgcctcc cgtgctggac    960

tccgacggct ccttcttcct ctatagcaag ctcaccgtgg acaagagcag gtggcagcag   1020

gggaacgtct tctcatgctc cgtgatgcat gaggctctgc acaaccacta cacgcaggac   1080

agcctctccc tgtctccggg t                                             1101
```

```
<210> SEQ ID NO 72
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Glu Glu Met Thr Glu
```

```
                245                 250                 255

Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Asp Ser
                325                 330                 335

Leu Ser Leu Ser Pro Gly
            340
```

<210> SEQ ID NO 73
<211> LENGTH: 1026
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
gggcgtgggg aggctgagac acgggagtgc atctactaca acgccaactg ggagctggag     60

cgcaccaacc agagcggcct ggagcgctgc gaaggcgagc aggacaagcg gctgcactgc    120

tacgcctcct ggcgcaacag ctctggcacc atcgagctcg tgaagaaggg ctgctggcta    180

gatgacttca actgctacga taggcaggag tgtgtggcca ctgaggagaa cccccaggtg    240

tacttctgct gctgtgaagg caacttctgc aacgagcgct tcactcattt gccagaggct    300

gggggcccgg aagtcacgta cgagccaccc ccgacagccc ccaccggtgg tggaactcac    360

acatgcccac cgtgcccagc acctgaactc ctggggggac cgtcagtctt cctcttcccc    420

ccaaaaccca aggacaccct catgatctcc cggacccctg aggtcacatg cgtggtggtg    480

gacgtgagcc acgaagaccc tgaggtcaag ttcaactggt acgtggacgg cgtggaggtg    540

cataatgcca agacaaagcc gcgggaggag cagtacaaca gcacgtaccg tgtggtcagc    600

gtcctcaccg tcctgcacca ggactggctg aatggcaagg agtacaagtg caaggtctcc    660

aacaaagccc tcccagcccc catcgagaaa accatctcca aagccaaagg gcagccccga    720

gaaccacagg tgtacaccct gcccccatgc cgggaggaga tgaccgagaa ccaggtcagc    780

ctgtggtgcc tggtcaaagg cttctatccc agcgacatcg ccgtggagtg ggagagcaat    840

gggcagccgg agaacaacta caagaccacg cctcccgtgc tggactccga cggctccttc    900

ttcctctata gcaagctcac cgtggacaag agcaggtggc agcaggggaa cgtcttctca    960

tgctccgtga tgcatgaggc tctgcacaac cactacacgc aggacagcct ctccctgtct   1020

ccgggt                                                              1026
```

<210> SEQ ID NO 74
<211> LENGTH: 356
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Met Asp Ala Met Lys Arg Gly Leu Cys Cys Val Leu Leu Leu Cys Gly
```

-continued

```
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Arg Gly Gln Pro Glu Asn Asn Tyr Lys Thr Thr Pro
    290                 295                 300

Pro Val Leu Asp Ser Arg Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355
```

<210> SEQ ID NO 75
<211> LENGTH: 1068
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 75

-continued

```
atggatgcaa tgaagagagg gctctgctgt gtgctgctgc tgtgtggagc agtcttcgtt     60

tcgcccggcg cctccgggcc ccggggggtc caggctctgc tgtgtgcgtg caccagctgc    120

ctccaggcca actacacgtg tgagacagat ggggcctgca tggtttccat tttcaatctg    180

gatgggatgg agcaccatgt gcgcacctgc atccccaaag tggagctggt ccctgccggg    240

aagcccttct actgcctgag ctcggaggac ctgcgcaaca cccactgctg ctacactgac    300

tactgcaaca ggatcgactt gagggtgccc agtggtcacc tcaaggagcc tgagcacccg    360

tccatgtggg gcccggtgga gaccggtggt ggaactcaca catgcccacc gtgcccagca    420

cctgaactcc tggggggacc gtcagtcttc ctcttccccc caaaacccaa ggacaccctc    480

atgatctccc ggacccctga ggtcacatgc gtggtggtgg acgtgagcca cgaagaccct    540

gaggtcaagt tcaactggta cgtggacggc gtggaggtgc ataatgccaa gacaaagccg    600

cgggaggagc agtacaacag cacgtaccgt gtggtcagcg tcctcaccgt cctgcaccag    660

gactggctga atggcaagga gtacaagtgc aaggtctcca acaaagccct cccagccccc    720

atcgagaaaa ccatctccaa agccaaaggg cagccccgag aaccacaggt gtgcaccctg    780

cccccatccc gggaggagat gaccaagaac caggtcagcc tgtcctgcgc cgtcaaaggc    840

ttctatccca gcgacatcgc cgtggagtgg gagagccgcg ggcagccgga gaacaactac    900

aagaccacgc ctcccgtgct ggactcccgc ggctccttct tcctcgtgag caagctcacc    960

gtggacaaga gcaggtggca gcaggggaac gtcttctcat gctccgtgat gcatgaggct   1020

ctgcacaacc actacacgca gaagagcctc tccctgtctc cgggtaaa                1068
```

<210> SEQ ID NO 76
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175
```

-continued

```
Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255

Phe Tyr Pro Ser Asp Ile Ala Val Glu Trp Glu Ser Arg Gly Gln Pro
            260                 265                 270

Glu Asn Asn Tyr Lys Thr Thr Pro Pro Val Leu Asp Ser Arg Gly Ser
        275                 280                 285

Phe Phe Leu Val Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330
```

```
<210> SEQ ID NO 77
<211> LENGTH: 996
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

tccgggcccc ggggggtcca ggctctgctg tgtgcgtgca ccagctgcct ccaggccaac     60

tacacgtgtg agacagatgg ggcctgcatg gtttccattt tcaatctgga tgggatggag    120

caccatgtgc gcacctgcat ccccaaagtg gagctggtcc ctgccgggaa gcccttctac    180

tgcctgagct cggaggacct gcgcaacacc cactgctgct acactgacta ctgcaacagg    240

atcgacttga gggtgcccag tggtcacctc aaggagcctg agcacccgtc catgtggggc    300

ccggtggaga ccggtggtgg aactcacaca tgcccaccgt gcccagcacc tgaactcctg    360

gggggaccgt cagtcttcct cttcccccca aaacccaagg acaccctcat gatctcccgg    420

acccctgagg tcacatgcgt ggtggtggac gtgagccacg aagaccctga ggtcaagttc    480

aactggtacg tggacggcgt ggaggtgcat aatgccaaga caaagccgcg ggaggagcag    540

tacaacagca cgtaccgtgt ggtcagcgtc ctcaccgtcc tgcaccagga ctggctgaat    600

ggcaaggagt acaagtgcaa ggtctccaac aaagccctcc cagcccccat cgagaaaacc    660

atctccaaag ccaaagggca gccccgagaa ccacaggtgt gcaccctgcc cccatcccgg    720

gaggagatga ccaagaacca ggtcagcctg tcctgcgccg tcaaaggctt ctatcccagc    780

gacatcgccg tggagtggga gagccgcggg cagccggaga acaactacaa gaccacgcct    840

cccgtgctgg actcccgcgg ctccttcttc ctcgtgagca agctcaccgt ggacaagagc    900

aggtggcagc aggggaacgt cttctcatgc tccgtgatgc atgaggctct gcacaaccac    960

tacacgcaga agagcctctc cctgtctccg ggtaaa                              996

<210> SEQ ID NO 78
<211> LENGTH: 368
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Cys Arg Glu Glu Met Thr Lys Asn Gln Val Ser Leu Trp Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn Arg Tyr Thr Gln Lys Ser Leu Ser Leu Ser Pro Gly Lys
        355                 360                 365
```

<210> SEQ ID NO 79

<211> LENGTH: 1104
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 79

```
atggatgcaa tgaagagagg gctctgctgt gtgctgctgc tgtgtggagc agtcttcgtt     60

tcgcccggcg cctctgggcg tggggaggct gagacacggg agtgcatcta ctacaacgcc    120

aactgggagc tggagcgcac caaccagagc ggcctggagc gctgcgaagg cgagcaggac    180

aagcggctgc actgctacgc ctcctggcgc aacagctctg gcaccatcga gctcgtgaag    240

aagggctgct ggctagatga cttcaactgc tacgataggc aggagtgtgt ggccactgag    300

gagaaccccc aggtgtactt ctgctgctgt gaaggcaact tctgcaacga gcgcttcact    360

catttgccag aggctggggg cccggaagtc acgtacgagc cacccccgac agcccccacc    420

ggtggtggaa ctcacacatg cccaccgtgc ccagcacctg aactcctggg gggaccgtca    480

gtcttcctct tccccccaaa acccaaggac accctcatga tctcccggac ccctgaggtc    540

acatgcgtgg tggtggacgt gagccacgaa gaccctgagg tcaagttcaa ctggtacgtg    600

gacggcgtgg aggtgcataa tgccaagaca aagccgcggg aggagcagta caacagcacg    660

taccgtgtgg tcagcgtcct caccgtcctg caccaggact ggctgaatgg caaggagtac    720

aagtgcaagg tctccaacaa agccctccca gcccccatcg agaaaaccat ctccaaagcc    780

aaagggcagc cccgagaacc acaggtgtac accctgcccc catgccggga ggagatgacc    840

aagaaccagg tcagcctgtg gtgcctggtc aaaggcttct atcccagcga catcgccgtg    900

gagtgggaga gcaatgggca gccggagaac aactacaaga ccacgcctcc cgtgctggac    960

tccgacggct ccttcttcct ctatagcaag ctcaccgtgg acaagagcag gtggcagcag   1020

gggaacgtct tctcatgctc cgtgatgcat gaggctctgc acaaccgcta cacgcagaag   1080

agcctctccc tgtctccggg taaa                                          1104
```

<210> SEQ ID NO 80
<211> LENGTH: 343
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110
```

-continued

```
Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Glu Glu Met Thr Lys
                245                 250                 255

Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn Arg Tyr Thr Gln Lys Ser
                325                 330                 335

Leu Ser Leu Ser Pro Gly Lys
            340
```

<210> SEQ ID NO 81
<211> LENGTH: 1029
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
gggcgtgggg aggctgagac acgggagtgc atctactaca acgccaactg ggagctggag     60

cgcaccaacc agagcggcct ggagcgctgc gaaggcgagc aggacaagcg gctgcactgc    120

tacgcctcct ggcgcaacag ctctggcacc atcgagctcg tgaagaaggg ctgctggcta    180

gatgacttca actgctacga taggcaggag tgtgtggcca ctgaggagaa cccccaggtg    240

tacttctgct gctgtgaagg caacttctgc aacgagcgct tcactcattt gccagaggct    300

gggggcccgg aagtcacgta cgagccaccc ccgacagccc ccaccggtgg tggaactcac    360

acatgcccac cgtgcccagc acctgaactc ctgggggggac cgtcagtctt cctcttcccc    420

ccaaaaccca aggacaccct catgatctcc cggacccctg aggtcacatg cgtggtggtg    480

gacgtgagcc acgaagaccc tgaggtcaag ttcaactggt acgtggacgg cgtggaggtg    540

cataatgcca agacaaagcc gcgggaggag cagtacaaca gcacgtaccg tgtggtcagc    600

gtcctcaccg tcctgcacca ggactggctg aatggcaagg agtacaagtg caaggtctcc    660

aacaaagccc tcccagcccc catcgagaaa accatctcca aagccaaagg gcagccccga    720
```

```
gaaccacagg tgtacaccct gcccccatgc cgggaggaga tgaccaagaa ccaggtcagc    780

ctgtggtgcc tggtcaaagg cttctatccc agcgacatcg ccgtggagtg ggagagcaat    840

gggcagccgg agaacaacta caagaccacg cctcccgtgc tggactccga cggctccttc    900

ttcctctata gcaagctcac cgtggacaag agcaggtggc agcaggggaa cgtcttctca    960

tgctccgtga tgcatgaggc tctgcacaac cgctacacgc agaagagcct ctccctgtct   1020

ccgggtaaa                                                           1029
```

<210> SEQ ID NO 82
<211> LENGTH: 1068
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

```
atggatgcaa tgaagagagg gctctgctgt gtgctgctgc tgtgtggagc agtcttcgtt     60

tcgcccggcg cctccgggcc ccgggggtc caggctctgc tgtgtgcgtg caccagctgc    120

ctccaggcca actacacgtg tgagacagat ggggcctgca tggtttccat tttcaatctg    180

gatgggatgg agcaccatgt gcgcacctgc atccccaaag tggagctggt ccctgccggg    240

aagcccttct actgcctgag ctcggaggac ctgcgcaaca cccactgctg ctacactgac    300

tactgcaaca ggatcgactt gagggtgccc agtggtcacc tcaaggagcc tgagcacccg    360

tccatgtggg gcccggtgga gaccggtggt ggaactcaca catgcccacc gtgcccagca    420

cctgaactcc tggggggacc gtcagtcttc ctcttccccc caaaacccaa ggacaccctc    480

atgatctccc ggacccctga ggtcacatgc gtggtggtgg acgtgagcca cgaagaccct    540

gaggtcaagt tcaactggta cgtggacggc gtggaggtgc ataatgccaa gacaaagccg    600

cgggaggagc agtacaacag cacgtaccgt gtggtcagcg tcctcaccgt cctgcaccag    660

gactggctga atggcaagga gtacaagtgc aaggtctcca acaaagccct cccagccccc    720

atcgagaaaa ccatctccaa agccaaaggg cagccccgag aaccacaggt gtgcaccctg    780

cccccatccc gggaggagat gaccaagaac caggtcagcc tgtcctgcgc cgtcaaaggc    840

ttctatccca gcgacatcgc cgtggagtgg gagagcaatg ggcagccgga gaacaactac    900

aagaccacgc ctcccgtgct ggactccgac ggctccttct tcctcgtgag caagctcacc    960

gtggacaaga gcaggtggca gcaggggaac gtcttctcat gctccgtgat gcatgaggct   1020

ctgcacaacc actacacgca gaagagcctc tccctgtctc cgggtaaa                1068
```

<210> SEQ ID NO 83
<211> LENGTH: 996
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
tccgggcccc ggggggtcca ggctctgctg tgtgcgtgca ccagctgcct ccaggccaac     60

tacacgtgtg agacagatgg ggcctgcatg gtttccattt tcaatctgga tgggatggag    120

caccatgtgc gcacctgcat ccccaaagtg gagctggtcc ctgccgggaa gcccttctac    180

tgcctgagct cggaggacct gcgcaacacc cactgctgct acactgacta ctgcaacagg    240
```

-continued

```
atcgacttga gggtgcccag tggtcacctc aaggagcctg agcacccgtc catgtggggc    300

ccggtggaga ccggtggtgg aactcacaca tgcccaccgt gcccagcacc tgaactcctg    360

gggggaccgt cagtcttcct cttcccccca aaacccaagg acaccctcat gatctcccgg    420

acccctgagg tcacatgcgt ggtggtggac gtgagccacg aagaccctga ggtcaagttc    480

aactggtacg tggacggcgt ggaggtgcat aatgccaaga caaagccgcg ggaggagcag    540

tacaacagca cgtaccgtgt ggtcagcgtc ctcaccgtcc tgcaccagga ctggctgaat    600

ggcaaggagt acaagtgcaa ggtctccaac aaagccctcc cagcccccat cgagaaaacc    660

atctccaaag ccaaagggca gccccgagaa ccacaggtgt gcaccctgcc cccatcccgg    720

gaggagatga ccaagaacca ggtcagcctg tcctgcgccg tcaaaggctt ctatcccagc    780

gacatcgccg tggagtggga gagcaatggg cagccggaga acaactacaa gaccacgcct    840

cccgtgctgg actccgacgg ctccttcttc ctcgtgagca agctcaccgt ggacaagagc    900

aggtggcagc aggggaacgt cttctcatgc tccgtgatgc atgaggctct gcacaaccac    960

tacacgcaga agagcctctc cctgtctccg ggtaaa                              996
```

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(10)
<223> OTHER INFORMATION: This sequence may encompass 2-10 residues

<400> SEQUENCE: 84

```
Gly Gly Gly Gly Gly Gly Gly Gly Gly Gly
1               5                   10
```

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(5)
<223> OTHER INFORMATION: This sequence may encompass 2-5 residues

<400> SEQUENCE: 85

```
Gly Gly Gly Gly Gly
1               5
```

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(4)
<223> OTHER INFORMATION: This sequence may encompass 2-4 residues

<400> SEQUENCE: 86

```
Gly Gly Gly Gly
1
```

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 87

His His His His His His
1 5

<210> SEQ ID NO 88
<211> LENGTH: 225
<212> TYPE: PRT
<213> ORGANISM: Homo sapiens

<400> SEQUENCE: 88

Thr His Thr Cys Pro Pro Cys Pro Ala Pro Glu Leu Leu Gly Gly Pro
1 5 10 15

Ser Val Phe Leu Phe Pro Pro Lys Pro Lys Asp Thr Leu Met Ile Ser
20 25 30

Arg Thr Pro Glu Val Thr Cys Val Val Val Asp Val Ser His Glu Asp
35 40 45

Pro Glu Val Lys Phe Asn Trp Tyr Val Asp Gly Val Glu Val His Asn
50 55 60

Ala Lys Thr Lys Pro Arg Glu Glu Gln Tyr Asn Ser Thr Tyr Arg Val
65 70 75 80

Val Ser Val Leu Thr Val Leu His Gln Asp Trp Leu Asn Gly Lys Glu
85 90 95

Tyr Lys Cys Lys Val Ser Asn Lys Ala Leu Pro Ala Pro Ile Glu Lys
100 105 110

Thr Ile Ser Lys Ala Lys Gly Gln Pro Arg Glu Pro Gln Val Tyr Thr
115 120 125

Leu Pro Pro Ser Arg Glu Glu Met Thr Lys Asn Gln Val Ser Leu Thr
130 135 140

Cys Leu Val Lys Gly Phe Tyr Pro Ser Asp Ile Ala Val Glu Trp Glu
145 150 155 160

Ser Asn Gly Gln Pro Glu Asn Asn Tyr Lys Thr Thr Pro Pro Val Leu
165 170 175

Asp Ser Asp Gly Ser Phe Phe Leu Tyr Ser Lys Leu Thr Val Asp Lys
180 185 190

Ser Arg Trp Gln Gln Gly Asn Val Phe Ser Cys Ser Val Met His Glu
195 200 205

Ala Leu His Asn His Tyr Thr Gln Lys Ser Leu Ser Leu Ser Pro Gly
210 215 220

Lys
225

<210> SEQ ID NO 89
<211> LENGTH: 229
<212> TYPE: PRT
<213> ORGANISM: Homo sapiens

<400> SEQUENCE: 89

Glu Ser Lys Tyr Gly Pro Pro Cys Pro Ser Cys Pro Ala Pro Glu Phe
1 5 10 15

```
Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 90
<211> LENGTH: 223
<212> TYPE: PRT
<213> ORGANISM: Homo sapiens

<400> SEQUENCE: 90

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160
```

-continued

```
Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220


<210> SEQ ID NO 91
<211> LENGTH: 232
<212> TYPE: PRT
<213> ORGANISM: Homo sapiens

<400> SEQUENCE: 91

Glu Pro Lys Ser Cys Asp Thr Pro Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Lys Trp Tyr Val
    50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
    210                 215                 220

Ser Leu Ser Leu Ser Pro Gly Lys
225                 230
```

COMPOSITIONS AND METHODS FOR TREATING SPINAL MUSCULAR ATROPHY

RELATED APPLICATIONS

This patent application is a national-stage application of International Application No. PCT/US2018/25689, filed Apr. 2, 2018, which claims priority to U.S. Provisional Patent Application No. 62/480,835, filed Apr. 3, 2017. The entire contents of these applications are hereby incorporated by this reference in their entireties.

SEQUENCE LISTING

The instant application contains a Sequence Listing which has been submitted electronically in ASCII format and is hereby incorporated by reference in its entirety. Said ASCI copy, created on Apr. 3, 2018, is named APH-00325_SL.txt and is 159,180 bytes in size.

BACKGROUND OF THE INVENTION

Spinal muscular atrophy (SMA), also called autosomal recessive proximal spinal muscular atrophy, is a rare neuromuscular disorder characterized by loss of motor neurons and progressive muscle wasting, often leading to early death. The disorder is caused by a genetic defect in the SMN1 gene, which encodes SMN, a protein widely expressed in all eukaryotic cells and necessary for survival of motor neurons. Lower levels of the protein results in loss of function of neuronal cells in the anterior horn of the spinal cord and subsequent system-wide muscle wasting (atrophy).

Spinal muscular atrophy is an inherited disorder and is passed on in an autosomal recessive manner. SMA manifests in various degrees of severity, which all have in common progressive muscle wasting and mobility impairment. Proximal muscles and lung muscles are affected first. Other body systems may be affected as well, particularly in early-onset forms of the disorder. SMA is the most common genetic cause of infant death.

Nusinersen, marketed as Spinraza, is the first drug approved by the U.S. Food and Drug Administration for use in treating spinal muscular atrophy (SMA). It is a biologic drug that binds to mutated RNA. While being effective in increasing motor function in some patients, nusinersen is not effective treating all SMA patients. Moreover, like other antisense drugs, nusinersen treatment is associated with increased risk of abnormalities in blood clotting, reduction in platelets, kidney damage as well as other side effects (e.g., increased risk of infection and scoliosis).

Thus, it is an objective of the present disclosure to provide alternative compositions and methods for treating SMA.

SUMMARY OF THE INVENTION

In part, the data presented herein demonstrates that ALK4:ActRIIB antagonists (inhibitors) can be used to treat spinal muscular atrophy (SMA). For example, it was shown that a soluble ALK4:ActRIIB heterodimer may be used to prevent or reduce the severity of muscle and bone loss in a SMA model. Moreover, ALK4:ActRIIB treatment increased muscle strength in SMA patients. As described herein, ALK4:ActRIIB heterodimer proteins are a unique antagonist of ligands of the TGF-beta superfamily, exhibiting a different ligand-binding profile/selectivity compared to corresponding ActRIIB and ALK4 homodimers. In particular, an exemplary ALK4:ActRIIB heterodimer displays enhanced binding to activin B compared to either homodimer, retains strong binding to activin A, GDF8, and GDF11 as observed with ActRIIB homodimer, intermediated binding to BMP6, and exhibits substantially reduced binding to BMP9, BMP10, and GDF3. In fact, the ALK4:ActRIIB heterodimer displays low to no observable affinity for BMP9, whereas this ligand binds strongly to ActRIIB homodimer. See FIG. 4. These results therefore demonstrate that ALK4:ActRIIB heterodimers are a more selective antagonists (inhibitors) of certain ligands of the TGF-beta superfamily compared to ActRIIB homodimers. Thus, the disclosure establishes that antagonists of ALK4:ActRIIB signaling (e.g., signaling mediated by one or more of activin, GDF11, GDF8, BMP6, GDF3, and BMP10) may be used to treat SMA. While ALK4:ActRIIB heterodimers may affect SMA through a mechanism other than ALK4:ActRIIB antagonism, the disclosure nonetheless demonstrates that desirable therapeutic agents may be selected on the basis of ALK4:ActRIIB signaling antagonism activity. Therefore, in some embodiments, the disclosure provides method for using various ALK4:ActRIIB signaling antagonists for treating SMA including, for example, antagonists that inhibit one or more ALK4:ActRIIB-associated ligands, particularly one or more of activin A, activin B, GDF11, GDF8, BMP6, GDF3, and BMP10; antagonists that inhibit one or more type I- or type II-(e.g., ALK4 and ActRIIB); and antagonists that inhibit one or more downstream signaling components (e.g., Smad proteins such as Smads 2 and 3). As used herein, such signaling antagonists are collectively referred to as "ALK4:ActRIIB antagonists" or "ALK4:ActRIIB inhibitors".

Accordingly, the disclosure provides in part, ALK4:ActRIIB antagonists compositions and methods for treating spinal muscular atrophy SMA. In some embodiments, the method prevents or delays onset and/or reduces the severity or duration of one or more complications of SMA including, for example, areflexia, particularly in the extremities; muscle loss; overall muscle weakness; respiratory complications; respiratory failure; respiratory insufficiency; poor muscle tone; limpness or a tendency to flop; difficulty in achieving developmental milestones; difficulty sitting, standing, and/walking; loss of strength of respiratory muscles, often resulting in weak cough, weak cry, accumulation of secretions in lungs or throat, and/or respiratory distress; fasciculations of the tongue; bone loss (e.g., low bone mineral density) and/or weakness; difficulty sucking or swallowing. In some embodiments, the method increases bone mineral density in the patient. In some embodiments, the method increases bone strength in the patient. In some embodiments, the method increases muscle mass in the patient. In some embodiments, the method increases muscle strength in the patient. In some embodiments, the patient has SMA1. In some embodiments, the patient has SMA2, in some embodiments, the patient has SMA3. In some embodiments, the patient has SMA4. In some embodiments, the method results in improvement in motor milestones according to Section 2 of the Hammersmith Infant Neurologic Exam (HINE). In some embodiments, the method results in at least a 2-point increase in ability to kick in accordance with Section 2 of HINE. In some embodiments, the method results in at least a 1-point increase in the motor milestones of head control, rolling, sitting, crawling, standing, voluntary grasp, or walking in accordance with section 2 of HINE. In some embodiments, the method results in improvement in motor function according to the Children's Hospital of Philadelphia Infant Test of Neuromuscular Disorders (CHOP Intend). In some embodiments, the method further comprises administration of an additional active agent or supportive therapy for treating SMA. In some embodiments, the method comprises administering an ALK4:ActRIIB antagonists in combination with nusinersen. In some embodiments, the method comprises administering an ALK4:ActRIIB antagonists in combination with one or more additional active agents or supportive therapies selected from: SMN1 gene replacement (e.g., AVXS-101 gene therapy), SMN2 alternative splicing modulation (e.g., branaplam, RG7916, RG3039, PTK-SMA1, RG7800, sodium orthovanadate, and aclarubicin), SMN2 gene activation (e.g., salbutamol, butyrates, valproic acid, hydroxycarbamide), histone deacetylase inhibitors, benzamide M344, hydroxamic acids (e.g., CBHA, SBHA, entinostat, panobinostat, trichostatin A, and vorinostat), prolactin, natural polyphenol compounds (e.g., resveratrol and curcumin), p38 pathway activators (e.g., celecoxib), SMN stabilization (e.g., aminoglycosides and indoprofen), neuroprotection (e.g., olesoxime, thyrotropin-releasing hormone, riluzole, beta-lactam antibiotics (e.g., ceftriaxone), and muscle restoration (e.g., CK-2127107).

In certain aspects, an ALK4:ActRIIB antagonist, or combination of antagonists, to be used in accordance with methods and uses described herein is an agent that inhibits at least GDF11. Effects on GDF11 inhibition may be determined, for example, using a cell-based assay including those described herein (e.g., Smad signaling reporter assay). Therefore, in some embodiments, a GDF11 antagonist, or combination of antagonist, of the disclosure may bind to at least GDF11. Ligand binding activity may be determined, for example, using a binding affinity assay including, for example, those described herein. In some embodiments, an ALK4:ActRIIB antagonist, or combination of antagonists, of the disclosure binds to at least GDF11 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M).

In certain aspects, an ALK4:ActRIIB antagonist, or combination of antagonists, to be used in accordance with methods and uses described herein is an agent that inhibits at least GDF8. Effects on GDF8 inhibition may be determined, for example, using a cell-based assay including those described herein (e.g., Smad signaling reporter assay). Therefore, in some embodiments, a GDF8 antagonist, or combination of antagonist, of the disclosure may bind to at least GDF8. Ligand binding activity may be determined, for example, using a binding affinity assay including, for example, those described herein. In some embodiments, an ALK4:ActRIIB antagonist, or combination of antagonists, of the disclosure binds to at least GDF8 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M).

In certain aspects, an ALK4:ActRIIB antagonist, or combination of antagonists, to be used in accordance with methods and uses described herein is an agent that inhibits at least activin (e.g. activin A, activin B, activin C, activin E, activin AB, and activin AE). Effects on activin inhibition may be determined, for example, using a cell-based assay including those described herein (e.g., Smad signaling reporter assay). Therefore, in some embodiments, an activin antagonist, or combination of antagonist, of the disclosure may bind to at least activin. Ligand binding activity may be determined, for example, using a binding affinity assay including, for example, those described herein. In some embodiments, an ALK4:ActRIIB antagonist, or combination of antagonists, of the disclosure binds to at least activin A, activin B, activin AB, activin C, and/or activin E with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). In some embodiments, an ALK4:ActRIIB antagonist, or combination of antagonists, of the disclosure binds to at least activin A with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M).

In certain aspects, an ALK4:ActRIIB antagonist, or combination of antagonists, to be used in accordance with methods and uses described herein is an agent that inhibits at least BMP6. Effects on BMP6 inhibition may be determined, for example, using a cell-based assay including those described herein (e.g., Smad signaling reporter assay). Therefore, in some embodiments, a BMP6 antagonist, or combination of antagonist, of the disclosure may bind to at least BMP6. Ligand binding activity may be determined, for example, using a binding affinity assay including, for example, those described herein. In some embodiments, an ALK4:ActRIIB antagonist, or combination of antagonists, of the disclosure binds to at least BMP6 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M).

In certain aspects, an ALK4:ActRIIB antagonist, or combination of antagonists, to be used in accordance with methods and uses described herein is an agent that inhibits at least GDF3. Effects on GDF3 inhibition may be determined, for example, using a cell-based assay including those described herein (e.g., Smad signaling reporter assay). Therefore, in some embodiments, a GDF3 antagonist, or combination of antagonist, of the disclosure may bind to at least GDF3. Ligand binding activity may be determined, for example, using a binding affinity assay including, for example, those described herein. In some embodiments, an ALK4:ActRIIB antagonist, or combination of antagonists, of the disclosure binds to at least GDF3 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M).

In certain aspects, an ALK4:ActRIIB antagonist, or combination of antagonists, to be used in accordance with methods and uses described herein is an agent that inhibits at least BMP10. Effects on BMP10 inhibition may be determined, for example, using a cell-based assay including those described herein (e.g., Smad signaling reporter assay). Therefore, in some embodiments, a BMP10 antagonist, or combination of antagonist, of the disclosure may bind to at least BMP10. Ligand binding activity may be determined, for example, using a binding affinity assay including, for example, those described herein. In some embodiments, an ALK4:ActRIIB antagonist, or combination of antagonists, of the disclosure binds to at least BMP10 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M).

In certain aspects, an ALK4:ActRIIB antagonist, or combination of antagonists, to be used in accordance with methods and uses described herein is an agent that inhibits at least ActRIIB Effects on ActRIIB inhibition may be determined, for example, using a cell-based assay including those described herein (e.g., Smad signaling reporter assay). Therefore, in some embodiments, an ALK4:ActRIIB antagonist, or combination of antagonist, of the disclosure may bind to at least ActRIIB Ligand binding activity may be determined, for example, using a binding affinity assay including, for example, those described herein. In some embodiments, an ALK4:ActRIIB antagonist, or combination of antagonists, of the disclosure binds to at least ActRIIB with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). In some embodiments, an ALK4:ActRIIB antagonist that binds to and/or inhibits ActRIIB may further bind to and/or inhibit ActRIIA.

In certain aspects, an ALK4:ActRIIB antagonist, or combination of antagonists, to be used in accordance with methods and uses described herein is an agent that inhibits at least ALK4. Effects on ALK4 inhibition may be determined, for example, using a cell-based assay including those described herein (e.g., Smad signaling reporter assay). Therefore, in some embodiments, an ALK4:ActRIIB antagonist, or combination of antagonist, of the disclosure may bind to at least ALK4. Ligand binding activity may be determined, for example, using a binding affinity assay including, for example, those described herein. In some embodiments, an ALK4:ActRIIB antagonist, or combination of antagonists, of the disclosure binds to at least ALK4 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M).

The present disclosure relates, in part, to heteromultimer complexes (heteromultimers) comprising at least one ALK4 polypeptide and at least one ActRIIB polypeptide (ALK4:ActRIIB heteromultimers). Preferably, ALK4 polypeptides comprise a ligand-binding domain of an ALK4 receptor, for example, a portion of the ALK4 extracellular domain. Similarly, ActRIIB polypeptides generally comprise a ligand-binding domain of an ActRIIB receptor, for example, a portion of the ActRIIB extracellular domain. Preferably, such ALK4 and ActRIIB polypeptides, as well as resultant heteromultimers thereof, are soluble. Preferably, such ALK4 and ActRIIB polypeptides, as well as resultant heteromultimers thereof, are recombinant proteins. Preferably, such ALK4 and ActRIIB polypeptides, as well as resultant heteromultimers thereof, are isolated proteins.

In certain aspects, an ALK4:ActRIIB heteromultimer comprises an ALK4 domain comprising an amino acid sequence that is at least 70% identical to a polypeptide that begins at any one of amino acids 24-34 of SEQ ID NO: 9 (e.g., amino acids 24, 25, 26, 27, 28, 29, 30, 31, 32, 33, and 34) and ends at any one of amino acids 101-126 of SEQ ID NO: 9 (e.g., amino acids 101, 102, 103, 104, 105, 106, 107, 108, 109, 110, 111, 112, 113, 114, 115, 116, 117, 118, 119, 120, 121, 122, 123, 124, 125, and 126). For example, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-101 of SEQ ID NO: 9. In some embodiments, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-126 of SEQ ID NO: 9. In some embodiments, ALK4:ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 10.

In other aspects, an ALK4:ActRIIB heteromultimer comprises an ALK4 domain comprising an amino acid sequence that is at least 70% identical to a polypeptide that begins at any one of amino acids 24-34 of SEQ ID NO: 19 (e.g., amino acids 24, 25, 26, 27, 28, 29, 30, 31, 32, 33, and 34) and ends at any one of amino acids 101-126 of SEQ ID NO: 19 (e.g., amino acids 101, 102, 103, 104, 105, 106, 107, 108, 109, 110, 111, 112, 113, 114, 115, 116, 117, 118, 119, 120, 121, 122, 123, 124, 125, and 126). For example, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-101 of SEQ ID NO: 19. In some embodiments, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-126 of SEQ ID NO: 19. In some embodiments, ALK4:ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 20.

In certain aspects, an ALK4:ActRIIB heteromultimer comprises an ActRIIB domain comprising an amino acid sequence that is at least 70% identical to a polypeptide that begins at any one of amino acids 20-29 of SEQ ID NO: 1 (e.g., amino acids 20, 21, 22, 23, 24, 25, 26, 27, 28, and 29) and ends at any one of amino acids 109-134 (109, 110, 111, 112, 113, 114, 115, 116, 117, 118, 119, 120, 121, 122, 123, 124, 125, 126, 127, 128, 129, 130, 131, 132, 133, and 134) of SEQ ID NO: 1. For example, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 29-109 of SEQ ID NO: 1. In some embodiments, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 25-131 of SEQ ID NO: 1. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 2. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 3. In some embodiments, ALK4:ActRIIB heteromultimers do not comprise an ActRIIB polypeptide comprising an acidic amino acid (e.g., the naturally occurring amino acids E or D or an artificial acidic amino acid) at the position corresponding to L79 of SEQ ID NO: 1.

In other aspects, an ALK4:ActRIIB heteromultimer comprises an ActRIIB domain comprising an amino acid sequence that is at least 70% identical to a polypeptide that begins at any one of amino acids 20-29 of SEQ ID NO: 4 (e.g., amino acids 20, 21, 22, 23, 24, 25, 26, 27, 28, and 29) and ends at any one of amino acids 109-134 (109, 110, 111, 112, 113, 114, 115, 116, 117, 118, 119, 120, 121, 122, 123, 124, 125, 126, 127, 128, 129, 130, 131, 132, 133, and 134) of SEQ ID NO: 4. For example, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 29-109 of SEQ ID NO: 4. In some embodiments, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 25-131 of SEQ ID NO: 4. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 5. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 6. In some embodiments, ALK4: ActRIIB heteromultimers do not comprise an ActRIIB polypeptide comprising an acidic amino acid (e.g., the naturally occurring amino acids E or D or an artificial acidic amino acid) at the position corresponding to L79 of SEQ ID NO: 1.

As described herein, ALK4:ActRIIB heteromultimer structures include, for example, heterodimers, heterotrimers, heterotetramers, heteropentamers, and higher order heteromultimer complexes. See, e.g., FIG. 6. In certain preferred embodiments, ALK4:ActRIIB heteromultimers are heterodimers.

In certain aspects, ALK4 and/or ActRIIB polypeptides may be fusion proteins. For example, in some embodiments, an ALK4 polypeptide may be a fusion protein comprising an ALK4 polypeptide domain and one or more heterologous (non-ALK4) polypeptide domains (e.g., ALK4-Fc fusion proteins). Similarly, in some embodiments, an ActRIIB polypeptide may be a fusion protein comprising an ActRIIB polypeptide domain and one or more heterologous (non-ActRIIB) polypeptide domains (ActRIIB-Fc fusion proteins).

In some embodiments, ALK4 polypeptides are fusion proteins that comprise an Fc domain of an immunoglobulin. Similarly, in some embodiments, ActRIIB polypeptides are fusion proteins that comprise an Fc domain of an immunoglobulin. Traditional Fc fusion proteins and antibodies are examples of unguided interaction pairs, whereas a variety of engineered Fc domains have been designed as asymmetric interaction pairs [Spiess et al (2015) Molecular Immunology 67(2A): 95-106]. Therefore, a first member and/or a second member of an interaction pair described herein may comprise a constant domain of an immunoglobulin, including, for example, the Fc portion of an immunoglobulin. For example, a first member of an interaction pair may comprise an amino acid sequence that is derived from an Fc domain of an IgG (IgG1, IgG2, IgG3, or IgG4), IgA (IgA1 or IgA2), IgE, or IgM immunoglobulin. Such immunoglobulin domains may comprise one or more amino acid modifications (e.g., deletions, additions, and/or substitutions) that promote ALK4:ActRIIB heteromultimer formation. Similarly, a second member of an interaction pair may comprise an amino acid sequence that is derived from an Fc domain of an IgG (IgG1, IgG2, IgG3, or IgG4), IgA (IgA1 or IgA2), IgE, or IgM. Such immunoglobulin domains may comprise one or more amino acid modifications (e.g., deletions, additions, and/or substitutions) that promote ALK4:ActRIIB heteromultimer formation. For example, the second member of an interaction pair may comprise, consist essentially of, or consist of an amino acid sequence that is at least 70%, 75%, 80%, 85%, 90%, 91%, 92%, 93%, 94%, 95%, 96%, 97%, 98%, 99% or 100% identical to any one of SEQ ID NOs: 23-37 and 66-68. In some embodiments, a first member and a second member of an interaction pair comprise Fc domains derived from the same immunoglobulin class and subtype. In other embodiments, a first member and a second member of an interaction pair comprise Fc domains derived from different immunoglobulin classes or subtypes.

Optionally, ALK4 polypeptides are connected directly (fused) to one or more heterologous domains, or an intervening sequence, such as a linker, may be positioned between the amino acid sequence of the ALK4 polypeptide and the one or more heterologous domains (e.g., an Fc domain of an immunoglobulin). Similarly, the ActRIIB polypeptide may be connected directly (fused) to one or more heterologous domains, or an intervening sequence, such as a linker, may be positioned between the amino acid sequence of the ActRIIB polypeptide and the one or more heterologous domains (e.g., an Fc domain of an immunoglobulin). Linkers may correspond to the roughly 15 amino acid unstructured region at the C-terminal end of the extracellular domain of ActRIIB or ALK4 (the "tail"), or it may be an artificial sequence of between 5 and 15, 20, 30, 50, 100 or more amino acids that are relatively free of secondary structure. A linker may be rich in glycine and proline residues and may, for example, contain repeating sequences of threonine/serine and glycines. Examples of linkers include, but are not limited to, the sequences TGGG (SEQ ID NO: 17), SGGG (SEQ ID NO: 18), TGGGG (SEQ ID NO: 15), SGGGG (SEQ ID NO: 16), GGGGS (SEQ ID NO: 58), GGGG (SEQ ID NO: 14), and GGG (SEQ ID NO: 13). Such immunoglobulin domains may comprise one or more amino acid modifications (e.g., deletions, additions, and/or substitutions) that confer an altered Fc activity, e.g., decrease of one or more Fc effector functions. In some embodiment, an ActRIIB or ALK4 fusion protein comprises an amino acid sequence as set forth in the formula A-B-C. For example, the B portion is an N- and C-terminally truncated ActRIIB polypeptide or ALK4 polypeptide as described herein. The A and C portions may be independently zero, one, or more than one amino acids, and both A and C portions are heterologous to B. The A and/or C portions may be attached to the B portion via a linker sequence. In certain embodiments, an ActRIIB or ALK4 fusion protein comprises a leader sequence. The leader sequence may be a native ActRIIB or ALK4 leader sequence (e.g., a native ActRIIB or ALK4 leader sequence) or a heterologous leader sequence. In certain embodiments, the leader sequence is a tissue plasminogen activator (TPA) leader sequence.

In some embodiments, ALK4:ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 44. In some embodiments, ALK4: ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 48. In some embodiments, ALK4:ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 76. In some embodiments, ALK4:ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 42. In some embodiments, ALK4:ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 47. In some embodiments, ALK4:ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 74.

In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 41. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 46. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 72. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 80. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 78. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 70. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 45. In some embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 39. In certain preferred embodiments, the ActRIIB domain of the ActRIIB-Fc fusion protein does not comprise an acidic amino acid (e.g., E or D or an artificially acidic amino acid) at the position corresponding to L79 of SEQ ID NO: 1.

Optionally, an ALK4 and/or ActRIIB polypeptide comprises one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. ALK4 and/or ActRIIB polypeptides may comprise at least one N-linked sugar, and may include two, three or more N-linked sugars. Such polypeptides may also comprise O-linked sugars. ALK4 and/or ActRIIB polypeptides may be produced in a variety of cell lines that glycosylate the protein in a manner that is suitable for patient use, including engineered insect or yeast cells, and mammalian cells such as COS cells, CHO cells, HEK cells and NSO cells. In some embodiments an ALK4 and/or ActRIIB polypeptide is glycosylated and has a glycosylation pattern obtainable from a Chinese hamster ovary cell line. Preferably ALK4:ActRIIB heteromultimer complexes of the disclosure exhibit a serum half-life of at least 4, 6, 12, 24, 36, 48, or 72 hours in a mammal (e.g., a mouse or a human). Optionally, ALK4:ActRIIB heteromultimers may exhibit a serum half-life of at least 6, 8, 10, 12, 14, 20, 25, or 30 days in a mammal (e.g., a mouse or a human).

In certain aspects, ALK4:ActRIIB heteromultimers of the disclosure bind to one or more TGF-beta superfamily ligands. Optionally, ALK4:ActRIIB heteromultimers bind to one or more of these ligands with a $K_D$ of less than or equal to $10^{-8}$, $10^{-9}$, $10^{-10}$, $10^{-11}$, or $10^{-12}$M. For example, in some embodiments, ALK4:ActRIIB heteromultimers bind to activin B. In some embodiments, ALK4:ActRIIB heteromultimers bind to activin A. In some embodiments, ALK4:ActRIIB heteromultimers bind to activin AB. In some embodiments, ALK4:ActRIIB heteromultimers bind to activin C. In some embodiments, ALK4:ActRIIB heteromultimers bind to activin AC. In some embodiments, ALK4:ActRIIB heteromultimers bind to activin BC. In some embodiments, ALK4:ActRIIB heteromultimers bind to activin BC. In some embodiments, ALK4:ActRIIB heteromultimers bind to activin BE. In some embodiments, ALK4:ActRIIB heteromultimers bind to GDF11. In some embodiments, ALK4:ActRIIB heteromultimers bind to GDF8. In some embodiments, ALK4:ActRIIB heteromultimers bind to BMP6. In some embodiments, ALK4:ActRIIB heteromultimers bind to GDF3. In some embodiments, ALK4:ActRIIB heteromultimers bind to BMP10. In some embodiments, ALK4:ActRIIB heteromultimers do not bind to, or do not substantially bind to, BMP9 (e.g., bind with a $K_D$ of greater than or equal to $10^{-8}$ or $10^{-7}$). In some embodiments, ALK4:ActRIIB heteromultimers bind to activin B with stronger affinity compared to a corresponding ActRIIB homomultimer. In some embodiments, ALK4:ActRIIB heteromultimers bind to GDF3 with weaker affinity compared to a corresponding ActRIIB homomultimer. In some embodiments, ALK4:ActRIIB heteromultimers bind to BMP10 with weaker affinity compared to a corresponding ActRIIB homomultimer. In some embodiments, ALK4:ActRIIB heteromultimers bind to BMP9 with weaker affinity compared to a corresponding ActRIIB homomultimer.

In general, ALK4:ActRIIB heteromultimers of the disclosure antagonize (inhibit) one or more activities of at least one TGF-beta superfamily ligand, and such alterations in activity may be measured using various assays known in the art, including, for example, a cell-based assay such as those described herein. In certain aspects, ALK4:ActRIIB heteromultimers may be used to inhibit signaling (e.g., Smad 2/3 and/or Smad 1/5/8 signaling) mediated by one or more TGFβ superfamily ligands in, for example, a cell-based assay. For example, in some embodiments, ALK4:ActRIIB heteromultimers inhibit activin signaling in a cell-based assay. In some embodiments, ALK4:ActRIIB heteromultimers inhibit activin signaling in a cell-based assay. In some embodiments, ALK4:ActRIIB heteromultimers inhibit activin A signaling in a cell-based assay. In some embodiments, ALK4:ActRIIB heteromultimers inhibit activin B signaling in a cell-based assay. In some embodiments, ALK4:ActRIIB heteromultimers inhibit activin AB signaling in a cell-based assay. In some embodiments, ALK4:ActRIIB heteromultimers inhibit activin C signaling in a cell-based assay. In some embodiments, ALK4:ActRIIB heteromultimers inhibit activin AC signaling in a cell-based assay. In some embodiments, ALK4:ActRIIB heteromultimers inhibit activin BC signaling in a cell-based assay. In some embodiments, ALK4:ActRIIB heteromultimers inhibit activin E signaling in a cell-based assay. In some embodiments, ALK4:ActRIIB heteromultimers inhibit activin AE signaling in a cell-based assay. In some embodiments, ALK4:ActRIIB heteromultimers inhibit activin CE signaling in a cell-based assay. In some embodiments, ALK4:ActRIIB heteromultimers inhibit GDF11 signaling in a cell-based assay. In some embodiments, ALK4:ActRIIB heteromultimers inhibit GDF8 signaling in a cell-based assay. In some embodiments, ALK4:ActRIIB heteromultimers inhibit BMP6 signaling in a cell-based assay. In some embodiments, ALK4:ActRIIB heteromultimers inhibit GDF3 signaling in a cell-based assay. In some embodiments, ALK4:ActRIIB heteromultimers inhibit BMP10 signaling in a cell-based assay. In some embodiments, ALK4:ActRIIB heteromultimers does not inhibit, or does not substantially inhibit, BMP9 signaling in a cell-based assay. In some embodiments, ALK4:ActRIIB heteromultimers are stronger inhibitors of activin B signaling in a cell-based assay. In some embodiments, ALK4:ActRIIB heteromultimers are weaker inhibitors of GDF3 signaling in a cell-based assay. In some embodiments, ALK4:ActRIIB heteromultimers are weaker inhibitors of BMP10 signaling in a cell-based assay. In some embodiments, ALK4:ActRIIB heteromultimers are weaker inhibitors of BMP9 signaling in a cell-based assay.

Any of the ALK4:ActRIIB heteromultimers described herein may be formulated as a pharmaceutical preparation (compositions). In some embodiments, pharmaceutical preparations comprise a pharmaceutically acceptable carrier. In some embodiments, a pharmaceutical preparation will be pyrogen-free (meaning pyrogen free to the extent required by regulations governing the quality of products for therapeutic use). A pharmaceutical preparation may also include one or more additional compounds such as a compound that is used to treat a disorder/condition described herein. In general, ALK4:ActRIIB heteromultimer pharmaceutical preparations are substantially free of ALK4 and/or ActRIIB homomultimers. For example, in some embodiments, ALK4:ActRIIB heteromultimer pharmaceutical preparations comprise less than about 10%, 9%, 8%, 7%, 6%, 5%, 4%, 3%, 2%, or less than about 1% ALK4 homomultimers. In some embodiments, ALK4:ActRIIB heteromultimer pharmaceutical preparations comprise less than about 10%, 9%, 8%, 7%, 6%, 5%, 4%, 3%, 2%, or less than about 1% ActRIIB homomultimers. In some embodiments, ALK4: ActRIIB heteromultimer pharmaceutical preparations comprise less than about 10%, 9%, 8%, 7%, 6%, 5%, 4%, 3%, 2%, or less than about 1% ALK4 homomultimers and less than about 10%, 9%, 8%, 7%, 6%, 5%, 4%, 3%, 2%, or less than about 1% ActRIIB homomultimers.

In certain aspects, the disclosure provides nucleic acids encoding an ActRIIB polypeptide as described herein. For example, an ActRIIB nucleic acid may comprise of a nucleic acid that is at least 70%, 75%, 80%, 85%, 86%, 87%, 88%, 89%, 90%, 91%, 92%, 93%, 94%, 95%, 96%, 97%, 98%, 99%, or 100% identical to the sequence of 73-396 of SEQ ID NO: 7 or one that hybridizes under stringent conditions to the complement of nucleotides 73-396 of SEQ ID NO: 7. Such an nucleic acid may be one that comprises the sequence of SEQ ID NOs: 8. In some embodiments, an ActRIIB nucleic acids comprises a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 71. In some embodiments, an ActRIIB nucleic acids comprises a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 73. In some embodiments, an ActRIIB nucleic acids comprises a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 79. In some embodiments, an ActRIIB nucleic acids comprises a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 81.

In certain aspects, the disclosure provides nucleic acids encoding an ActRIIB polypeptide as described herein. For example, an ALK4 nucleic acid may comprise, consists essentially of, or consists of a nucleic acid that is at least 70%, 75%, 80%, 85%, 86%, 87%, 88%, 89%, 90%, 91%, 92%, 93%, 94%, 95%, 96%, 97%, 98%, 99%, or 100% identical to the sequence of 70-378 of SEQ ID NO: 11 or one that hybridizes under stringent conditions to the complement of nucleotides 70-378 of SEQ ID NO: 11. In some embodiments, an ALK4 nucleic acids comprises a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 75. In some embodiments, an ALK4 nucleic acids comprises a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 77. In some embodiments, an ALK4 nucleic acids comprises a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 82. In some embodiments, an ALK4 nucleic acids comprises a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 83.

In certain aspects, the present disclosure provides nucleic acids sequence comprising a coding sequence for and ALK4 polypeptide and a coding sequence for the ActRIIB polypeptide. For example, in some embodiments, nucleic acids of the disclosure a) comprises a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to any one of SEQ ID NOs: 71, 73, 79, and 77, and b) comprises, consists essentially of, or consists of a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to any one of SEQ ID Nos: 75, 77, 82, and 83.

Preferably, ALK4 and/or ActRIIB nucleic acids are isolated and/or recombinant nucleic acids. Nucleic acids disclosed herein may be operably linked to a promoter for expression. The present disclosure further provides vectors comprising such ALK4 and/or ActRIIB polynucleotides as well as cells (e.g., CHO cells), preferably cells isolated from a human or other vertebrate species, comprising such ALK4 and/or ActRIIB polynucleotides as well as vectors comprising such ALK4 and/or ActRIIB polynucleotides.

In certain aspects, an ALK4 polypeptides and/or ActRIIB polypeptides may be expressed in a mammalian cell line, optionally a cell line that mediates suitably natural glycosylation of the ActRIIB or ALK4 protein so as to diminish the likelihood of an unfavorable immune response in a patient (including the possibility of veterinary patients). Human and CHO cell lines have been used successfully, and it is expected that other common mammalian expression vectors will be useful. Thus the disclosure provides cultured cells comprising any of the nucleic acids disclosed herein. Such cells may be mammalian cells, including CHO cells, NSO cells, HEK cells and COS cells. Other cells may be chosen depending on the species of the intended patient. Other cells are disclosed herein. Cultured cells are understood to mean cells maintained in laboratory or other man-made conditions (e.g., frozen, or in media) and not part of a living organism.

In certain aspects, the disclosure provides methods for making any of the ALK4 and ActRIIB polypeptides described herein as well as ALK4:ActRIIB heteromultimer complexes comprising such polypeptides. Such a method may include expressing any of the nucleic acids disclosed herein in a suitable cell (e.g., CHO cell or a COS cell). For example, in some embodiments a method of making a heteromultimer comprising an ALK4 polypeptide and an ActRIIB polypeptide comprises: culturing a cell under conditions suitable for expression of an ALK4 polypeptide and an ActRIIB polypeptide, wherein the cell comprises an ALK4 polynucleotide and an ActRIIB polynucleotide; optionally recovering the heteromultimer so expressed. Alternatively, a method of making a heteromultimer comprising an ALK4 polypeptide and an ActRIIB polypeptide may comprise: a) culturing a first cell under conditions suitable for expression of an ALK4 polypeptide, wherein the first cell comprises an ALK4 polynucleotide; b) recovering the ALK4 polypeptide so expressed; c) culturing a second cell under conditions suitable for expression of an ActRIIB polypeptide, wherein the second cell comprises an ActRIIB polynucleotide; d) recovering the ActRIIB polypeptide so expressed; e) combining the recovered ALK4 polypeptide and the recovered ActRIIB polypeptide under conditions suitable for ALK4:ActRIIB heteromultimer formation; optionally recovering the ALK4:ActRIIB heteromultimer. In certain embodiments, ALK4 and/or ActRIIB polypeptides are expressed using a TPA leader sequence (e.g., SEQ ID NO: 38). In certain embodiments, ALK4 and/or ActRIIB polypeptides are expressed in a CHO cell. ALK4 and ActRIIB polypeptides described herein, as well as protein complexes of the same, may be recovered as crude, partially purified, or highly purified fractions using any of the well-known techniques for obtaining protein from cell cultures. In general, such methods result in ALK4:ActRIIB heteromultimers that substantially free of ALK4 and/or ActRIIB homomultimers. For example, in some embodiments, methods for producing ALK4:ActRIIB heteromultimers result in less than about 10%, 9%, 8%, 7%, 6%, 5%, 4%, 3%, 2%, or less than about 1% ALK4 homomultimers. In some embodiments, methods for producing ALK4:ActRIIB heteromultimers result in less than about 10%, 9%, 8%, 7%, 6%, 5%, 4%, 3%, 2%, or less than about 1% ActRIIB homomultimers. In some embodiments, methods for producing ALK4: ActRIIB heteromultimers result in less than about 10%, 9%, 8%, 7%, 6%, 5%, 4%, 3%, 2%, or less than about 1% ALK4 homomultimers and less than about 10%, 9%, 8%, 7%, 6%, 5%, 4%, 3%, 2%, or less than about 1% ActRIIB homomultimers.

In certain aspects, an ALK4:ActRIIB antagonist of the disclosure is an antibody or combination of antibodies. In some embodiments, the ALK4:ActRIIB antagonist is a multispecific antibody. In some embodiments, the ALK4: ActRIIB antagonist is a bi-specific antibody. In some embodiments, the ALK4:ActRIIB antagonist antibody binds to one or more ligands selected from: activin A, activin B, GDF11, GDF8, GDF3, BMP6, and BMP10. In some embodiments, the ALK4:ActRIIB antagonist antibody binds activin B. In some embodiments, the ALK4:ActRIIB antagonist antibody binds to ActRIIB In some embodiments, the ALK4:ActRIIB antagonist antibody binds to ActRIIA and ActRIIB In some embodiments, the ALK4:ActRIIB antagonist antibody binds to ALK4. In some embodiments, an ALK4:ActRIIB antagonist antibody that binds to one or more of activin A, activin B, GDF11, GDF8, GDF3, BMP6, and BMP10 further binds to one or more of ActRIIB and ALK4.

BRIEF DESCRIPTION OF THE DRAWINGS

FIG. 1 shows an alignment of extracellular domains of human ActRIIA (SEQ ID NO: 49) and human ActRIIB (SEQ ID NO: 2) with the residues that are deduced herein, based on composite analysis of multiple ActRIIB and ActRIIA crystal structures, to directly contact ligand indicated with boxes.

FIG. 3 shows multiple sequence alignment of Fc domains from human IgG isotypes using Clustal 2.1. Hinge regions are indicated by dotted underline. Double underline indicates examples of positions engineered in IgG1 Fc to promote asymmetric chain pairing and the corresponding positions with respect to other isotypes IgG2, IgG3 and IgG4. FIG. 3 discloses SEQ ID NOS 88-91, respectively, an order of appearance.

DETAILED DESCRIPTION OF THE INVENTION

1. Overview

Figure 2:
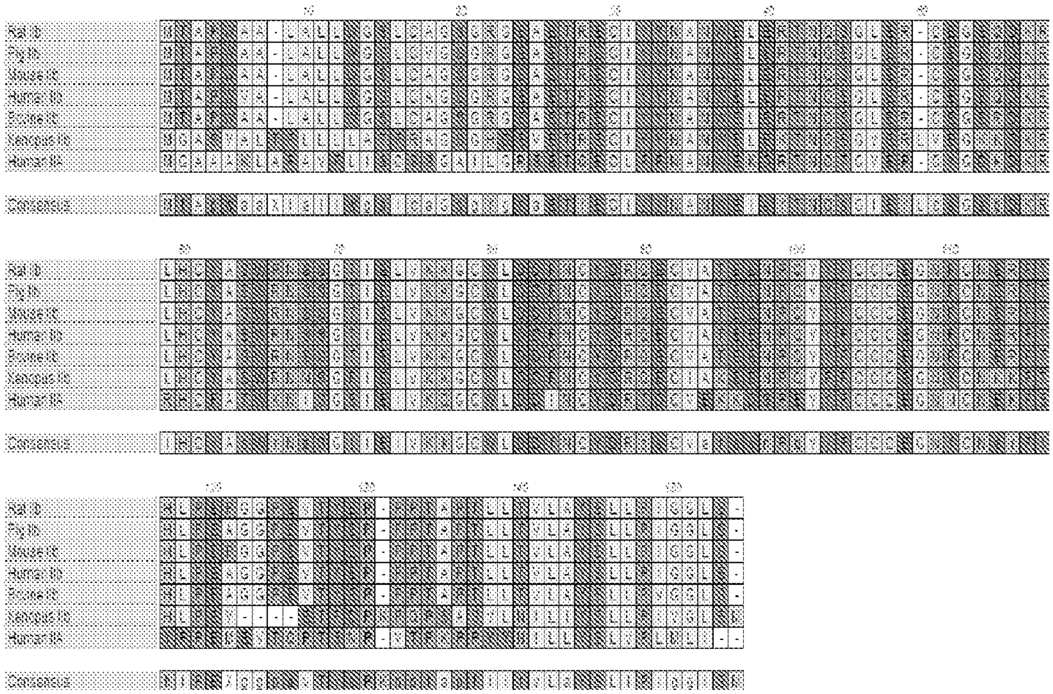
FIG. 2 shows a multiple sequence alignment of various vertebrate ActRIIB precursor proteins without their intracellular domains (SEQ ID NOs: 50-55, respectively) human ActRIIA precursor protein without its intracellular domain (SEQ ID NO: 56), and a consensus ActRII precursor protein (SEQ ID NO: 57).

In part, the disclosure provides heteromultimers that comprise an ALK4 polypeptide and an ActRIIB polypeptide for use in treating spinal muscular atrophy (SMA). Preferably such ALK4 polypeptides comprise a ligand-binding domain of an ALK4 receptor and such ActRIIB polypeptides comprise a ligand-binding domain of an ActRIIB receptor. In certain preferred embodiments, ALK4:ActRIIB heteromultimers of the disclosure have an altered TGFβ superfamily ligand binding profile/specificity compared to a corresponding sample of a homomultimer (e.g., an ALK4:ActRIIB heterodimer compared to an ActRIIB:ActRIIB homodimer or an ALK4:ALK4 homodimer).

The TGF-β superfamily is comprised of over 30 secreted factors including TGF-betas, activins, nodals, bone morphogenetic proteins (BMPs), growth and differentiation factors (GDFs), and anti-Mullerian hormone (AMH) [Weiss et al. (2013) Developmental Biology, 2(1): 47-63]. Members of the superfamily, which are found in both vertebrates and invertebrates, are ubiquitously expressed in diverse tissues and function during the earliest stages of development throughout the lifetime of an animal. Indeed, TGF-β superfamily proteins are key mediators of stem cell self-renewal, gastrulation, differentiation, organ morphogenesis, and adult tissue homeostasis.

Ligands of the TGF-beta superfamily share the same dimeric structure in which the central 3½ turn helix of one monomer packs against the concave surface formed by the beta-strands of the other monomer. The majority of TGF-beta family members are further stabilized by an intermolecular disulfide bond. This disulfide bonds traverses through a ring formed by two other disulfide bonds generating what has been termed a 'cysteine knot' motif [Lin et al. (2006) Reproduction 132: 179-190; and Hinck et al. (2012) FEBS Letters 586: 1860-1870].

TGF-beta superfamily signaling is mediated by heteromeric complexes of type I and type II serine/threonine kinase receptors, which phosphorylate and activate downstream SMAD proteins (e.g., SMAD proteins 1, 2, 3, 5, and 8) upon ligand stimulation [Massagué (2000) Nat. Rev. Mol. Cell Biol. 1:169-178]. These type I and type II receptors are transmembrane proteins, composed of a ligand-binding extracellular domain with cysteine-rich region, a transmembrane domain, and a cytoplasmic domain with predicted serine/threonine kinase specificity. In general, type I receptors mediate intracellular signaling while the type II receptors are required for binding TGF-beta superfamily ligands. Type I and II receptors form a stable complex after ligand binding, resulting in phosphorylation of type I receptors by type II receptors.

The TGF-beta family can be divided into two phylogenetic branches based on the type I receptors they bind and the Smad proteins they activate. One is the more recently evolved branch, which includes, e.g., the TGF-betas, activins, GDF8, GDF9, GDF11, BMP3 and nodal, which signal through type I receptors that activate Smads 2 and 3 [Hinck (2012) FEBS Letters 586:1860-1870]. The other branch comprises the more distantly related proteins of the superfamily and includes, e.g., BMP2, BMP4, BMP5, BMP6, BMP7, BMP8a, BMP8b, BMP9, BMP10, GDF1, GDF5, GDF6, and GDF7, which signal through Smads 1, 5, and 8.

Activins are members of the TGF-beta superfamily and were initially discovered as regulators of secretion of follicle-stimulating hormone, but subsequently various reproductive and non-reproductive roles have been characterized. There are three principal activin forms (A, B, and AB) that are homo/heterodimers of two closely related β subunits ($\beta_A\beta_A$, $\beta_B\beta_B$, and $\beta_A\beta_B$, respectively). The human genome also encodes an activin C and an activin E, which are primarily expressed in the liver, and heterodimeric forms containing $\beta_C$ or $\beta_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos [DePaolo et al. (1991) Proc Soc Ep Biol Med. 198:500-512; Dyson et al. (1997) Curr Biol. 7:81-84; and Woodruff (1998) Biochem Pharmacol. 55:953-963]. In several tissues, activin signaling is antagonized by its related heterodimer, inhibin. For example, in the regulation of follicle-stimulating hormone (FSH) secretion from the pituitary, activin promotes FSH synthesis and secretion, while inhibin reduces FSH synthesis and secretion. Other proteins that may regulate activin bioactivity and/or bind to activin include follistatin (FS), follistatin-related protein (FSRP, also known as FLRG or FSTL3), and $\alpha_2$-macroglobulin.

As described herein, agents that bind to "activin A" are agents that specifically bind to the PA subunit, whether in the context of an isolated PA subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the PA subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a PA subunit, whether in the context of an isolated $\beta_A$ subunit or as a dimeric complex (e.g., a $\beta_A\beta_A$ homodimer or a $\beta_A\beta_B$ heterodimer). In the case of $\beta_A\beta_B$ heterodimers, agents that inhibit "activin A" are agents that specifically inhibit one or more activities of the PA subunit, but do not inhibit the activity of the non-$\beta_A$ subunit of the complex (e.g., the $\beta_B$ subunit of the complex). This principle applies also to agents that bind to and/or inhibit "activin B", "activin C", and "activin E". Agents disclosed herein that antagonize "activin AB" are agents that inhibit one or more activities as mediated by the PA subunit and one or more activities as mediated by the $\beta_B$ subunit. The same principle also applies to agent that bind to and/or inhibit "activin AC", "activin BC", "activin AE", and "activin BE".

The BMPs and GDFs together form a family of cysteine-knot cytokines sharing the characteristic fold of the TGF-beta superfamily [Rider et al. (2010) Biochem J., 429(1):1-12]. This family includes, for example, BMP2, BMP4, BMP6, BMP7, BMP2a, BMP3, BMP3b (also known as GDF10), BMP4, BMP5, BMP6, BMP7, BMP8, BMP8a, BMP8b, BMP9 (also known as GDF2), BMP10, BMP11 (also known as GDF11), BMP12 (also known as GDF7), BMP13 (also known as GDF6), BMP14 (also known as GDF5), BMP15, GDF1, GDF3 (also known as VGR2), GDF8 (also known as myostatin), GDF9, GDF15, and decapentaplegic. Besides the ability to induce bone formation, which gave the BMPs their name, the BMP/GDFs display morphogenetic activities in the development of a wide range of tissues. BMP/GDF homo- and hetero-dimers interact with combinations of type I and type II receptor dimers to produce multiple possible signaling complexes, leading to the activation of one of two competing sets of SMAD transcription factors. BMP/GDFs have highly specific and localized functions. These are regulated in a number of ways, including the developmental restriction of BMP/GDF expression and through the secretion of several specific BMP antagonist proteins that bind with high affinity to the cytokines. Curiously, a number of these antagonists resemble TGF-beta superfamily ligands.

As demonstrated herein, a soluble ALK4:ActRIIB heterodimer, which binds to various ligands including activin A, activin B, GDF11, GDF8, BMP6, GDF3, and BMP10, is effective in reducing the severity of muscle and bone loss in an SMA model. Moreover, ALK4:ActRIIB treatment increased muscle strength in SMA patients. While not wishing to be bound to any particular mechanism, it is expected that the effects of ALK4:ActRIIB heterodimers are caused primarily by a ALK4-ActRIIB signaling antagonist effect, particularly as mediated by one or more of activin A, activin B, GDF11, GDF8, BMP6, GDF3, and BMP10. Regardless of the mechanism, it is apparent from the data presented herein that ALK4:ActRIIB signaling antagonists do reduce the severity of muscle and bone loss as well as having other positivity effects in treating SMA. It should be noted that muscle and bone growth/loss are dynamic, with changes depending on a balance of factors that increase muscle/bone and factors that decrease muscle/bone. Muscle mass and bone density can be increased by increasing factors that increase muscle and bone growth; decreasing factors that inhibit muscle and bone growth; or both. The terms increasing muscle mass and bone density refer to the observable physical changes in bone and muscle tissues and are intended to be neutral as to the mechanism by which the changes occur.

The animal models for SMA that was used in the studies described herein are considered to be predicative of efficacy in humans, and therefore, this disclosure provides methods for using ALK4:ActRIIB heterodimer and other ALK4:ActRIIB antagonists to treat SMA, particularly preventing or delaying onset and/or reducing the severity or duration of one or more complications of SMA, in humans. As disclosed herein, the term ALK4:ActRIIB antagonist refers a variety of agents that may be used to antagonize ALK4-ActRIIB signaling including, for example, antagonists that inhibit one or more ligands [e.g., activin A, activin B, GDF11, GDF8, BMP6, GDF3, and BMP10]; antagonists that inhibit one or more type I- or type II-(e.g., ALK4 and ActRIIB); and antagonists that inhibit one or more downstream signaling components (e.g., Smad proteins such as Smads 2 and 3). ALK4:ActRIIB antagonists to be used in accordance with the methods and uses of the disclosure include a variety of forms, for example, ligand traps (e.g., ALK4:ActRIIB heteromultimers), antibody antagonists (e.g., antibodies that inhibit one or more of ALK4, ActRIIB, activin A, activin B, GDF11, GDF8, BMP6, GDF3, and BMP10), small molecule antagonists [e.g., small molecules that inhibit one or more of ALK4, ActRIIB, activin A, activin B, GDF11, GDF8, BMP6, GDF3, and BMP10 and one or more Smad proteins (e.g., Smads 2 and 3)], and nucleotide antagonists [e.g., nucleotide sequences that inhibit one or more of ALK4, ActRIIB, activin A, activin B, GDF11, GDF8, BMP6, GDF3, and BMP10 and one or more Smad proteins (e.g., Smads 2 and 3)].

The terms used in this specification generally have their ordinary meanings in the art, within the context of this disclosure and in the specific context where each term is used. Certain terms are discussed below or elsewhere in the specification to provide additional guidance to the practitioner in describing the compositions and methods of the disclosure and how to make and use them. The scope or meaning of any use of a term will be apparent from the specific context in which it is used.

The terms "heteromer" or "heteromultimer" refer to a protein complex comprising at least a first polypeptide chain and a second polypeptide chain, wherein the second polypeptide chain differs in amino acid sequence from the first polypeptide chain by at least one amino acid residue. The heteromer can comprise a "heterodimer" formed by the first and second polypeptide chains or can form higher order structures where one or more polypeptide chains in addition to the first and second polypeptide chains are present. Exemplary structures for the heteromultimer include heterodimers, heterotrimers, heterotetramers and further oligomeric structures. Heterodimers are designated herein as X:Y or equivalently as X-Y, where X represents a first polypeptide chain and Y represents a second polypeptide chain. Higher-order heteromers and oligomeric structures are designated herein in a corresponding manner. In certain embodiments a heteromultimer is recombinant (e.g., one or more polypeptide components may be a recombinant protein), isolated and/or purified.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," when modified with an adverb such as "highly," may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably <5-fold and more preferably <2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

2. ALK4:ActRIIB Heteromultimers

In certain aspects, the present disclosure relates to heteromultimers comprising one or more ALK4 receptor polypeptides (e.g., SEQ ID NOs: 9, 10, 19, 20, 42, 44, 47, 48, 74, and 76) and one or more ActRIIB receptor polypeptides (e.g., SEQ ID NOs: 1, 2, 3, 4, 5, 6, 39, 41, 45, 46, 70, 72, 78, and 80) which are generally referred to herein as "ALK4:ActRIIB heteromultimer complexes" or "ALK4:ActRIIB heteromultimers". Preferably, ALK4:ActRIIB heteromultimers of the disclosure are soluble, for example, a heteromultimer may comprises a soluble portion (domain) of an ALK4 receptor and a soluble portion (domain) of an ActRIIB receptor. In general, the extracellular domains of ALK4 and ActRIIB correspond to a soluble portion of these receptors. Therefore, in some embodiments, heteromultimers of the disclosure comprise an extracellular domain of an ALK4 receptor and an extracellular domain of an ActRIIB receptor. Example extracellular domains ALK4 and ActRIIB receptors are disclosed herein and such sequences, as well as fragments, functional variants, and modified forms thereof, may be used in accordance with the inventions of the disclosure (e.g., ALK4:ActRIIB heteromultimer compositions and uses thereof). ALK4:ActRIIB heteromultimers of the disclosure include, e.g., heterodimers, heterotrimers, heterotetramers and higher order oligomeric structures. See, e.g., FIG. 6. In certain preferred embodiments, heteromultimers of the disclosure are ALK4:ActRIIB heterodimers.

Preferably, ALK4:ActRIIB heteromultimers of the disclosure bind to one or more TGF-beta superfamily ligands. In some embodiments, ALK4:ActRIIB heteromultimers may bind to one or more of activin (e.g., activin A, activin B, activin C, activin E, activin AC, activin AB, activin BC, activin AE, and activin BE), GDF8, GDF11, BMP6, GDF3, and BMP10. In some embodiments, ALK4:ActRIIB heteromultimers bind to activin A. In some embodiments, ALK4:ActRIIB heteromultimers bind to activin B. In some embodiments, ALK4:ActRIIB heteromultimers bind to activin C. In some embodiments, ALK4:ActRIIB heteromultimers bind to activin E. In some embodiments, ALK4:ActRIIB heteromultimers bind to activin AB. In some embodiments, ALK4:ActRIIB heteromultimers bind to activin AC. In some embodiments, ALK4:ActRIIB heteromultimers bind to activin AE. In some embodiments, ALK4:ActRIIB heteromultimers bind to activin BC. In some embodiments, ALK4:ActRIIB heteromultimers bind to activin BE. In some embodiments, ALK4:ActRIIB heteromultimers bind to GDF11. In some embodiments, ALK4:ActRIIB heteromultimers bind to GDF8. In some embodiments, ALK4:ActRIIB heteromultimers bind to BMP6. In some embodiments, ALK4:ActRIIB heteromultimers bind to GDF3. In some embodiments, ALK4:ActRIIB heteromultimers bind to BMP10. In some embodiments, ALK4:ActRIIB heteromultimers do not bind to, or no not substantially bind to BMP9 (e.g., have indeterminate $K_a$ or $K_d$ due to the transient nature of the interaction between BMP9 and an ALK4:ActRIIB heteromultimer). In some embodiments, ALK4:ActRIIB heteromultimers binds with stronger affinity to activin B compared to a corresponding ActRIIB homomultimer. In some embodiments, ALK4:ActRIIB heteromultimers binds with weaker affinity to GDF3 compared to a corresponding ActRIIB homomultimer. In some embodiments, ALK4:ActRIIB heteromultimers binds with weaker affinity to BMP9 compared to a corresponding ActRIIB homomultimer. In some embodiments, ALK4:ActRIIB heteromultimers binds with weaker affinity to BMP10 compared to a corresponding ActRIIB homomultimer. Optionally, ALK4:ActRIIB heteromultimers may further bind to one or more of BMP2, BMP2/7, BMP3, BMP4, BMP4/7, BMP5, BMP7, BMP8a, BMP8b, GDF5, GDF6/BMP13, GDF7, GDF9b/BMP15, GDF15/MIC1, TGF-β1, TGF-β2, TGF-β3, nodal, glial cell-derived neurotrophic factor (GDNF), neurturin, artemin, persephin, MIS, and Lefty.

In some embodiments, ALK4:ActRIIB heteromultimers may be used to inhibit (antagonize) signaling (e.g., Smad 2/3 and/or Smad 1/5/8 signaling) mediated by one or more TGFβ superfamily ligands. In particular, ALK4:ActRIIB heteromultimers of the disclosure may be used to inhibit intracellular signaling by one or more TGFβ superfamily ligands in, for example, a cell-based assay such as those described herein. For example, ALK4:ActRIIB heteromultimers may inhibit signaling mediated by one or more of activin (e.g., activin A, activin B, activin C, activin E, activin AC, activin AB, activin BC, activin AE, and activin BE), GDF8, GDF11, BMP6, GDF3, and BMP10 in a cell-based assay. In some embodiments, ALK4:ActRIIB heteromultimers may inhibit activin A signaling in a cell-based assay. In some embodiments, ALK4:ActRIIB heteromultimers may inhibit activin B signaling in a cell-based assay. In some embodiments, ALK4:ActRIIB heteromultimers may inhibit activin C signaling in a cell-based assay. In some embodiments, ALK4:ActRIIB heteromultimers may inhibit activin D signaling in a cell-based assay. In some embodiments, ALK4:ActRIIB heteromultimers may inhibit activin E signaling in a cell-based assay. In some embodiments, ALK4:ActRIIB heteromultimers may inhibit activin AB signaling in a cell-based assay. In some embodiments, ALK4:ActRIIB heteromultimers may inhibit activin AC signaling in a cell-based assay. In some embodiments, ALK4:ActRIIB heteromultimers may inhibit activin BC signaling in a cell-based assay. In some embodiments, ALK4:ActRIIB heteromultimers may inhibit activin AE signaling in a cell-based assay. In some embodiments, ALK4:ActRIIB heteromultimers may inhibit activin BE signaling in a cell-based assay. In some embodiments, ALK4:ActRIIB heteromultimers may inhibit GDF11 signaling in a cell-based assay. In some embodiments, ALK4:ActRIIB heteromultimers may inhibit GDF8 signaling in a cell-based assay. In some embodiments, ALK4:ActRIIB heteromultimers may inhibit BMP6 signaling in a cell-based assay. In some embodiments, ALK4:ActRIIB heteromultimers may inhibit GDF3 signaling in a cell-based assay. In some embodiments, ALK4:ActRIIB heteromultimers may inhibit BMP9 signaling in a cell-based assay. In some embodiments, ALK4:ActRIIB heteromultimers do not inhibit, or do not substantially inhibit BMP9 signaling in a cell-based assay. In some embodiments, ALK4:ActRIIB heteromultimers are stronger inhibitors of activin B signaling in a cell-based assay compared to a corresponding ActRIIB homomultimer. In some embodiments, ALK4:ActRIIB heteromultimers are weaker inhibitors of BMP10 signaling in a cell-based assay compared to a corresponding ActRIIB homomultimer. In some embodiments, ALK4:ActRIIB heteromultimers are stronger inhibitors of GDF3 signaling in a cell-based assay compared to a corresponding ActRIIB homomultimer. In some embodiments, ALK4:ActRIIB heteromultimers are stronger inhibitors of BMP9 signaling in a cell-based assay compared to a corresponding ActRIIB homomultimer. Optionally, ALK4:ActRIIB heteromultimers may further inhibit intracellular signaling by one or more of BMP2, BMP2/7, BMP3, BMP4, BMP4/7, BMP5, BMP7, BMP8a, BMP8b, GDF5, GDF6/BMP13, GDF7, GDF9b/BMP15, GDF15/MIC1, TGF-β1, TGF-β2, TGF-β3, nodal, glial cell-derived neurotrophic factor (GDNF), neurturin, artemin, persephin, MIS, and Lefty in a cell-based assay.

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIB polypeptides are provided throughout the present disclosure as well as in International Patent Application Publication Nos. WO 2006/012627, WO 2008/097541, and WO 2010/151426, which are incorporated herein by reference in their entirety. Numbering of amino acids for all ActRIIB-related polypeptides described herein is based on the numbering of the human ActRIIB precursor protein sequence provided below (SEQ ID NO: 1), unless specifically designated otherwise.

The human ActRIIB precursor protein sequence is as follows:

(SEQ ID NO: 1)

```
  1 MTAPWVALAL LWGSLCAGSG RGEAETRECI YYNANWELER TNQSGLERCE
 51 GEQDKRLHCY ASWRNSSGTI ELVKKGCWLD DFNCYDRQEC VATEENPQVY
101 FCCCEGNFCN ERFTHLPEAG GPEVTYEPPP TAPTLLTVLA YSLLPIGGLS
151 LIVLLAFWMY RHRKPPYGHV DIHEDPGPPP PSPLVGLKPL QLLEIKARGR
201 FGCVWKAQLM NDFVAVKIFP LQDKQSWQSE REIFSTPGMK HENLLQFIAA
251 EKRGSNLEVE LWLITAFHDK GSLTDYLKGN IITWNELCHV AETMSRGLSY
301 LHEDVPWCRG EGHKPSIAHR DFKSKNVLLK SDLTAVLADF GLAVRFEPGK
351 PPGDTHGQVG TRRYMAPEVL EGAINFQRDA FLRIDMYAMG LVLWELVSRC
401 KAADGPVDEY MLPFEEEIGQ HPSLEELQEV VVHKKMRPTI KDHWLKHPGL
451 AQLCVTIEEC WDHDAEARLS AGCVEERVSL IRRSVNGTTS DCLVSLVTSV
501 TNVDLPPKES SI
```

The signal peptide is indicated with a single underline; the extracellular domain is indicated in bold font; and the potential, endogenous N-linked glycosylation sites are indicated with a doubleunderline.

The processed extracellular ActRIIB polypeptide sequence is as follows:

(SEQ ID NO: 2)
GRGEAETRECIYYNANWELERTNQSGLERCEGEQDKRLHCYASWRNSSGTI

ELVKKGCWLDDFNCYDRQECVATEENPQVYFCCCEGNFCNERFTHLPEAGG

PEVTYEPPPTAPT

In some embodiments, the protein may be produced with an "SGR . . . " sequence at the N-terminus. The C-terminal "tail" of the extracellular domain is indicated by a single underline. The sequence with the "tail" deleted (a Δ15 sequence) is as follows:

(SEQ ID NO: 3)
GRGEAETRECIYYNANWELERTNQSGLERCEGEQDKRLHCYASWRNSSGTI

ELVKKGCWLDDFNCYDRQECVATEENPQVYFCCCEGNFCNERFTHLPEA

A form of ActRIIB with an alanine at position 64 of SEQ ID NO: 1 (A64) is also reported in the literature See, e.g., Hilden et al. (1994) Blood, 83(8): 2163-2170. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

The form of ActRIIB with an alanine at position 64 is as follows:

(SEQ ID NO: 4)
1 MTAPWVALAL LWGSLCAGSG RGEAETRECI YYNANWELER TNQSGLERCE

51 GEQDKRLHCY ASWANSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI

The signal peptide is indicated by single underline and the extracellular domain is indicated by bold font.

The processed extracellular ActRIIB polypeptide sequence of the alternative A64 form is as follows:

(SEQ ID NO: 5)

GRGEAETRECIYYNANWELERTNQSGLERCEGEQDKRLHCYASWANSSGTI

ELVKKGCWLDDFNCYDRQECVATEENPQVYFCCCEGNFCNERFTHLPEAGG

PEVTYEPPPTAPT

In some embodiments, the protein may be produced with an "SGR . . . " sequence at the N-terminus. The C-terminal "tail" of the extracellular domain is indicated by single underline. The sequence with the "tail" deleted (a Δ15 sequence) is as follows:

(SEQ ID NO: 6)

GRGEAETRECIYYNANWELERTNQSGLERCEGEQDKRLHCYASWANSSGTI

ELVKKGCWLDDFNCYDRQECVATEENPQVYFCCCEGNFCNERFTHLPEA

A nucleic acid sequence encoding the human ActRIIB precursor protein is shown below (SEQ ID NO: 7), representing nucleotides 25-1560 of Genbank Reference Sequence NM_001106.3, which encode amino acids 1-513 of the ActRIIB precursor. The sequence as shown provides an arginine at position 64 and may be modified to provide an alanine instead. The signal sequence is underlined.

(SEQ ID NO: 7)

```
   1 ATGACGGCGC CCTGGGTGGC CCTCGCCCTC CTCTGGGGAT CGCTGTGCGC

  51 CGGCTCTGGG CGTGGGGAGG CTGAGACACG GGAGTGCATC TACTACAACG

 101 CCAACTGGGA GCTGGAGCGC ACCAACCAGA GCGGCCTGGA GCGCTGCGAA

 151 GGCGAGCAGG ACAAGCGGCT GCACTGCTAC GCCTCCTGGC GCAACAGCTC

 201 TGGCACCATC GAGCTCGTGA AGAAGGGCTG CTGGCTAGAT GACTTCAACT

 251 GCTACGATAG GCAGGAGTGT GTGGCCACTG AGGAGAACCC CCAGGTGTAC

 301 TTCTGCTGCT GTGAAGGCAA CTTCTGCAAC GAACGCTTCA CTCATTTGCC

 351 AGAGGCTGGG GGCCCGGAAG TCACGTACGA GCCACCCCCG ACAGCCCCCA

 401 CCCTGCTCAC GGTGCTGGCC TACTCACTGC TGCCCATCGG GGGCCTTTCC

 451 CTCATCGTCC TGCTGGCCTT TTGGATGTAC CGGCATCGCA AGCCCCCCTA

 501 CGGTCATGTG GACATCCATG AGGACCCTGG GCCTCCACCA CCATCCCCTC

 551 TGGTGGGCCT GAAGCCACTG CAGCTGCTGG AGATCAAGGC TCGGGGGCGC

 601 TTTGGCTGTG TCTGGAAGGC CCAGCTCATG AATGACTTTG TAGCTGTCAA

 651 GATCTTCCCA CTCCAGGACA AGCAGTCGTG GCAGAGTGAA CGGGAGATCT

 701 TCAGCACACC TGGCATGAAG CACGAGAACC TGCTACAGTT CATTGCTGCC

 751 GAGAAGCGAG GCTCCAACCT CGAAGTAGAG CTGTGGCTCA TCACGGCCTT

 801 CCATGACAAG GGCTCCCTCA CGGATTACCT CAAGGGGAAC ATCATCACAT

 851 GGAACGAACT GTGTCATGTA GCAGAGACGA TGTCACGAGG CCTCTCATAC

 901 CTGCATGAGG ATGTGCCCTG GTGCCGTGGC GAGGGCCACA AGCCGTCTAT

 951 TGCCCACAGG GACTTTAAAA GTAAGAATGT ATTGCTGAAG AGCGACCTCA

1001 CAGCCGTGCT GGCTGACTTT GGCTTGGCTG TTCGATTTGA GCCAGGGAAA

1051 CCTCCAGGGG ACACCCACGG ACAGGTAGGC ACGAGACGGT ACATGGCTCC

1101 TGAGGTGCTC GAGGGAGCCA TCAACTTCCA GAGAGATGCC TTCCTGCGCA

1151 TTGACATGTA TGCCATGGGG TTGGTGCTGT GGGAGCTTGT GTCTCGCTGC

1201 AAGGCTGCAG ACGGACCCGT GGATGAGTAC ATGCTGCCCT TTGAGGAAGA

1251 GATTGGCCAG CACCCTTCGT TGGAGGAGCT GCAGGAGGTG GTGGTGCACA

1301 AGAAGATGAG GCCCACCATT AAAGATCACT GGTTGAAACA CCCGGGCCTG
```

-continued

```
1351   GCCCAGCTTT GTGTGACCAT CGAGGAGTGC TGGGACCATG ATGCAGAGGC

1401   TCGCTTGTCC GCGGGCTGTG TGGAGGAGCG GGTGTCCCTG ATTCGGAGGT

1451   CGGTCAACGG CACTACCTCG GACTGTCTCG TTTCCCTGGT GACCTCTGTC

1501   ACCAATGTGG ACCTGCCCCC TAAAGAGTCA AGCATC
```

A nucleic acid sequence encoding processed extracellular human ActRIIB polypeptide is as follows (SEQ ID NO: 8). The sequence as shown provides an arginine at position 64, and may be modified to provide an alanine instead.

```
                                           (SEQ ID NO: 8)
  1   GGGCGTGGGG AGGCTGAGAC ACGGGAGTGC ATCTACTACA ACGCCAACTG

 51   GGAGCTGGAG CGCACCAACC AGAGCGGCCT GGAGCGCTGC GAAGGCGAGC

101   AGGACAAGCG GCTGCACTGC TACGCCTCCT GGCGCAACAG CTCTGGCACC

151   ATCGAGCTCG TGAAGAAGGG CTGCTGGCTA GATGACTTCA ACTGCTACGA

201   TAGGCAGGAG TGTGTGGCCA CTGAGGAGAA CCCCCAGGTG TACTTCTGCT

251   GCTGTGAAGG CAACTTCTGC AACGAACGCT TCACTCATTT GCCAGAGGCT

301   GGGGGCCCGG AAGTCACGTA CGAGCCACCC CCGACAGCCC CCACC
```

An alignment of the amino acid sequences of human ActRIIB extracellular domain and human ActRIIA extracellular domain are illustrated in FIG. 1. This alignment indicates amino acid residues within both receptors that are believed to directly contact ActRII ligands. For example, the composite ActRII structures indicated that the ActRIIB-ligand binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated.

In addition, ActRIIB is well-conserved among vertebrates, with large stretches of the extracellular domain completely conserved. For example, FIG. 2 depicts a multi-sequence alignment of a human ActRIIB extracellular domain compared to various ActRIIB orthologs. Many of the ligands that bind to ActRIIB are also highly conserved. Accordingly, from these alignments, it is possible to predict key amino acid positions within the ligand-binding domain that are important for normal ActRIIB-ligand binding activities as well as to predict amino acid positions that are likely to be tolerant of substitution without significantly altering normal ActRIIB-ligand binding activities. Therefore, an active, human ActRIIB variant polypeptide useful in accordance with the presently disclosed methods may include one or more amino acids at corresponding positions from the sequence of another vertebrate ActRIIB, or may include a residue that is similar to that in the human or other vertebrate sequences. Without meaning to be limiting, the following examples illustrate this approach to defining an active ActRIIB variant. L46 in the human extracellular domain (SEQ ID NO: 53) is a valine in *Xenopus* ActRIIB (SEQ ID NO: 55), and so this position may be altered, and optionally may be altered to another hydrophobic residue, such as V, I or F, or a non-polar residue such as A. E52 in the human extracellular domain is a K in *Xenopus*, indicating that this site may be tolerant of a wide variety of changes, including polar residues, such as E, D, K, R, H, S, T, P, G, Y and probably A. T93 in the human extracellular domain is a K in *Xenopus*, indicating that a wide structural variation is tolerated at this position, with polar residues favored, such as S, K, R, E, D, H, G, P, G and Y. F108 in the human extracellular domain is a Y in *Xenopus*, and therefore Y or other hydrophobic group, such as I, V or L should be tolerated. E111 in the human extracellular domain is K in *Xenopus*, indicating that charged residues will be tolerated at this position, including D, R, K and H, as well as Q and N. R112 in the human extracellular domain is K in *Xenopus*, indicating that basic residues are tolerated at this position, including R and H. A at position 119 in the human extracellular domain is relatively poorly conserved, and appears as P in rodents and V in *Xenopus*, thus essentially any amino acid should be tolerated at this position.

Moreover, ActRII proteins have been characterized in the art in terms of structural and functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide amply guidance for how to generate ActRIIB variants that retain one or more normal activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIB, as demarcated by the outermost of these conserved cysteines, corresponds to positions 29-109 of SEQ ID NO: 1 (ActRIIB precursor). Thus, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, or 28 residues at the N-terminus and/or by about 1, 2, 3, 4, 5, 6, 7, 8, 9, 10, 11, 12, 13, 14, 15, 16, 17, 18, 19, 20, 21, 22, 23, 24, or 25 residues at the C-terminus without necessarily altering ligand binding. Exemplary ActRIIB extracellular domains for N-terminal and/or C-terminal truncation include SEQ ID NOs: 2, 3, 5, and 6.

Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO: 1, "ActRIIB(20-119)-Fc", has reduced binding to GDF11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar, but somewhat reduced activity, relative to the wild-type, even though the proline knot region is disrupted.

Thus, ActRIIB extracellular domains that stop at amino acid 134, 133, 132, 131, 130 and 129 (with respect to SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, it is known in the art that mutations of P129 and P130 (with respect to SEQ ID NO: 1) do not substantially decrease ligand binding. Therefore, an ActRIIB polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO:1) is poorly conserved and so is readily altered or truncated. ActRIIB polypeptides ending at 128 (with respect to SEQ ID NO: 1) or later should retain ligand-binding activity. ActRIIB polypeptides ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to SEQ ID NO: 1) will retain ligand-binding activity. Amino acid 29 represents the initial cysteine. An alanine-to-asparagine mutation at position 24 (with respect to SEQ ID NO: 1) introduces an N-linked glycosylation sequence without substantially affecting ligand binding [U.S. Pat. No. 7,842,663]. This confirms that mutations in the region between the signal cleavage peptide and the cysteine cross-linked region, corresponding to amino acids 20-29, are well tolerated. In particular, ActRIIB polypeptides beginning at position 20, 21, 22, 23, and 24 (with respect to SEQ ID NO: 1) should retain general ligand-biding activity, and ActRIIB polypeptides beginning at positions 25, 26, 27, 28, and 29 (with respect to SEQ ID NO: 1) are also expected to retain ligand-biding activity. It has been demonstrated, e.g., U.S. Pat. No. 7,842,663, that, surprisingly, an ActRIIB construct beginning at 22, 23, 24, or 25 will have the most activity.

Taken together, a general formula for an active portion (e.g., ligand-binding portion) of ActRIIB comprises amino acids 29-109 of SEQ ID NO: 1. Therefore ActRIIB polypeptides may, for example, comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to any one of amino acids 20-29 (e.g., beginning at any one of amino acids 20, 21, 22, 23, 24, 25, 26, 27, 28, or 29) of SEQ ID NO: 1 and ending at a position corresponding to any one amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. Other examples include polypeptides that begin at a position from 20-29 (e.g., any one of positions 20, 21, 22, 23, 24, 25, 26, 27, 28, or 29) or 21-29 (e.g., any one of positions 21, 22, 23, 24, 25, 26, 27, 28, or 29) of SEQ ID NO: 1 and end at a position from 119-134 (e.g., any one of positions 119, 120, 121, 122, 123, 124, 125, 126, 127, 128, 129, 130, 131, 132, 133, or 134), 119-133 (e.g., any one of positions 119, 120, 121, 122, 123, 124, 125, 126, 127, 128, 129, 130, 131, 132, or 133), 129-134 (e.g., any one of positions 129, 130, 131, 132, 133, or 134), or 129-133 (e.g., any one of positions 129, 130, 131, 132, or 133) of SEQ ID NO: 1. Other examples include constructs that begin at a position from 20-24 (e.g., any one of positions 20, 21, 22, 23, or 24), 21-24 (e.g., any one of positions 21, 22, 23, or 24), or 22-25 (e.g., any one of positions 22, 22, 23, or 25) of SEQ ID NO: 1 and end at a position from 109-134 (e.g., any one of positions 109, 110, 111, 112, 113, 114, 115, 116, 117, 118, 119, 120, 121, 122, 123, 124, 125, 126, 127, 128, 129, 130, 131, 132, 133, or 134), 119-134 (e.g., any one of positions 119, 120, 121, 122, 123, 124, 125, 126, 127, 128, 129, 130, 131, 132, 133, or 134) or 129-134 (e.g., any one of positions 129, 130, 131, 132, 133, or 134) of SEQ ID NO: 1. Variants within these ranges are also contemplated, particularly those having at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 1.

The variations described herein may be combined in various ways. In some embodiments, ActRIIB variants comprise no more than 1, 2, 5, 6, 7, 8, 9, 10 or 15 conservative amino acid changes in the ligand-binding pocket, and zero, one, or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO: 1). An asparagine-to-alanine alteration at position 65 (N65A) actually improves ligand binding in the A64 background, and is thus expected to have no detrimental effect on ligand binding in the R64 background [U.S. Pat. No. 7,842,663]. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64 [U.S. Pat. No. 7,842,663]. Additionally, the results of the mutagenesis program described in the art indicate that there are amino acid positions in ActRIIB that are often beneficial to conserve. With respect to SEQ ID NO: 1, these include position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, the disclosure provides a framework of amino acids that may be conserved in ActRIIB polypeptides. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

In certain embodiments, the disclosure relates to heteromultimers that comprise at least one ActRIIB polypeptide, which includes fragments, functional variants, and modified forms thereof. Preferably, ActRIIB polypeptides for use in accordance with inventions of the disclosure are soluble (e.g., an extracellular domain of ActRIIB) In other preferred embodiments, ActRIIB polypeptides for use in accordance with the disclosure bind to one or more TGF-beta superfamily ligands. Therefore, in some embodiments, ActRIIB polypeptides for use in accordance with the disclosure inhibit (antagonize) activity (e.g., inhibition of Smad signaling) of one or more TGF-beta superfamily ligands. In some embodiments, heteromultimers of the disclosure comprise at least one ActRIIB polypeptide that comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to amino acids 20-29 (e.g., beginning at any one of amino acids 20, 21, 22, 23, 24, 25, 26, 27, 28, or 29) of SEQ ID NO: 1 and ending at a position corresponding to amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In certain preferred embodiments, heteromultimers of the disclosure comprise at least one ActRIIB polypeptide that comprises, consists, or consists essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1 In other preferred embodiments, heteromultimer complexes of the disclosure comprise at least one ActRIIB polypeptide that comprises, consists of, or consists essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1. In some embodiments, heteromultimers of the disclosure comprise at least one ActRIIB polypeptide that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 39, 41, 45, or 46. In certain preferred embodiments, heteromultimers of the disclosure comprise do not comprise an ActRIIB polypeptide wherein the position corresponding to L79 of SEQ ID NO: 1 is an acidic amino acid (i.e., is not a naturally occurring D or E amino acid residue or artificial acidic amino acid).

In certain aspects, the present disclosure relates to protein complexes that comprise an ALK4 polypeptide. As used herein, the term "ALK4" refers to a family of activin receptor-like kinase-4 proteins from any species and variants derived from such ALK4 proteins by mutagenesis or other modification. Reference to ALK4 herein is understood to be a reference to any one of the currently identified forms. Members of the ALK4 family are generally transmembrane proteins, composed of a ligand-binding extracellular domain with a cysteine-rich region, a transmembrane domain, and a cytoplasmic domain with predicted serine/threonine kinase activity.

The term "ALK4 polypeptide" includes polypeptides comprising any naturally occurring polypeptide of an ALK4 family member as well as any variants thereof (including mutants, fragments, fusions, and peptidomimetic forms) that retain a useful activity. Numbering of amino acids for all ALK4-related polypeptides described herein is based on the numbering of the human ALK4 precursor protein sequence below (SEQ ID NO: 9), unless specifically designated otherwise.

A human ALK4 precursor protein sequence (NCBI Ref Seq NP_004293) is as follows:

(SEQ ID NO: 9)

1 MAESAGASSF FPLVVLLLAG SGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK DNGTWTQLWL VSDYHEHGSL FDYLNRYTVT

301 IEGMIKLALS AASGLAHLHM EIVGTQGKPG IAHRDLKSKN ILVKKNGMCA IADLGLAVRH

361 DAVTDTIDIA PNQRVGTKRY MAPEVLDETI NMKHFDSFKC ADIYALGLVY WEIARRCNSG

421 GVHEEYQLPY YDLVPSDPSI EEMRKVVCDQ KLRPNIPNWW QSYEALRVMG KMMRECWYAN

481 GAARLTALRI KKTLSQLSVQ EDVKI

The signal peptide is indicated by a single underline and the extracellular domain is indicated in bold font.

A processed extracellular human ALK4 polypeptide sequence is as follows:

(SEQ ID NO: 10)

SGPRGVQALLCACTSCLQANYTCETDGACMVSIFNLDGMEHHVRTCIPKVE

LVPAGKPFYCLSSEDLRNTHCCYTDYCNRIDLRVPSGHLKEPEHPSMWGPV

E

A nucleic acid sequence encoding the ALK4 precursor protein is shown below (SEQ ID NO: 11), corresponding to nucleotides 78-1592 of Genbank Reference Sequence NM_004302.4. The signal sequence is underlined and the extracellular domain is indicated in bold font.

(SEQ ID NO: 11)

ATGGCGGAGTCGGCCGGAGCCTCCTCCTTCTTCCCCCTTGTTGTCCTCCTG

CTCGCCGGCAGCGGCGGGTCCGGGCCCCGGGGGGTCCAGGCTCTGCTGTGT

GCGTGCACCAGCTGCCTCCAGGCCAACTACACGTGTGAGACAGATGGGGCC

TGCATGGTTTCCATTTTCAATCTGGATGGGATGGAGCACCATGTGCGCACC

-continued

TGCATCCCCAAAGTGGAGCTGGTCCCTGCCGGGAAGCCCTTCTACTGCCTG
AGCTCGGAGGACCTGCGCAACACCCACTGCTGCTACACTGACTACTGCAAC
AGGATCGACTTGAGGGTGCCCAGTGGTCACCTCAAGGAGCCTGAGCACCCG
TCCATGTGGGGCCCGGTGGAGCTGGTAGGCATCATCGCCGGCCCGGTGTTC
CTCCTGTTCCTCATCATCATCATTGTTTTCCTTGTCATTAACTATCATCAG
CGTGTCTATCACAACCGCCAGAGACTGGACATGGAAGATCCCTCATGTGAG
ATGTGTCTCTCCAAAGACAAGACGCTCCAGGATCTTGTCTACGATCTCTCC
ACCTCAGGGTCTGGCTCAGGGTTACCCCTCTTTGTCCAGCGCACAGTGGCC
CGAACCATCGTTTTACAAGAGATTATTGGCAAGGGTCGGTTTGGGGAAGTA
TGGCGGGGCCGCTGGAGGGGTGGTGATGTGGCTGTGAAAATATTCTCTTCT
CGTGAAGAACGGTCTTGGTTCAGGGAAGCAGAGATATACCAGACGGTCATG
CTGCGCCATGAAAACATCCTTGGATTTATTGCTGCTGACAATAAAGATAAT
GGCACCTGGACACAGCTGTGGCTTGTTTCTGACTATCATGAGCACGGGTCC
CTGTTTGATTATCTGAACCGGTACACAGTGACAATTGAGGGGATGATTAAG
CTGGCCTTGTCTGCTGCTAGTGGGCTGGCACACCTGCACATGGAGATCGTG
GGCACCCAAGGGAAGCCTGGAATTGCTCATCGAGACTTAAAGTCAAAGAAC
ATTCTGGTGAAGAAAAATGGCATGTGTGCCATAGCAGACCTGGGCCTGGCT
GTCCGTCATGATGCAGTCACTGACACCATTGACATTGCCCCGAATCAGAGG
GTGGGGACCAAACGATACATGGCCCCTGAAGTACTTGATGAAACCATTAAT

-continued

ATGAAACACTTTGACTCCTTTAAATGTGCTGATATTTATGCCCTCGGGCTT
GTATATTGGGAGATTGCTCGAAGATGCAATTCTGGAGGAGTCCATGAAGAA
TATCAGCTGCCATATTACGACTTAGTGCCCTCTGACCCTTCCATTGAGGAA
ATGCGAAAGGTTGTATGTGATCAGAAGCTGCGTCCCAACATCCCCAACTGG
TGGCAGAGTTATGAGGCACTGCGGGTGATGGGGAAGATGATGCGAGAGTGT
TGGTATGCCAACGGCGCAGCCCGCCTGACGGCCCTGCGCATCAAGAAGACC
CTCTCCCAGCTCAGCGTGCAGGAAGACGTGAAGATC

A nucleic acid sequence encoding an extracellular ALK4 polypeptide is as follows:

(SEQ ID NO: 12)
TCCGGGCCCCGGGGGGTCCAGGCTCTGCTGTGTGCGTGCACCAGCTGCCTC
CAGGCCAACTACACGTGTGAGACAGATGGGGCCTGCATGGTTTCCATTTTC
AATCTGGATGGGATGGAGCACCATGTGCGCACCTGCATCCCCAAAGTGGAG
CTGGTCCCTGCCGGGAAGCCCTTCTACTGCCTGAGCTCGGAGGACCTGCGC
AACACCCACTGCTGCTACACTGACTACTGCAACAGGATCGACTTGAGGGTG
CCCAGTGGTCACCTCAAGGAGCCTGAGCACCCGTCCATGTGGGGCCCGGTG
GAG

An alternative isoform of human ALK4 precursor protein sequence, isoform C (NCBI Ref Seq NP_064733.3), is as follows:

(SEQ ID NO: 19)
1 MAESAGASSF FPLVVLLLAG SGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK ADCSFLTLPW EVVMVSAAPK LRSLRLQYKG

301 GRGRARFLFP LNNGTWTQLW LVSDYHEHGS LFDYLNRYTV TIEGMIKLAL SAASGLAHLH

361 MEIVGTQGKP GIAHRDLKSK NILVKKNGMC AIADLGLAVR HDAVTDTIDI APNQRVGTKR

421 YMAPEVLDET INMKHFDSFK CADIYALGLV YWEIARRCNS GGVHEEYQLP YYDLVPSDPS

481 IEEMRKVVCD QKLRPNIPNW WQSYEALRVM GKMMRECWYA NGAARLTALR IKKTLSQLSV

541 QEDVKI

The signal peptide is indicated by a single underline and the extracellular domain is indicated in bold font.

A processed extracellular ALK4 polypeptide sequence (isoform C) is as follows:

(SEQ ID NO: 20)
SGPRGVQALLCACTSCLQANYTCETDGACMVSIFNLDGMEHHVRTCIPKVE

LVPAGKPFYCLSSEDLRNTHCCYTDYCNRIDLRVPSGHLKEPEHPSMWGPV

E

A nucleic acid sequence encoding the ALK4 precursor protein (isoform C) is shown below (SEQ ID NO: 21), corresponding to nucleotides 78-1715 of Genbank Reference Sequence NM_020328.3. The signal sequence is underlined and the extracellular domain is indicated in bold font.

(SEQ ID NO: 21)
ATGGCGGAGTCGGCCGGAGCCTCCTCCTTCTTCCCCCTTGTTGTCCTCCTG

CTCGCCGGCAGCGGCGGGTCCGGGCCCCGGGGGGTCCAGGCTCTGCTGTGT

GCGTGCACCAGCTGCCTCCAGGCCAACTACACGTGTGAGACAGATGGGGCC

TGCATGGTTTCCATTTTCAATCTGGATGGGATGGAGCACCATGTGCGCACC

TGCATCCCCAAAGTGGAGCTGGTCCCTGCCGGGAAGCCCTTCTACTGCCTG

AGCTCGGAGGACCTGCGCAACACCCACTGCTGCTACACTGACTACTGCAAC

AGGATCGACTTGAGGGTGCCCAGTGGTCACCTCAAGGAGCCTGAGCACCCG

TCCATGTGGGGCCCGGTGGAGCTGGTAGGCATCATCGCCGGCCCGGTGTTC

CTCCTGTTCCTCATCATCATCATTGTTTTCCTTGTCATTAACTATCATCAG

CGTGTCTATCACAACCGCCAGAGACTGGACATGGAAGATCCCTCATGTGAG

ATGTGTCTCTCCAAAGACAAGACGCTCCAGGATCTTGTCTACGATCTCTCC

ACCTCAGGGTCTGGCTCAGGGTTACCCCTCTTTGTCCAGCGCACAGTGGCC

CGAACCATCGTTTTACAAGAGATTATTGGCAAGGGTCGGTTTGGGGAAGTA

TGGCGGGGCCGCTGGAGGGGTGGTGATGTGGCTGTGAAAATATTCTCTTCT

CGTGAAGAACGGTCTTGGTTCAGGGAAGCAGAGATATACCAGACGGTCATG

CTGCGCCATGAAAACATCCTTGGATTTATTGCTGCTGACAATAAAGCAGAC

TGCTCATTCCTCACATTGCCATGGGAAGTTGTAATGGTCTCTGCTGCCCCC

AAGCTGAGGAGCCTTAGACTCCAATACAAGGGAGGAAGGGGAAGAGCAAGA

TTTTTATTCCCACTGAATAATGGCACCTGGACACAGCTGTGGCTTGTTTCT

GACTATCATGAGCACGGGTCCCTGTTTGATTATCTGAACCGGTACACAGTG

ACAATTGAGGGGATGATTAAGCTGGCCTTGTCTGCTGCTAGTGGGCTGGCA

CACCTGCACATGGAGATCGTGGGCACCCAAGGGAAGCCTGGAATTGCTCAT

CGAGACTTAAAGTCAAAGAACATTCTGGTGAAGAAAAATGGCATGTGTGCC

ATAGCAGACCTGGGCCTGGCTGTCCGTCATGATGCAGTCACTGACACCATT

GACATTGCCCCGAATCAGAGGGTGGGGACCAAACGATACATGGCCCCTGAA

GTACTTGATGAAACCATTAATATGAAACACTTTGACTCCTTTAAATGTGCT

GATATTTATGCCCTCGGGCTTGTATATTGGGAGATTGCTCGAAGATGCAAT

TCTGGAGGAGTCCATGAAGAATATCAGCTGCCATATTACGACTTAGTGCCC

TCTGACCCTTCCATTGAGGAAATGCGAAAGGTTGTATGTGATCAGAAGCTG

-continued

CGTCCCAACATCCCCAACTGGTGGCAGAGTTATGAGGCACTGCGGGTGATG

GGGAAGATGATGCGAGAGTGTTGGTATGCCAACGGCGCAGCCCGCCTGACG

GCCCTGCGCATCAAGAAGACCCTCTCCCAGCTCAGCGTGCAGGAAGACGTG

AAGATC

A nucleic acid sequence encoding an extracellular ALK4 polypeptide (isoform C) is as follows:

(SEQ ID NO: 22)
TCCGGGCCCCGGGGGGTCCAGGCTCTGCTGTGTGCGTGCACCAGCTGCCTC

CAGGCCAACTACACGTGTGAGACAGATGGGGCCTGCATGGTTTCCATTTTC

AATCTGGATGGGATGGAGCACCATGTGCGCACCTGCATCCCCAAAGTGGAG

CTGGTCCCTGCCGGGAAGCCCTTCTACTGCCTGAGCTCGGAGGACCTGCGC

AACACCCACTGCTGCTACACTGACTACTGCAACAGGATCGACTTGAGGGTG

CCCAGTGGTCACCTCAAGGAGCCTGAGCACCCGTCCATGTGGGGCCCGGTG

GAG

In certain embodiments, the disclosure relates to heteromultimers that comprise at least one ALK4 polypeptide, which includes fragments, functional variants, and modified forms thereof. Preferably, ALK4 polypeptides for use in accordance with inventions of the disclosure (e.g., heteromultimers comprising an ALK4 polypeptide and uses thereof) are soluble (e.g., an extracellular domain of ALK4). In other preferred embodiments, ALK4 polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one ALK4 polypeptide that is at least 70%, 75%, 80%, 85%, 86%, 87%, 88%, 89%, 90%, 91%, 92%, 93%, 94%, 95%, 97%, 98%, or 99% identical to the amino acid sequence of SEQ ID NO: 9, 10, 19, 20, 42, 44, 47, 48, 74, and 76. In some embodiments, heteromultimer complexes of the disclosure consist or consist essentially of at least one ALK4 polypeptide that is at least 70%, 75%, 80%, 85%, 86%, 87%, 88%, 89%, 90%, 91%, 92%, 93%, 94%, 95%, 97%, 98%, or 99% identical to the amino acid sequence of SEQ ID NO: 9, 10, 19, 20, 42, 44, 47, 48, 74, and 76.

Figure 5:
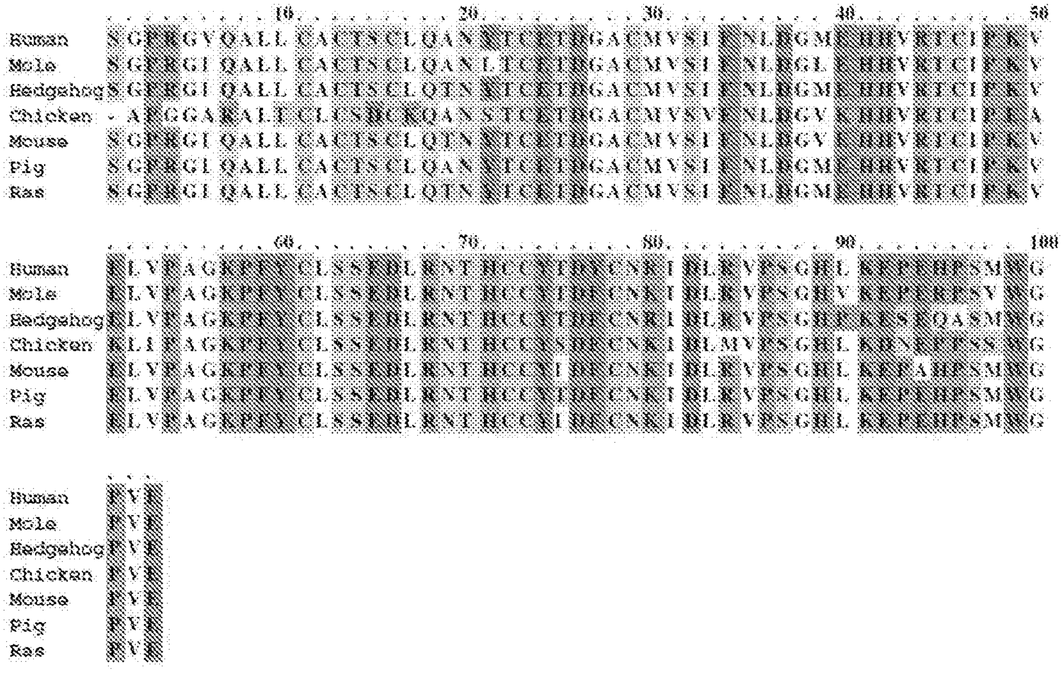
FIG. 5 shows a multiple sequence alignment of ALK4 extracellular domains derived from various vertebrate species (SEQ ID NOs: 59-65).
Figure 6A:
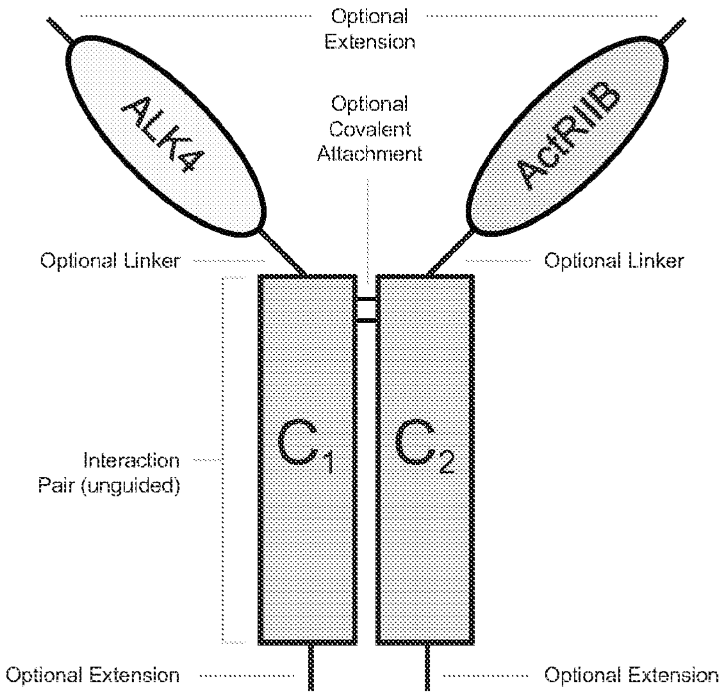
FIGS. 6A-6D show schematic examples of heteromeric protein complexes comprising an ALK4 polypeptide and an ActRIIB polypeptide. In the illustrated embodiments, the ALK4 polypeptide (from left to right) is part of a fusion polypeptide that comprises a first member of an interaction pair ("$C_1$"), and the ActRIIB polypeptide is part of a fusion polypeptide that comprises a second member of an interaction pair ("$C_2$"). Suitable interaction pairs included, for example, heavy chain and/or light chain immunoglobulin interaction pairs, truncations, and variants thereof such as those described herein [e.g., Spiess et al (2015) Molecular Immunology 67(2A): 95-106]. In each fusion polypeptide, a linker may be positioned between the ALK4 or ActRIIB polypeptide and the corresponding member of the interaction pair. The first and second members of the interaction pair may be unguided, meaning that the members of the pair may associate with each other or self-associate without substantial preference, and they may have the same or different amino acid sequences. See FIG. 8A. Alternatively, the interaction pair may be a guided (asymmetric) pair, meaning that the members of the pair associate preferentially with each other rather than self-associate. See FIG. 8B. Complexes of higher order can be envisioned. See FIGS. 8C and 8D.
Figure 6B:
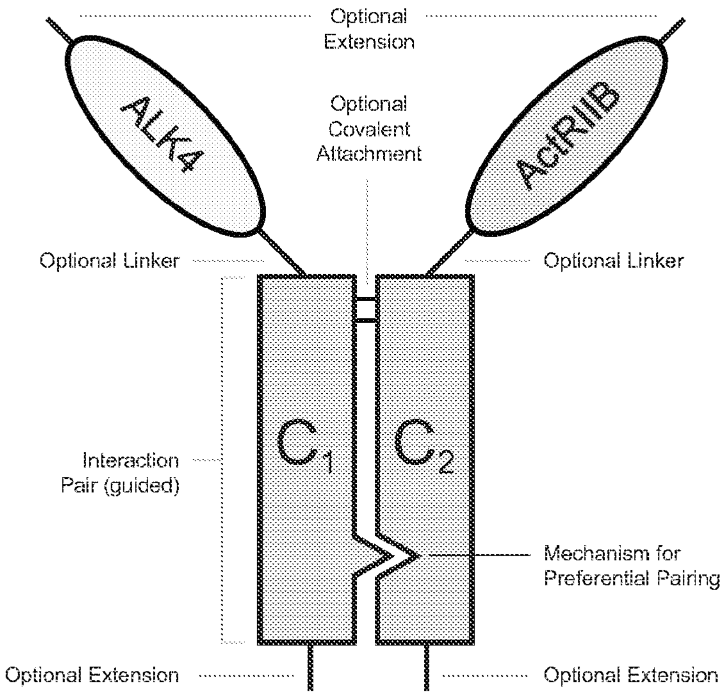
Figure 6C:
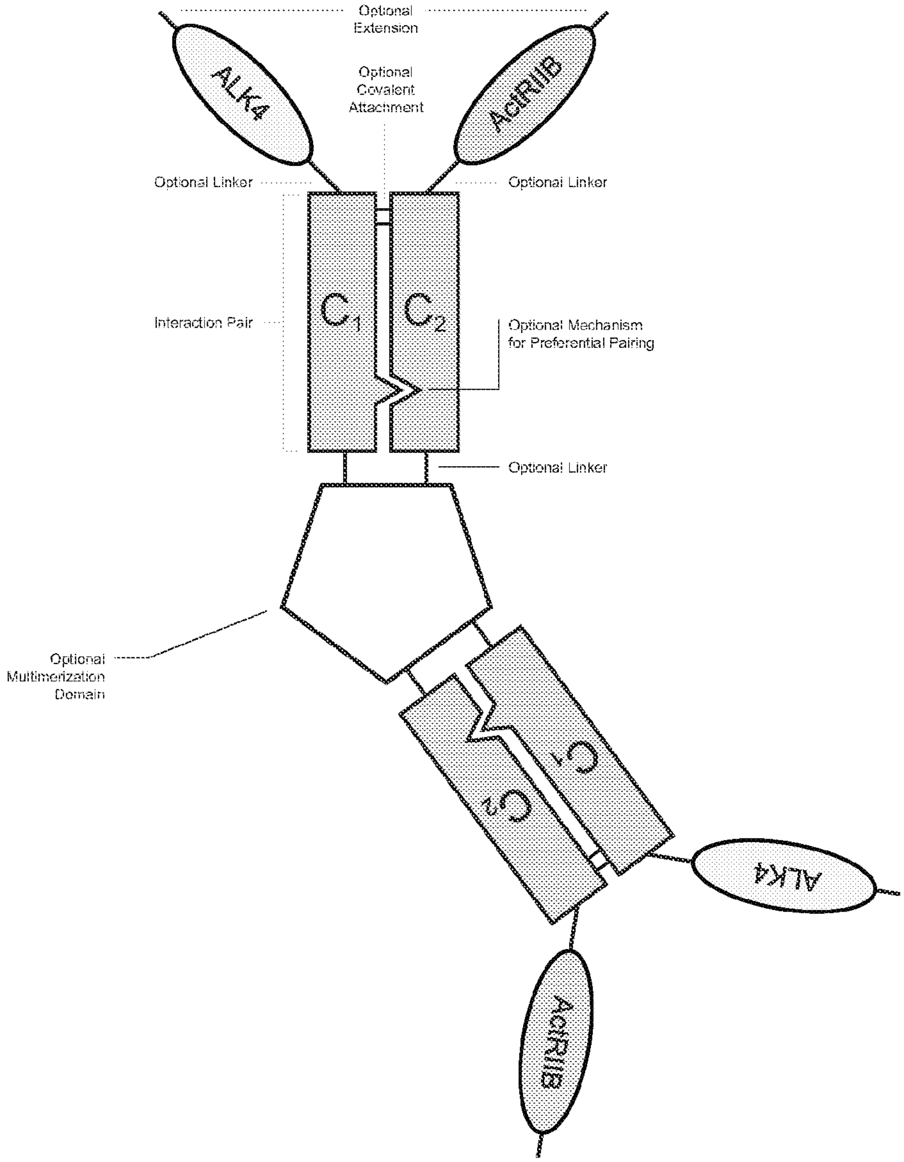
Figure 6D:
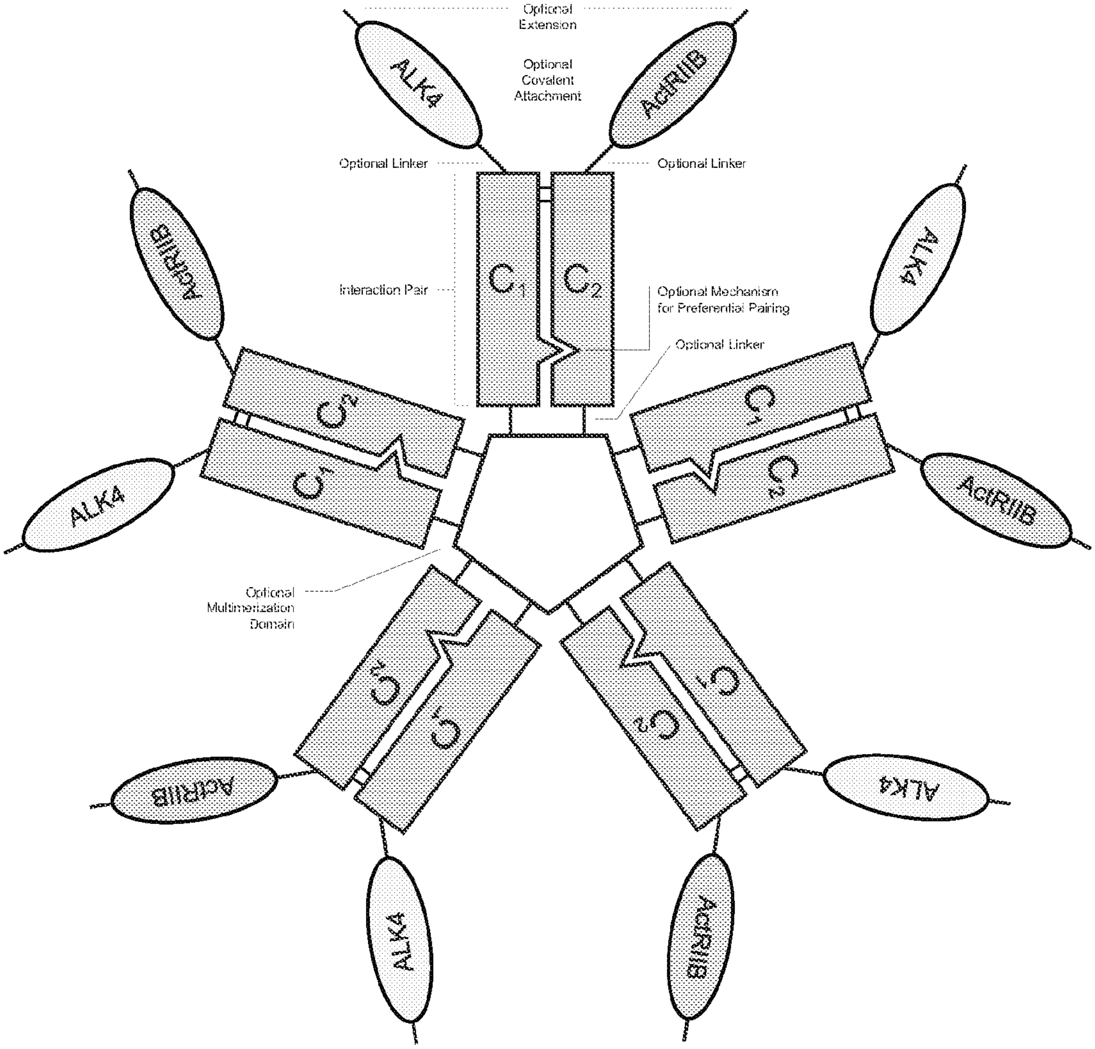

ALK4 is well-conserved among vertebrates, with large stretches of the extracellular domain completely conserved. For example, FIG. 5 depicts a multi-sequence alignment of a human ALK4 extracellular domain compared to various ALK4 orthologs. Many of the ligands that bind to ALK4 are also highly conserved. Accordingly, from these alignments, it is possible to predict key amino acid positions within the ligand-binding domain that are important for normal ALK4-ligand binding activities as well as to predict amino acid positions that are likely to be tolerant to substitution without significantly altering normal ALK4-ligand binding activities. Therefore, an active, human ALK4 variant polypeptide useful in accordance with the presently disclosed methods may include one or more amino acids at corresponding positions from the sequence of another vertebrate ALK4, or may include a residue that is similar to that in the human or other vertebrate sequences. Without meaning to be limiting, the following examples illustrate this approach to defining an active ALK4 variant. V6 in the human ALK4 extracellular domain (SEQ ID NO: 59) is isoleucine in *Mus muculus* ALK4 (SEQ ID NO: 63), and so the position may be altered, and optionally may be altered to another hydrophobic residue such as L, I, or F, or a non-polar residue such as A, as is observed in *Gallus gallus* ALK4 (SEQ ID NO: 62). E40 in the human extracellular domain is K in *Gallus gallus* ALK4, indicating that this site may be tolerant of a wide variety of changes, including polar residues, such as E, D, K, R, H, S, T, P, G, Y, and probably a non-polar residue such as A. S15 in the human extracellular domain is D in *Gallus gallus* ALK4, indicating that a wide structural variation is tolerated at this position, with polar residues favored, such as S, T, R, E, K, H, G, P, G and Y. E40 in the human extracellular domain is K in *Gallus gallus* ALK4, indicating that charged residues will be tolerated at this position, including D, R, K, H, as well as Q and N. R80 in the human extracellular domain is K in *Condylura cristata* ALK4 (SEQ ID NO: 60), indicating that basic residues are tolerated at this position, including R, K, and H. Y77 in the human extracellular domain is F in *Sus scrofa* ALK4 (SEQ ID NO: 64), indicating that aromatic residues are tolerated at this position, including F, W, and Y. P93 in the human extracellular domain is relatively poorly conserved, appearing as S in *Erinaceus europaeus* ALK4 (SEQ ID NO: 61) and N in *Gallus gallus* ALK4, thus essentially any amino acid should be tolerated at this position.

Moreover, ALK4 proteins have been characterized in the art in terms of structural and functional characteristics, particularly with respect to ligand binding [e.g., Harrison et al. (2003) J Biol Chem 278(23):21129-21135; Romano et al. (2012) J Mol Model 18(8):3617-3625; and Calvanese et al. (2009) 15(3):175-183]. In addition to the teachings herein, these references provide amply guidance for how to generate ALK4 variants that retain one or more normal activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ALK4, as demarcated by the outermost of these conserved cysteines, corresponds to positions 34-101 of SEQ ID NO: 9 (ALK4 precursor). Thus, the structurally less-ordered amino acids flanking these cysteine-demarcated core sequences can be truncated by 1, 2, 3, 4, 5, 6, 7, 8, 9, or 10, residues at the N-terminus or 1, 2, 3, 4, 5, 6, 7, 8, 9, 10, 11, 12, 13, 14, 15, 16, 17, 18, 19, 20, 21, 22, 23, 24, 25, or 26 residues at the C-terminus without necessarily altering ligand binding. Exemplary ALK4 extracellular domains for N-terminal and/or C-terminal truncation include SEQ ID NOs: 10 and 20.

Accordingly, a general formula for an active portion (e.g., a ligand-binding portion) of ALK4 comprises amino acids 34-101. Therefore ALK4 polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ALK4 beginning at a residue corresponding to any one of amino acids 24-34 (e.g., beginning at any one of amino acids 24, 25, 26, 27, 28, 29, 30, 31, 32, 33, or 34) of SEQ ID NO: 1 and ending at a position corresponding to any one amino acids 101-126 (e.g., ending at any one of amino acids 101, 102, 103, 104, 105, 106, 107, 108, 109, 110, 111, 112, 113, 114, 115, 116, 117, 118, 119, 120, 121, 122, 123, 124, 125, or 126) of SEQ ID NO: 9. Other examples include constructs that begin at a position from 24-34 (e.g., any one of positions 24, 25, 26, 27, 28, 29, 30, 31, 32, 33, or 34), 25-34 (e.g., any one of positions 25, 26, 27, 28, 29, 30, 31, 32, 33, or 34), or 26-34 (e.g., any one of positions 26, 27, 28, 29, 30, 31, 32, 33, or 34) of SEQ ID NO: 9 and end at a position from 101-126 (e.g., any one of positions 101, 102, 103, 104, 105, 106, 107, 108, 109, 110, 111, 112, 113, 114, 115, 116, 117, 118, 119, 120, 121, 122, 123, 124, 125, or 126), 102-126 (e.g., any one of positions 102, 103, 104, 105, 106, 107, 108, 109, 110, 111, 112, 113, 114, 115, 116, 117, 118, 119, 120, 121, 122, 123, 124, 125, or 126), 101-125 (e.g., any one of positions 101, 102, 103, 104, 105, 106, 107, 108, 109, 110, 111, 112, 113, 114, 115, 116, 117, 118, 119, 120, 121, 122, 123, 124, or 125), 101-124 (e.g., any one of positions 101, 102, 103, 104, 105, 106, 107, 108, 109, 110, 111, 112, 113, 114, 115, 116, 117, 118, 119, 120, 121, 122, 123, or 124), 101-121 (e.g., any one of positions 101, 102, 103, 104, 105, 106, 107, 108, 109, 110, 111, 112, 113, 114, 115, 116, 117, 118, 119, 120, or 121), 111-126 (e.g., any one of positions 111, 112, 113, 114, 115, 116, 117, 118, 119, 120, 121, 122, 123, 124, 125, or 126), 111-125 (e.g., any one of positions 111, 112, 113, 114, 115, 116, 117, 118, 119, 120, 121, 122, 123, 124, or 125), 111-124 (e.g., any one of positions 111, 112, 113, 114, 115, 116, 117, 118, 119, 120, 121, 122, 123, or 124), 121-126 (e.g., any one of positions 121, 122, 123, 124, 125, or 126), 121-125 (e.g., any one of positions 121, 122, 123, 124, or 125), 121-124 (e.g., any one of positions 121, 122, 123, or 124), or 124-126 (e.g., any one of positions 124, 125, or 126) of SEQ ID NO: 9. Variants within these ranges are also contemplated, particularly those having at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 9.

The variations described herein may be combined in various ways. In some embodiments, ALK4 variants comprise no more than 1, 2, 5, 6, 7, 8, 9, 10 or 15 conservative amino acid changes in the ligand-binding pocket. Sites outside the binding pocket, at which variability may be particularly well tolerated, include the amino and carboxy termini of the extracellular domain (as noted above), In some embodiments, the present disclosure contemplates making functional variants by modifying the structure of an ALK4 polypeptide and/or an ActRIIB polypeptide. Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta superfamily ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin BC, activin AE, activin BE, nodal, glial cell-derived neurotrophic factor (GDNF), neurturin, artemin, persephin, MIS, and Lefty.

In some embodiments, the present disclosure contemplates making functional variants by modifying the structure of an ALK4 and/or ActRIIB polypeptide for such purposes as enhancing therapeutic efficacy or stability (e.g., increase shelf-life and/or resistance to proteolytic degradation).

In some embodiments, the present disclosure contemplates specific mutations of an ALK4 polypeptide and/or an ActRIIB polypeptide so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, heteromeric complexes of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of an ALK4 and/or an ActRIIB polypeptide as well as truncation mutants. Pools of combinatorial mutants are especially useful for identifying functionally active (e.g., TGF-beta superfamily ligand binding) ALK4 and/or ActRIIB sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, ALK4:ActRIIB complex variants may be screened for ability to bind to one or more TGF-beta superfamily ligands to prevent binding of a TGF-beta superfamily ligand to a TGF-beta superfamily receptor, and/or to interfere with signaling caused by an TGF-beta superfamily ligand.

The activity of a ALK4:ActRIIB heteromultimer may be tested, for example, in a cell-based or in vivo assay. For example, the effect of an ALK4:ActRIIB heteromultimer on the expression of genes or activity of proteins involved in muscle production in a muscle cell may be assessed. This may, as needed, be performed in the presence of one or more TGF-beta superfamily ligands, and cells may be transfected so as to produce an ALK4:ActRIIB heteromultimer, and optionally, a TGF-beta superfamily ligand. Likewise, an ALK4:ActRIIB heteromultimer may be administered to a mouse or other animal, and one or more measurements, such as muscle formation and strength may be assessed using art-recognized methods. Similarly, the activity of an ALK4:ActRIIB heteromultimer, or variants thereof, may be tested, for example, in osteoblasts, adipocytes, and/or neuronal cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference ALK4:ActRIIB heteromultimer. Such variants, when expressed from recombinant DNA constructs, can be used in gene therapy protocols. Likewise, mutagenesis can give rise to variants which have intracellular half-lives dramatically different than the corresponding unmodified ALK4:ActRIIB heteromultimer. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter one or more activities of the ALK4:ActRIIB heteromultimer including, for example, immunogenicity, half-life, and solubility.

A combinatorial library may be produced by way of a degenerate library of genes encoding a library of polypeptides which each include at least a portion of potential ALK4 and/or ActRIIB sequences. For instance, a mixture of synthetic oligonucleotides can be enzymatically ligated into gene sequences such that the degenerate set of potential ALK4 and/or ActRIIB encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art [Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; and Ike et al. (1983) Nucleic Acid Res. 11:477]. Such techniques have been employed in the directed evolution of other proteins [Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815].

Alternatively, other forms of mutagenesis can be utilized to generate a combinatorial library. For example, ALK4: ActRIIB heteromultimers can be generated and isolated from a library by screening using, for example, alanine scanning mutagenesis [Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [Gustin et al. (1993) Virology 193:653-660; and Brown et al. (1992) Mol. Cell Biol. 12:2644-2652; McKnight et al. (1982) Science 232:316], by saturation mutagenesis [Meyers et al., (1986) Science 232:613]; by PCR mutagenesis [Leung et al. (1989) Method Cell Mol Biol 1:11-19]; or by random mutagenesis, including chemical mutagenesis [Miller et al. (1992) A Short Course in Bacterial Genetics, CSHL Press, Cold Spring Harbor, N.Y.; and Greener et al. (1994) Strategies in Mol Biol 7:32-34]. Linker scanning mutagenesis, particularly in a combinatorial setting, is an attractive method for identifying truncated (bioactive) forms of ALK4 and/or ActRIIB polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ALK4:ActRIIB heteromultimers. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin BC, activin AE, activin BE, nodal, glial cell-derived neurotrophic factor (GDNF), neurturin, artemin, persephin, MIS, and Lefty) binding assays and/or TGF-beta ligand-mediated cell signaling assays.

In certain embodiments, ALK4:ActRIIB heteromultimers may further comprise post-translational modifications in addition to any that are naturally present in the ALK4 and/or ActRIIB polypeptide. Such modifications include, but are not limited to, acetylation, carboxylation, glycosylation, phosphorylation, lipidation, and acylation. As a result, ALK4:ActRIIB heteromultimers may comprise non-amino acid elements, such as polyethylene glycols, lipids, polysaccharide or monosaccharide, and phosphates. Effects of such non-amino acid elements on the functionality of a heteromultimer complex may be tested as described herein for other heteromultimer variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the ALK4 and/or ActRIIB polypeptide as well as heteromultimers comprising the same.

In certain preferred embodiments, heteromultimers described herein comprise at least one ALK4 polypeptide associated, covalently or non-covalently, with at least one ActRIIB polypeptide. Preferably, polypeptides disclosed herein form heterodimeric complexes, although higher order heteromultimeric complexes are also included such as, but not limited to, heterotrimers, heterotetramers, and further oligomeric structures (see, e.g., FIG. 6). In some embodiments, ALK4 and/or ActRIIB polypeptides comprise at least one multimerization domain. As disclosed herein, the term "multimerization domain" refers to an amino acid or sequence of amino acids that promote covalent or non-covalent interaction between at least a first polypeptide and at least a second polypeptide. Polypeptides disclosed herein may be joined covalently or non-covalently to a multimerization domain. Preferably, a multimerization domain promotes interaction between a first polypeptide (e.g., an ALK4 polypeptide) and a second polypeptide (e.g., an ActRIIB polypeptide) to promote heteromultimer formation (e.g., heterodimer formation), and optionally hinders or otherwise disfavors homomultimer formation (e.g., homodimer formation), thereby increasing the yield of desired heteromultimer (see, e.g., FIG. 6).

Many methods known in the art can be used to generate ALK4:ActRIIB heteromultimers. For example, non-naturally occurring disulfide bonds may be constructed by replacing on a first polypeptide (e.g., an ALK4 polypeptide) a naturally occurring amino acid with a free thiol-containing residue, such as cysteine, such that the free thiol interacts with another free thiol-containing residue on a second polypeptide (e.g., an ActRIIB polypeptide) such that a disulfide bond is formed between the first and second polypeptides. Additional examples of interactions to promote heteromultimer formation include, but are not limited to, ionic interactions such as described in Kjaergaard et al., WO2007147901; electrostatic steering effects such as described in Kannan et al., U.S. Pat. No. 8,592,562; coiled-coil interactions such as described in Christensen et al., U.S.20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology.

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of an ALK4 polypeptide and the amino acid sequence of a first member of an interaction pair; and the second polypeptide comprises the amino acid sequence of an ActRIIB polypeptide and the amino acid sequence of a second member of an interaction pair. The interaction pair may be any two polypeptide sequences that interact to form a complex, particularly a heterodimeric complex although operative embodiments may also employ an interaction pair that can form a homodimeric complex. One member of the interaction pair may be fused to an ALK4 or ActRIIB polypeptide as described herein, including for example, a polypeptide sequence comprising, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the sequence of any one of SEQ ID NOs: 2, 3, 5, 6, 10, and 20. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form a heterodimeric complex (see, e.g., FIG. 6). Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

As specific examples, the present disclosure provides fusion proteins comprising ALK4 or ActRIIB fused to a polypeptide comprising a constant domain of an immunoglobulin, such as a CH1, CH2, or CH3 domain of an immunoglobulin or an Fc domain. Fc domains derived from human IgG1, IgG2, IgG3, and IgG4 are provided herein. Other mutations are known that decrease either CDC or ADCC activity, and collectively, any of these variants are included in the disclosure and may be used as advantageous components of a heteromultimeric complex of the disclosure. Optionally, the IgG1 Fc domain of SEQ ID NO: 31 has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wild-type Fc domain.

An example of a native amino acid sequence that may be used for the Fc portion of human IgG1 (G1Fc) is shown below (SEQ ID NO: 31). Dotted underline indicates the hinge region, and solid underline indicates positions with naturally occurring variants. In part, the disclosure provides polypeptides comprising, consisting essentially of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 31. Naturally occurring variants in G1Fc would include E134D and M136L according to the numbering system used in SEQ ID NO: 31 (see Uniprot P01857).

```
                                                    (SEQ ID NO: 31)
  1  THTCPPCPAP ELLGGPSVFL FPPKPKDTLM ISRTPEVTCV VVDVSHEDPE

 51  VKFNWYVDGV EVHNAKTKPR EEQYNSTYRV VSVLTVLHQD WLNGKEYKCK

101  VSNKALPAPI EKTISKAKGQ PREPQVYTLP PSREEMTKNQ VSLTCLVKGF

151  YPSDIAVEWE SNGQPENNYK TTPPVLDSDG SFFLYSKLTV DKSRWQQGNV

201  FSCSVMHEAL HNHYTQKSLS LSPGK
```

An example of a native amino acid sequence that may be used for the Fc portion of human IgG2 (G2Fc) is shown below (SEQ ID NO: 32). Dotted underline indicates the hinge region and double underline indicates positions where there are data base conflicts in the sequence (according to UniProt P01859). In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 32.

```
                                                    (SEQ ID NO: 32)
  1  VECPPCPAPP VAGPSVFLFP PKPKDTLMIS RTPEVTCVVV DVSHEDPEVQ

 51  FNWYVDGVEV HNAKTKPREE QFNSTFRVVS VLTVVHQDWL NGKEYKCKVS

101  NKGLPAPIEK TISKTKGQPR EPQVYTLPPS REEMTKNQVS LTCLVKGFYP

151  SDIAVEWESN GQPENNYKTT PPMLDSDGSF FLYSKLTVDK SRWQQGNVFS

201  CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 33) contains a short hinge region consisting of a single 15-residue segment, whereas the second G3Fc sequence (SEQ ID NO: 34) contains a full-length hinge region. In each case, dotted underline indicates the hinge region, and solid underline indicates positions with naturally occurring variants according to UniProt P01859. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NOs: 33 and 34.

```
                                           (SEQ ID NO: 33)
  1  EPKSCDTPPP CPRCPAPELL GGPSVFLFPP KPKDTLMISR TPEVTCVVVD

 51  VSHEDPEVQF KWYVDGVEVH NAKTKPREEQ YNSTFRVVSV LTVLHQDWLN

101  GKEYKCKVSN KALPAPIEKT ISKTKGQPRE PQVYTLPPSR EEMTKNQVSL

151  TCLVKGFYPS DIAVEWESSG QPENNYNTTP PMLDSDGSFF LYSKLTVDKS

201  RWQQGNIFSC SVMHEALHNR FTQKSLSLSP GK
```

```
                                           (SEQ ID NO: 34)
  1  ELKTPLGDTT HTCPRCPEPK SCDTPPPCPR CPEPKSCDTP PPCPRCPEPK

 51  SCDTPPPCPR CPAPELLGGP SVFLFPPKPK DTLMISRTPE VTCVVVDVSH

101  EDPEVQFKWY VDGVEVHNAK TKPREEQYNS TFRVVSVLTV LHQDWLNGKE

151  YKCKVSNKAL PAPIEKTISK TKGQPREPQV YTLPPSREEM TKNQVSLTCL

201  VKGFYPSDIA VEWESSGQPE NNYNTTPPML DSDGSFFLYS KLTVDKSRWQ

251  QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 33, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 35). Dotted underline indicates the hinge region. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 35.

```
                                           (SEQ ID NO: 35)
  1  ESKYGPPCPS CPAPEFLGGP SVFLFPPKPK DTLMISRTPE VTCVVVDVSQ

 51  EDPEVQFNWY VDGVEVHNAK TKPREEQFNS TYRVVSVLTV LHQDWLNGKE

101  YKCKVSNKGL PSSIEKTISK AKGQPREPQV YTLPPSQEEM TKNQVSLTCL

151  VKGFYPSDIA VEWESNGQPE NNYKTTPPVL DSDGSFFLYS RLTVDKSRWQ

201  EGNVFSCSVM HEALHNHYTQ KSLSLSLGK
```

A variety of engineered mutations in the Fc domain are presented herein with respect to the G1Fc sequence (SEQ ID NO: 31), and analogous mutations in G2Fc, G3Fc, and G4Fc can be derived from their alignment with G1Fc in FIG. 3. Due to unequal hinge lengths, analogous Fc positions based on isotype alignment (FIG. 3) possess different amino acid numbers in SEQ ID NOs: 31, 32, 33, 34, and 35. It can also be appreciated that a given amino acid position in an immunoglobulin sequence consisting of hinge, $C_H2$, and $C_H3$ regions (e.g., SEQ ID NOs: 31, 32, 33, 34, and 35) will be identified by a different number than the same position when numbering encompasses the entire IgG1 heavy-chain constant domain (consisting of the $C_HL$ hinge, CH2, and $C_H3$ regions) as in the Uniprot database. For example, correspondence between selected $C_H3$ positions in a human G1Fc sequence (SEQ ID NO: 31), the human IgG1 heavy chain constant domain (Uniprot P01857), and the human IgG1 heavy chain is as follows.

Correspondence of $C_H3$ Positions in Different Numbering Systems

| G1Fc (Numbering begins at first threonine in hinge region) | IgG1 heavy chain constant domain (Numbering begins at $C_H1$) | IgG1 heavy chain (EU numbering scheme of Kabat et al., 1991*) |
|---|---|---|
| Y127 | Y232 | Y349 |
| S132 | S237 | S354 |
| E134 | E239 | E356 |

-continued

Correspondence of $C_H3$ Positions in Different Numbering Systems

| G1Fc (Numbering begins at first threonine in hinge region) | IgG1 heavy chain constant domain (Numbering begins at $C_H1$) | IgG1 heavy chain (EU numbering scheme of Kabat et al., 1991*) |
|---|---|---|
| K138 | K243 | K360 |
| T144 | T249 | T366 |
| L146 | L251 | L368 |
| N162 | N267 | N384 |
| K170 | K275 | K392 |
| D177 | D282 | D399 |
| D179 | D284 | D401 |
| Y185 | Y290 | Y407 |
| K187 | K292 | K409 |
| H213 | H318 | H435 |
| K217 | K322 | K439 |

*Kabat et al. (eds) 1991; pp. 688-696 in *Sequences of Proteins of Immunological Interest*, 5$^{th}$ ed., Vol. 1, NIH, Bethesda, MD.

A problem that arises in large-scale production of asymmetric immunoglobulin-based proteins from a single cell line is known as the “chain association issue”. As confronted prominently in the production of bispecific antibodies, the chain association issue concerns the challenge of efficiently producing a desired multichain protein from among the multiple combinations that inherently result when different heavy chains and/or light chains are produced in a single cell line [Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields [Klein et al (2012) mAbs 4:653-663; and Spiess et al (2015) Molecular Immunology 67(2A): 95-106]. Methods to obtain desired pairing of Fc-containing chains include, but are not limited to, charge-based pairing (electrostatic steering), “knobs-into-holes” steric pairing, SEEDbody pairing, and leucine zipper-based pairing [Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605]. As described herein, these methods may be used to generate ALK4-Fc:ActRIIB-Fc heteromultimer complexes. See FIG. 6.

For example, one means by which interaction between specific polypeptides may be promoted is by engineering protuberance-into-cavity (knob-into-holes) complementary regions such as described in Arathoon et al., U.S. Pat. No. 7,183,076 and Carter et al., U.S. Pat. No. 5,731,168. “Protuberances” are constructed by replacing small amino acid side chains from the interface of the first polypeptide (e.g., a first interaction pair) with larger side chains (e.g., tyrosine or tryptophan). Complementary “cavities” of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' [residue numbering in the second chain is indicated by (')]. It should be noted that the numbering scheme used here to designate residues in the IgG1 CH3 domain conforms to the EU numbering scheme of Kabat. Due to the 2-fold symmetry present in the CH3-CH3 domain interactions, each unique interaction will represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation.

The electrostatic steering effect on heterodimer formation and homodimer discouragement can be further enhanced by mutation of additional charge residues which may or may not be paired with an oppositely charged residue in the second chain including, for example, Arg355 and Lys360. The table below lists possible charge change mutations that can be used, alone or in combination, to enhance ALK4:ActRIIB heteromultimer formation.

Examples of Pair-Wise Charged Residue Mutations to Enhance Heterodimer Formation

| Position in first chain | Mutation in first chain | Interacting position in second chain | Corresponding mutation in second chain |
|---|---|---|---|
| Lys409 | Asp or Glu | Asp399' | Lys, Arg, or His |
| Lys392 | Asp or Glu | Asp399' | Lys, Arg, or His |
| Lys439 | Asp or Glu | Asp356' | Lys, Arg, or His |
| Lys370 | Asp or Glu | Glu357' | Lys, Arg, or His |
| Asp399 | Lys, Arg, or His | Lys409' | Asp or Glu |
| Asp399 | Lys, Arg, or His | Lys392' | Asp or Glu |
| Asp356 | Lys, Arg, or His | Lys439' | Asp or Glu |
| Glu357 | Lys, Arg, or His | Lys370' | Asp or Glu |

In some embodiments, one or more residues that make up the CH3-CH3 interface in a fusion protein of the instant application are replaced with a charged amino acid such that the interaction becomes electrostatically unfavorable. For example, a positive-charged amino acid in the interface (e.g., a lysine, arginine, or histidine) is replaced with a negatively charged amino acid (e.g., aspartic acid or glutamic acid). Alternatively, or in combination with the forgoing substitution, a negative-charged amino acid in the interface is replaced with a positive-charged amino acid. In certain embodiments, the amino acid is replaced with a non-naturally occurring amino acid having the desired charge characteristic. It should be noted that mutating negatively charged residues (Asp or Glu) to His will lead to increase in side chain volume, which may cause steric issues. Furthermore, His proton donor- and acceptor-form depends on the localized environment. These issues should be taken into consideration with the design strategy. Because the interface residues are highly conserved in human and mouse IgG subclasses, electrostatic steering effects disclosed herein can be applied to human and mouse IgG1, IgG2, IgG3, and IgG4. This strategy can also be extended to modifying uncharged residues to charged residues at the CH3 domain interface.

In part, the disclosure provides desired pairing of asymmetric Fc-containing polypeptide chains using Fc sequences engineered to be complementary on the basis of charge pairing (electrostatic steering). One of a pair of Fc sequences with electrostatic complementarity can be arbitrarily fused to the ALK4 or ActRIIB polypeptide of the construct, with or without an optional linker, to generate an ALK4:ActRIIB heteromultimer. This single chain can be coexpressed in a cell of choice along with the Fc sequence complementary to the first Fc to favor generation of the desired multichain construct (e.g., ALK4:ActRIIB heteromultimer). In this example based on electrostatic steering, SEQ ID NO: 23 [human G1Fc(E134K/D177K)] and SEQ ID NO: 24 [human G1Fc(K170D/K187D)] are examples of complementary Fc sequences in which the engineered amino acid substitutions are double underlined, and the TGF-beta superfamily type I or type II receptor polypeptide of the construct can be fused to either SEQ ID NO: 23 or SEQ ID NO: 24, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 3) will generate complementary Fc pairs which may be used instead of the complementary hG1Fc pair below (SEQ ID NOs: 23 and 24).

```
                                                  (SEQ ID NO: 23)
  1  THTCPPCPAP ELLGGPSVFL FPPKPKDTLM ISRTPEVTCV VVDVSHEDPE

 51  VKFNWYVDGV EVHNAKTKPR EEQYNSTYRV VSVLTVLHQD WLNGKEYKCK

101  VSNKALPAPI EKTISKAKGQ PREPQVYTLP PSRKEMTKNQ VSLTCLVKGF

151  YPSDIAVEWE SNGQPENNYK TTPPVLKSDG SFFLYSKLTV DKSRWQQGNV

201  FSCSVMHEAL HNHYTQKSLS LSPGK
```

```
                                                  (SEQ ID NO: 24)
  1  THTCPPCPAP ELLGGPSVFL FPPKPKDTLM ISRTPEVTCV VVDVSHEDPE

 51  VKFNWYVDGV EVHNAKTKPR EEQYNSTYRV VSVLTVLHQD WLNGKEYKCK

101  VSNKALPAPI EKTISKAKGQ PREPQVYTLP PSREEMTKNQ VSLTCLVKGF

151  YPSDIAVEWE SNGQPENNYD TTPPVLDSDG SFFLYSDLTV DKSRWQQGNV

201  FSCSVMHEAL HNHYTQKSLS LSPGK
```

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to the ALK4 or ActRIIB polypeptide of the construct, with or without an optional linker, to generate an ALK4:ActRIIB heteromultimer. This single chain can be co-expressed in a cell of choice along with the Fc sequence complementary to the first Fc to favor generation of the desired multi-chain construct. In this example based on knobs-into-holes pairing, SEQ ID NO: 25 [human G1Fc(T144Y)] and SEQ ID NO: 26 [human G1Fc (Y185T)] are examples of complementary Fc sequences in which the engineered amino acid substitutions are double underlined, and the ALK4 or ActRIIB polypeptide of the construct can be fused to either SEQ ID NO: 25 or SEQ ID NO: 26, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 3) will generate complementary Fc pairs which may be used instead of the complementary hG1Fc pair below (SEQ ID NOs: 25 and 26).

(SEQ ID NO: 25)

```
1   THTCPPCPAP ELLGGPSVFL FPPKPKDTLM ISRTPEVTCV VVDVSHEDPE
51  VKFNWYVDGV EVHNAKTKPR EEQYNSTYRV VSVLTVLHQD WLNGKEYKCK
101 VSNKALPAPI EKTISKAKGQ PREPQVYTLP PSREEMTKNQ VSLYCLVKGF
151 YPSDIAVEWE SNGQPENNYK TTPPVLDSDG SFFLYSKLTV DKSRWQQGNV
201 FSCSVMHEAL HNHYTQKSLS LSPGK
```

(SEQ ID NO: 26)

```
1   THTCPPCPAP ELLGGPSVFL FPPKPKDTLM ISRTPEVTCV VVDVSHEDPE
51  VKFNWYVDGV EVHNAKTKPR EEQYNSTYRV VSVLTVLHQD WLNGKEYKCK
101 VSNKALPAPI EKTISKAKGQ PREPQVYTLP PSREEMTKNQ VSLTCLVKGF
151 YPSDIAVEWE SNGQPENNYK TTPPVLDSDG SFFLTSKLTV DKSRWQQGNV
201 FSCSVMHEAL HNHYTQKSLS LSPGK
```

An example of Fc complementarity based on knobs-into-holes pairing combined with an engineered disulfide bond is disclosed in SEQ ID NO: 27 [hG1Fc(S132C/T144W)] and SEQ ID NO: 28 [hG1Fc(Y127C/T144S/L146A/Y185V)]. The engineered amino acid substitutions in these sequences are double underlined, and the TGF-beta superfamily type I or type II polypeptide of the construct can be fused to either SEQ ID NO: 27 or SEQ ID NO: 28, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 3) will generate complementary Fc pairs which may be used instead of the complementary hG1Fc pair below (SEQ ID NOs: 27 and 28).

(SEQ ID NO: 27)

```
1   THTCPPCPAP ELLGGPSVFL FPPKPKDTLM ISRTPEVTCV VVDVSHEDPE
51  VKFNWYVDGV EVHNAKTKPR EEQYNSTYRV VSVLTVLHQD WLNGKEYKCK
101 VSNKALPAPI EKTISKAKGQ PREPQVYTLP PCREEMTKNQ VSLWCLVKGF
151 YPSDIAVEWE SNGQPENNYK TTPPVLDSDG SFFLYSKLTV DKSRWQQGNV
201 FSCSVMHEAL HNHYTQKSLS LSPGK
```

(SEQ ID NO: 28)

```
1   THTCPPCPAP ELLGGPSVFL FPPKPKDTLM ISRTPEVTCV VVDVSHEDPE
51  VKFNWYVDGV EVHNAKTKPR EEQYNSTYRV VSVLTVLHQD WLNGKEYKCK
101 VSNKALPAPI EKTISKAKGQ PREPQVCTLP PSREEMTKNQ VSLSCAVKGF
151 YPSDIAVEWE SNGQPENNYK TTPPVLDSDG SFFLVSKLTV DKSRWQQGNV
201 FSCSVMHEAL HNHYTQKSLS LSPGK
```

In part, the disclosure provides desired pairing of asymmetric Fc-containing polypeptide chains using Fc sequences engineered to generate interdigitating β-strand segments of human IgG and IgA $C_H3$ domains. Such methods include the use of strand-exchange engineered domain (SEED) $C_H3$ heterodimers allowing the formation of SEEDbody fusion proteins [Davis et al. (2010) Protein Eng Design Sel 23:195-202]. One of a pair of Fc sequences with SEEDbody complementarity can be arbitrarily fused to the ALK4 or ActIIB of the construct, with or without an optional linker, to generate an ALK4 or ActRIIB fusion polypeptide. This single chain can be co-expressed in a cell of choice along with the Fc sequence complementary to the first Fc to favor generation of the desired multi-chain construct. In this example based on SEEDbody (Sb) pairing, SEQ ID NO: 29 [hG1Fc($Sb_{AG}$)] and SEQ ID NO: 30 [hG1Fc($Sb_{GA}$)] are examples of complementary IgG Fc sequences in which the engineered amino acid substitutions from IgA Fc are double underlined, and the ALK4 or ActRIIB polypeptide of the construct can be fused to either SEQ ID NO: 29 or SEQ ID NO: 30, but not both. Given the high degree of amino acid sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 3) will generate an Fc monomer which may be used in the complementary IgG-IgA pair below (SEQ ID NOs: 29 and 30).

```
                                                              (SEQ ID NO: 29)
  1    THTCPPCPAP  ELLGGPSVFL  FPPKPKDTLM  ISRTPEVTCV  VVDVSHEDPE

 51    VKFNWYVDGV  EVHNAKTKPR  EEQYNSTYRV  VSVLTVLHQD  WLNGKEYKCK

101    VSNKALPAPI  EKTISKAKGQ  PFRPEVHLLP  PSREEMTKNQ  VSLTCLARGF

151    YPKDIAVEWE  SNGQPENNYK  TTPSRQEPSQ  GTTTFAVTSK  LTVDKSRWQQ

201    GNVFSCSVMH  EALHNHYTQK  TISLSPGK

                                                              (SEQ ID NO: 30)
  1    THTCPPCPAP  ELLGGPSVFL  FPPKPKDTLM  ISRTPEVTCV  VVDVSHEDPE

 51    VKFNWYVDGV  EVHNAKTKPR  EEQYNSTYRV  VSVLTVLHQD  WLNGKEYKCK

101    VSNKALPAPI  EKTISKAKGQ  PREPQVYTLP  PPSEELALNE  LVTLTCLVKG

151    FYPSDIAVEW  ESNGQELPRE  KYLTWAPVLD  SDGSFFLYSI  LRVAAEDWKK

201    GDTFSCSVMH  EALHNHYTQK  SLDRSPGK
```

In part, the disclosure provides desired pairing of asymmetric Fc-containing polypeptide chains with a cleavable leucine zipper domain attached at the C-terminus of the Fc $C_H3$ domains. Attachment of a leucine zipper is sufficient to cause preferential assembly of heterodimeric antibody heavy chains [Wranik et al (2012) J Biol Chem 287:43331-43339]. As disclosed herein, one of a pair of Fc sequences attached to a leucine zipper-forming strand can be arbitrarily fused to the ALK4 or ActRIIB polypeptide of the construct, with or without an optional linker, to generate an ALK4 or ActRIIB fusion polypeptide. This single chain can be co-expressed in a cell of choice along with the Fc sequence attached to a complementary leucine zipper-forming strand to favor generation of the desired multi-chain construct. Proteolytic digestion of the construct with the bacterial endoproteinase Lys-C post purification can release the leucine zipper domain, resulting in an Fc construct whose structure is identical to that of native Fc. In this example based on leucine zipper pairing, SEQ ID NO: 36 [hG1Fc-Ap1 (acidic)] and SEQ ID NO: 37 [hG1Fc-Bp1 (basic)] are examples of complementary IgG Fc sequences in which the engineered complimentary leucine zipper sequences are underlined, and the ALK4 or ActRIIB polypeptide of the construct can be fused to either SEQ ID NO: 36 or SEQ ID NO: 37, but not both. Given the high degree of amino acid sequence identity between native hG1Fc, native hG2Fc, native hG3Fc, and native hG4Fc, it can be appreciated that leucine zipper-forming sequences attached, with or without an optional linker, to hG1Fc, hG2Fc, hG3Fc, or hG4Fc (see FIG. 3) will generate an Fc monomer which may be used in the complementary leucine zipper-forming pair below (SEQ ID NOs: 36 and 37).

```
                                                              (SEQ ID NO: 36)
  1    THTCPPCPAP  ELLGGPSVFL  FPPKPKDTLM  ISRTPEVTCV  VVDVSHEDPE

 51    VKFNWYVDGV  EVHNAKTKPR  EEQYNSTYRV  VSVLTVLHQD  WLNGKEYKCK

101    VSNKALPAPI  EKTISKAKGQ  PREPQVYTLP  PSREEMTKNQ  VSLTCLVKGF

151    YPSDIAVEWE  SNGQPENNYK  TTPPVLDSDG  SFFLYSKLTV  DKSRWQQGNV

201    FSCSVMHEAL  HNHYTQKSLS  LSPGKGGSAQ  LEKELQALEK  ENAQLEWELQ

251    ALEKELAQGA  T

                                                              (SEQ ID NO: 37)
  1    THTCPPCPAP  ELLGGPSVFL  FPPKPKDTLM  ISRTPEVTCV  VVDVSHEDPE

 51    VKFNWYVDGV  EVHNAKTKPR  EEQYNSTYRV  VSVLTVLHQD  WLNGKEYKCK

101    VSNKALPAPI  EKTISKAKGQ  PREPQVYTLP  PSREEMTKNQ  VSLTCLVKGF

151    YPSDIAVEWE  SNGQPENNYK  TTPPVLDSDG  SFFLYSKLTV  DKSRWQQGNV

201    FSCSVMHEAL  HNHYTQKSLS  LSPGKGGSAQ  LKKKLQALKK  KNAQLKWKLQ

251    ALKKKLAQGA  T
```

In certain aspects, the disclosure relates to ALK4 polypeptides (e.g., ALK4-Fc fusion proteins) comprising one or more amino acid modifications that alter the isoelectric point (pI) of the ALK4 polypeptide and/or ActRIIB polypeptides (e.g., ActRIIB-Fc fusion proteins) comprising one or more amino acid modifications that alter the isoelectric point of the ActRIIB polypeptide. In some embodiments, one or more candidate domains that have a pI value higher than about 5.0, 5.5, 6.0, 6.5, 7.0, 7.5, 8.0, 8.5, or 9.0 are selected for construction of the full multidomain protein. In other embodiments, one or more candidate domains that have a pI value less than about 9.0, 8.5, 8.0, 7.5, 7.0, 6.5, 6.0, 5.5, or 5.0 are selected for construction of the full multidomain protein. It will be understood by one skilled in the art that a single protein will have multiple charge forms. Without wishing to be bound by any particular theory, the charge of a protein can be modified by a number of different mechanisms including but not limited to, amino acid substitution, cationization, deamination, carboxyl-terminal amino acid heterogeneity, phosphorylation and glycosylation.

The pI of a protein may be determined by a variety of methods including but not limited to, isoelectric focusing and various computer algorithms (see for example Bjellqvist et al., 1993, Electrophoresis 14:1023). In one embodiment, pI is determined using a Pharmacia Biotech Multiphor 2 electrophoresis system with a multi temp refrigerated bath recirculation unit and an EPS 3501 XL power supply. Pre-cast ampholine gels (e.g., Amersham Biosciences, pI range 2.5-10) are loaded with protein samples. Broad range pI marker standards (e.g., Amersham, pI range 3-10, 8 .mu.L) are used to determine relative pI for the proteins. Electrophoresis is performed, for example, at 1500 V, 50 mA for 105 minutes. The gel is fixed using, for example, a Sigma fixing solution (5×) diluted with purified water to 1× Staining is performed, for example, overnight at room temperature using Simply Blue stain (Invitrogen). Destaining is carried out, for example, with a solution that consisted of 25% ethanol, 8% acetic acid and 67% purified water. Isoelectric points are determined using, for example, a Bio-Rad Densitometer relative to calibration curves of the standards. The one or more metrics may further include metrics characterizing stability of the domain under one or more different conditions selected from different pH values, different temperatures, different shear stresses, and different freeze/thaw cycles.

In part, the disclosure provides desired pairing of asymmetric Fc-containing polypeptide chains by methods described above in combination with additional mutations in the Fc domain which facilitate purification of the desired heteromeric species. An example is complementarity of Fc domains based on knobs-into-holes pairing combined with an engineered disulfide bond, as disclosed in SEQ ID NOs: 27-28, plus additional substitution of two negatively charged amino acids (aspartic acid or glutamic acid) in one Fc-containing polypeptide chain and two positively charged amino acids (e.g., arginine) in the complementary Fc-containing polypeptide chain (SEQ ID NOs: 66-67). These four amino acid substitutions facilitate selective purification of the desired heteromeric fusion protein from a heterogeneous polypeptide mixture based on differences in isoelectric point or net molecular charge. The engineered amino acid substitutions in these sequences are double underlined below, and the ALK4 or ActRIIB polypeptide of the construct can be fused to either SEQ ID NO: 66 or SEQ ID NO: 67, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 3) will generate complementary Fc pairs which may be used instead of the complementary hG1Fc pair below (SEQ ID NOs: 66-67).

```
                                                  (SEQ ID NO: 66)
  1  THTCPPCPAP ELLGGPSVFL FPPKPKDTLM ISRTPEVTCV VVDVSHEDPE

 51  VKFNWYVDGV EVHNAKTKPR EEQYNSTYRV VSVLTVLHQD WLNGKEYKCK

101  VSNKALPAPI EKTISKAKGQ PREPQVYTLP PCREEMTENQ VSLWCLVKGF

151  YPSDIAVEWE SNGQPENNYK TTPPVLDSDG SFFLYSKLTV DKSRWQQGNV

201  FSCSVMHEAL HNHYTQDSLS LSPGK

                                                  (SEQ ID NO: 67)
  1  THTCPPCPAP ELLGGPSVFL FPPKPKDTLM ISRTPEVTCV VVDVSHEDPE

 51  VKFNWYVDGV EVHNAKTKPR EEQYNSTYRV VSVLTVLHQD WLNGKEYKCK

101  VSNKALPAPI EKTISKAKGQ PREPQVCTLP PSREEMTKNQ VSLSCAVKGF

151  YPSDIAVEWE SRGQPENNYK TTPPVLDSRG SFFLVSKLTV DKSRWQQGNV

201  FSCSVMHEAL HNHYTQKSLS LSPGK
```

Another example involves complementarity of Fc domains based on knobs-into-holes pairing combined with an engineered disulfide bond, as disclosed in SEQ ID NOs: 27-28, plus a histidine-to-arginine substitution at position 213 in one Fc-containing polypeptide chain (SEQ ID NO: 68). This substitution (denoted H435R in the numbering system of Kabat et al.) facilitates separation of desired heteromer from undesirable homodimer based on differences in affinity for protein A. The engineered amino acid substitution is indicated by double underline, and the ALK4 or ActRIIB polypeptide of the construct can be fused to either SEQ ID NO: 68 or SEQ ID NO: 28, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 3) will generate complementary Fc pairs which may be used instead of the complementary hG1Fc pair of SEQ ID NO: 68 (below) and SEQ ID NO: 28.

```
                                                  (SEQ ID NO: 68)
  1  THTCPPCPAP ELLGGPSVFL FPPKPKDTLM ISRTPEVTCV VVDVSHEDPE

 51  VKFNWYVDGV EVHNAKTKPR EEQYNSTYRV VSVLTVLHQD WLNGKEYKCK

101  VSNKALPAPI EKTISKAKGQ PREPQVYTLP PCREEMTKNQ VSLWCLVKGF
```

-continued

```
151    YPSDIAVEWE SNGQPENNYK TTPPVLDSDG SFFLYSKLTV DKSRWQQGNV

201    FSCSVMHEAL HNRYTQKSLS LSPGK
```

A variety of engineered mutations in the Fc domain are presented above with respect to the G1Fc sequence (SEQ ID NO: 31). Analogous mutations in G2Fc, G3Fc, and G4Fc can be derived from their alignment with G1Fc in FIG. 3. Due to unequal hinge lengths, analogous Fc positions based on isotype alignment (FIG. 3) possess different amino acid numbers in SEQ ID NOs: 31, 32, 33, 34, and 35 as summarized in the following table.

Correspondence between $C_H3$ Positions for Human Fc Isotypes*

| IgG1 SEQ ID NO: 31 Numbering begins at THT . . . | IgG4 SEQ ID NO: 35 Numbering begins at ESK . . . | IgG2 SEQ ID NO: 32 Numbering begins at VEC . . . | IgG3 SEQ ID NO: 33 Numbering begins at EPK . . . |
|---|---|---|---|
| Y127 | Y131 | Y125 | Y134 |
| S132 | S136 | S130 | S139 |
| E134 | E138 | E132 | E141 |
| K138 | K142 | K136 | K145 |
| T144 | T148 | T142 | T151 |
| L146 | L150 | L144 | L153 |
| N162 | N166 | N160 | S169 |
| K170 | K174 | K168 | N177 |
| D177 | D181 | D175 | D184 |
| D179 | D183 | D177 | D186 |
| Y185 | Y189 | Y183 | Y192 |
| K187 | R191 | K185 | K194 |
| H213 | H217 | H211 | R220 |
| K217 | K221 | K215 | K224 |

*Numbering based on multiple sequence alignment shown in FIG. 3

It is understood that different elements of the fusion proteins (e.g., immunoglobulin Fc fusion proteins) may be arranged in any manner that is consistent with desired functionality. For example, an ALK4 and/or ActRIIB polypeptide domain may be placed C-terminal to a heterologous domain, or alternatively, a heterologous domain may be placed C-terminal to an ALK4 and/or ActRIIB polypeptide domain. The ALK4 and/or ActRIIB polypeptide domain and the heterologous domain need not be adjacent in a fusion protein, and additional domains or amino acid sequences may be included C- or N-terminal to either domain or between the domains.

For example, an ALK4 and/or ActRIIB receptor fusin protein may comprise an amino acid sequence as set forth in the formula A-B-C. The B portion corresponds to an ALK4 or ActRIIB polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10 (SEQ ID NO: 84), 2-5 (SEQ ID NO: 85), 2-4 (SEQ ID NO: 86), 2-3 glycine residues) or glycine and proline residues and may, for example, contain a single sequence of threonine/serine and glycines or repeating sequences of threonine/serine and/or glycines, e.g., GGG (SEQ ID NO: 13), GGGG (SEQ ID NO: 14), TGGGG (SEQ ID NO: 15), SGGGG (SEQ ID NO: 16), TGGG (SEQ ID NO: 17), SGGG (SEQ ID NO: 18), or GGGGS (SEQ ID NO: 58) singlets, or repeats. In certain embodiments, an ALK4 and/or ActRIIB fusion protein comprises an amino acid sequence as set forth in the formula A-B-C, wherein A is a leader (signal) sequence, B consists of an ALK4 and/or ActRIIB polypeptide domain, and C is a polypeptide portion that enhances one or more of in vivo stability, in vivo half-life, uptake/administration, tissue localization or distribution, formation of protein complexes, and/or purification. In certain embodiments, an ALK4 and/or ActRIIB fusion protein comprises an amino acid sequence as set forth in the formula A-B-C, wherein A is a TPA leader sequence, B consists of a ALK4 or ActRIIB receptor polypeptide domain, and C is an immunoglobulin Fc domain. Preferred fusion proteins comprise the amino acid sequence set forth in any one of SEQ ID NOs: 39, 41, 42, 44, 45, 46, 47, 48, 70, 72, 74, 76, 78, and 80.

In some embodiments, ALK4:ActRIIB heteromultimers further comprise one or none heterologous portions (domains) so as to confer a desired property. For example, some fusion domains are particularly useful for isolation of the fusion proteins by affinity chromatography. Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$ (SEQ ID NO: 87)) fusion partners. As another example, a fusion domain may be selected so as to facilitate detection of the ligand trip polypeptides. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus hemagglutinin (HA), and c-myc tags. In some cases, the fusion domains have a protease cleavage site, such as for factor Xa or thrombin, which allows the relevant protease to partially digest the fusion proteins and thereby liberate the recombinant proteins therefrom. The liberated proteins can then be isolated from the fusion domain by subsequent chromatographic separation.

In certain embodiments, ALK4 and/or ActRIIB polypeptides may contain one or more modifications that are capable of stabilizing the polypeptides. For example, such modifications enhance the in vitro half-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising an ALK4 and/or ActRIIB polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol.

In preferred embodiments, ALK4:ActRIIB heteromultimers to be used in accordance with the methods described herein are isolated complexes. As used herein, an isolated protein (or protein complex) or polypeptide (or polypeptide complex) is one which has been separated from a component of its natural environment. In some embodiments, a heteromultimer of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art [Flatman et al., (2007) J. Chromatogr. B 848:79-87]. In some embodiments, ALK4:ActRIIB heteromultimer preparations are substantially free of ALK4 and/or ActRIIB homomultimers. For example, in some embodiments, ALK4:ActRIIB heteromultimer preparations comprise less than about 10%, 9%, 8%, 7%, 6%, 5%, 4%, 3%, 2%, or less than 1% ALK4 homomultimers. In some embodiments, ALK4:ActRIIB heteromultimer preparations comprise less than about 10%, 9%, 8%, 7%, 6%, 5%, 4%, 3%, 2%, or less than 1% ActRIIB homomultimers. In some embodiments, ALK4:ActRIIB heteromultimer preparations comprise less than about 10%, 9%, 8%, 7%, 6%, 5%, 4%, 3%, 2%, or less than 1% ALK4 homomultimers and less than about 10%, 9%, 8%, 7%, 6%, 5%, 4%, 3%, 2%, or less than 1% ActRIIB homomultimers.

In certain embodiments, ALK4 and/or ActRIIB polypeptides, as well as heteromultimers comprising the same, of the disclosure can be produced by a variety of art-known techniques. For example, polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (Advanced ChemTech Model 396; Milligen/Biosearch 9600). Alternatively, the polypeptides, including fragments or variants thereof, may be recombinantly produced using various expression systems [*E. coli*, Chinese Hamster Ovary (CHO) cells, COS cells, baculovirus] as is well known in the art. In a further embodiment, the modified or unmodified polypeptides may be produced by digestion of recombinantly produced full-length ALK4 and/or ActRIIB polypeptides by using, for example, a protease, e.g., trypsin, thermolysin, chymotrypsin, pepsin, or paired basic amino acid converting enzyme (PACE). Computer analysis (using commercially available software, e.g., MacVector, Omega, PCGene, Molecular Simulation, Inc.) can be used to identify proteolytic cleavage sites.

3. Nucleic Acids Encoding ALK4 and/or ActRIIB Polypeptides

In certain embodiments, the present disclosure provides isolated and/or recombinant nucleic acids encoding ALK4 and/or ActRIIB polypeptides (including fragments, functional variants, and fusion proteins thereof) disclosed herein. For example, SEQ ID NO: 11 encodes a naturally occurring human ALK4 precursor polypeptide, while SEQ ID NO: 12 encodes a processed extracellular domain of ALK4. The subject nucleic acids may be single-stranded or double stranded. Such nucleic acids may be DNA or RNA molecules. These nucleic acids may be used, for example, in methods for making ALK4:ActRIIB heteromultimers as described herein.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding ALK4 and/or ActRIIB polypeptides of the present disclosure are understood to include any one of SEQ ID NOs: 7, 8, 11, 12, 21, 22, 40, 43, 71, 73, 75, 77, 79, 81, 82, or 83, as well as variants thereof. Variant nucleotide sequences include sequences that differ by one or more nucleotide substitutions, additions, or deletions including allelic variants, and therefore, will include coding sequences that differ from the nucleotide sequence designated in any one of SEQ ID NOs: 7, 8, 11, 12, 21, 22, 40, 43, 71, 73, 75, 77, 79, 81, 82, or 83.

In certain embodiments, ALK4 and/or ActRIIB polypeptides of the present disclosure are encoded by isolated or recombinant nucleic acid sequences that comprise, consist essentially of, or consists of a sequence that is least 70%, 75%, 80%, 85%, 86%, 87%, 88%, 89%, 90%, 91%, 92%, 93%, 94%, 95%, 96%, 97%, 98%, 99% or 100% identical to SEQ ID NOs: 7, 8, 11, 12, 21, 22, 40, 43, 71, 73, 75, 77, 79, 81, 82, or 83. One of ordinary skill in the art will appreciate that nucleic acid sequences that comprise, consist essentially of, or consists of a sequence complementary to a sequence that is least 70%, 75%, 80%, 85%, 86%, 87%, 88%, 89%, 90%, 91%, 92%, 93%, 94%, 95%, 96%, 97%, 98%, 99% or 100% identical to SEQ ID NOs: 7, 8, 11, 12, 21, 22, 40, 43, 71, 73, 75, 77, 79, 81, 82, or 83 also within the scope of the present disclosure. In further embodiments, the nucleic acid sequences of the disclosure can be isolated, recombinant, and/or fused with a heterologous nucleotide sequence or in a DNA library.

In other embodiments, nucleic acids of the present disclosure also include nucleotide sequences that hybridize under stringent conditions to the nucleotide sequence designated in SEQ ID NOs: 7, 8, 11, 12, 21, 22, 40, 43, 71, 73, 75, 77, 79, 81, 82, or 83, the complement sequence of SEQ ID NOs: 7, 8, 11, 12, 21, 22, 40, 43, 71, 73, 75, 77, 79, 81, 82, or 83, or fragments thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 11, 12, 21, 22, 40, 43, 71, 73, 75, 77, 79, 81, 82, or 83 to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

In certain aspects, the subject nucleic acid is provided in an expression vector comprising a nucleotide sequence encoding an ALK4 and/or ActRIIB polypeptide and operably linked to at least one regulatory sequence. Regulatory sequences are art-recognized and are selected to direct expression of ALK4 and/or ActRIIB polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a ALK4 and/or ActRIIB polypeptides. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ALK4 and/or ActRIIB polypeptides include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures [Molecular Cloning A Laboratory Manual, 3rd Ed., ed. by Sambrook, Fritsch and Maniatis Cold Spring Harbor Laboratory Press, 2001]. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ALK4 and/or ActRIIB polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ALK4 and/or ActRIIB polypeptide in cells propagated in culture, e.g., to produce proteins, including fusion proteins or variant proteins, for purification.

This disclosure also pertains to a host cell transfected with a recombinant gene including a coding sequence for one or more of the subject ALK4 and/or ActRIIB polypeptides. The host cell may be any prokaryotic or eukaryotic cell. For example, an ALK4 and/or ActRIIB polypeptide may be expressed in bacterial cells such as *E. coli*, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject ALK4 and/or ActRIIB polypeptides. For example, a host cell transfected with an expression vector encoding an ALK4 and/or ActRIIB polypeptide can be cultured under appropriate conditions to allow expression of the ALK4 and/or ActRIIB polypeptide to occur. The polypeptide may be secreted and isolated from a mixture of cells and medium containing the polypeptide. Alternatively, ALK4 and/or ActRIIB polypeptide may be isolated from a cytoplasmic or membrane fraction obtained from harvested and lysed cells. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of ALK4 and/or ActRIIB polypeptides and affinity purification with an agent that binds to a domain fused to ALK4 and/or ActRIIB polypeptide (e.g., a protein A column may be used to purify ALK4-Fc and/or ActRIIB-Fc fusion proteins). In some embodiments, the ALK4 and/or ActRIIB polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. An ALK4 and/or ActRIIB polypeptides, as well as fusion proteins thereof, may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant ALK4 and/or ActRIIB polypeptide, can allow purification of the expressed fusion protein by affinity chromatography using a $Ni^{2+}$ metal resin. The purification leader sequence can then be subsequently removed by treatment with enterokinase to provide the purified ALK4 and/or ActRIIB polypeptide, as well as heteromultimers thereof [Hochuli et al. (1987) *J. Chromatography* 411:177; and Janknecht et al. (1991) *PNAS USA* 88:8972].

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

4. ALK4:ActRIIB Antibody Antagonists

In certain aspects, the present disclosure relates to an ALK4:ActRIIB antagonist (inhibitor) that is antibody, or combination of antibodies. ALK4:ActRIIB antagonist antibody, or combination of antibodies, may bind to one or more ALK4:ActRIIB-associated ligands [e.g., GDF11, GDF8, activin (e.g., activin A, activin B, activin C, activin E, activin AB, activin AC) GDF3, BMP6, and BMP10] or one or more type I and/or type II receptors (e.g., ActRIIB and ALK4). In particular, the disclosure provides methods of using an ALK4:ActRIIB antagonist antibody, or combination of ALK4:ActRIIB antagonist antibodies, alone or in combination with one or more additional supportive therapies and/or active agents, to achieve a desired effect in a subject in need thereof (e.g., treating SMA, particularly preventing or reducing the severity of one or more complications of SMA).

In certain aspects, an ALK4:ActRIIB antagonist antibody, or combination of antibodies, of the disclosure is an antibody that inhibits at least GDF11. Therefore, in some embodiments, an ALK4:ActRIIB antagonist antibody, or combination of antibodies, binds to at least GDF11. As used herein, a GDF11 antibody (anti-GDF11 antibody) generally refers to an antibody that binds to GDF11 with sufficient affinity such that the antibody is useful as a diagnostic and/or therapeutic agent in targeting GDF11. In certain embodiments, the extent of binding of an anti-GDF11 antibody to an unrelated, non-GDF11 protein is less than about 10%, 9%, 8%, 7%, 6%, 5%, 4%, 3%, 2%, or less than about 1% of the binding of the antibody to GDF11 as measured, for example, by a radioimmunoassay (RIA), Biacore, or other protein-protein interaction or binding affinity assay. In certain embodiments, an anti-GDF11 antibody binds to an epitope of GDF11 that is conserved among GDF11 from different species. In certain preferred embodiments, an anti-GDF11 antibody binds to human GDF11. In other preferred embodiments, an anti-GDF11 antibody may inhibit GDF11 from binding to a cognate type I and/or type II receptor (e.g., ActRIIB and ALK4) and thus inhibit GDF11-mediated signaling (e.g., Smad signaling) via these receptors. It should be noted that GDF11 has high sequence homology to GDF8 and therefore antibodies that bind to GDF11, in some cases, may also bind to and/or inhibit GDF8. In some embodiments, an anti-GDF11 antibody is a multispecific antibody (e.g., bi-specific antibody) that binds to one or more additional ligands [e.g., GDF8, activin (e.g., activin A, activin B, activin C, activin E, activin AB, activin AC) GDF3, BMP6, and BMP10] and/or binds to one or more type I and/or type II receptors (e.g., ActRIIB and ALK4). In some embodiments, the disclosure relates to an antibody that binds to GDF11 and GDF8. In some embodiments, the disclosure relates to an antibody that binds GDF11 and activin A. In some embodiments, the disclosure relates to an antibody that binds GDF11 and activin B. In some embodiments, the disclosure relates to an antibody that binds GDF11, GDF8, and activin A. In some embodiments, the disclosure relates to an antibody that binds GDF11, GDF8, and activin B. In some embodiments, the disclosure relates to an antibody that binds GDF11, GDF8, activin A, and activin B. In some embodiments, the disclosure relates to combinations of antibodies, as well as uses thereof, wherein the combination of antibodies comprises an anti-GDF11 antibody and one or more additional antibodies that bind to, for example, different ligands [e.g., GDF8, activin (e.g., activin A, activin B, activin C, activin E, activin AB, activin AC) GDF3, BMP6, and BMP10] and/or bind to one or more type I and/or type II receptors (e.g., ActRIIB and ALK4). In some embodiments, the disclosure relates to a combination of antibodies comprising an antibody that binds to GDF11 and an antibody that binds to GDF8. In some embodiments, the disclosure relates to a combination of antibodies comprising an antibody that binds to GDF11 and an antibody that binds to activin A. In some embodiments, the disclosure relates to a combination of antibodies comprising an antibody that binds to GDF11 and an antibody that binds to activin B. In some embodiments, the disclosure relates to a combination of antibodies comprising an antibody that binds to GDF11, an antibody that binds to GDF8, and an antibody that binds to activin A. In some embodiments, the disclosure relates to a combination of antibodies comprising an antibody that binds to GDF11, an antibody that binds to GDF8, and an antibody that binds to activin B. In some embodiments, the disclosure relates to a combination of antibodies comprising an antibody that binds to GDF11, an antibody that binds to GDF8, an antibody that binds to activin A, and an antibody that binds to activin B.

In certain aspects, an ALK4:ActRIIB antagonist antibody, or combination of antibodies, of the disclosure is an antibody that inhibits at least GDF8. Therefore, in some embodiments, an ALK4:ActRIIB antagonist antibody, or combination of antibodies, binds to at least GDF8. As used herein, a GDF8 antibody (anti-GDF8 antibody) generally refers to an antibody that binds to GDF8 with sufficient affinity such that the antibody is useful as a diagnostic and/or therapeutic agent in targeting GDF8. In certain embodiments, the extent of binding of an anti-GDF8 antibody to an unrelated, non-GDF8 protein is less than about 10%, 9%, 8%, 7%, 6%, 5%, 4%, 3%, 2%, or less than about 1% of the binding of the antibody to GDF8 as measured, for example, by a radioimmunoassay (RIA), Biacore, or other protein-protein interaction or binding affinity assay. In certain embodiments, an anti-GDF8 antibody binds to an epitope of GDF8 that is conserved among GDF8 from different species. In certain preferred embodiments, an anti-GDF8 antibody binds to human GDF8. In other preferred embodiments, an anti-GDF8 antibody may inhibit GDF8 from binding to a cognate type I and/or type II receptor (e.g., ActRIIB and ALK4) and thus inhibit GDF8-mediated signaling (e.g., Smad signaling) via these receptors. It should be noted that GDF8 has high sequence homology to GDF11 and therefore antibodies that bind to GDF8, in some cases, may also bind to and/or inhibit GDF11. In some embodiments, an anti-GDF8 antibody is a multispecific antibody (e.g., bi-specific antibody) that binds to one or more additional ligands [e.g., GDF11, activin (e.g., activin A, activin B, activin C, activin E, activin AB, activin AC) GDF3, BMP6, and BMP10] and/or binds to one or more type I and/or type II receptors (e.g., ActRIIB and ALK4]. In some embodiments, the disclosure relates to an antibody that binds GDF8 and activin A. In some embodiments, the disclosure relates to an antibody that binds GDF8 and activin B. In some embodiments, the disclosure relates to combinations of antibodies, as well as uses thereof, wherein the combination of antibodies comprises an anti-GDF8 antibody and one or more additional antibodies that bind to, for example, different ligands [e.g., GDF11, activin (e.g., activin A, activin B, activin C, activin E, activin AB, activin AC) GDF3, BMP6, and BMP10] and/or bind to one or more type I and/or type II receptors (e.g., ActRIIB and ALK4). In some embodiments, the disclosure relates to a combination of antibodies comprising an antibody that binds to GDF8 and an antibody that binds to activin A. In some embodiments, the disclosure relates to a combination of antibodies comprising an antibody that binds to GDF8 and an antibody that binds to activin B.

In certain aspects, an ALK4:ActRIIB antagonist antibody, or combination of antibodies, of the disclosure is an antibody that inhibits at least activin (e.g., activin A, activin B, activin C, activin E, activin AB, activin AC). Therefore, in some embodiments, an ALK4:ActRIIB antagonist antibody, or combination of antibodies, binds to at least activin. As used herein, an activin antibody (anti-activin antibody) generally refers to an antibody that binds to activin with sufficient affinity such that the antibody is useful as a diagnostic and/or therapeutic agent in targeting activin. In certain embodiments, the extent of binding of an anti-activin antibody to an unrelated, non-activin protein is less than about 10%, 9%, 8%, 7%, 6%, 5%, 4%, 3%, 2%, or less than about 1% of the binding of the antibody to activin as measured, for example, by a radioimmunoassay (RIA), Biacore, or other protein-protein interaction or binding affinity assay. In certain embodiments, an anti-activin antibody binds to an epitope of activin that is conserved among activin from different species. In certain preferred embodiments, an anti-activin antibody binds to human activin. In other preferred embodiments, an anti-activin antibody may inhibit activin from binding to a cognate type I and/or type II receptor (e.g., ActRIIB and ALK4) and thus inhibit activin-mediated signaling (e.g., Smad signaling) via these receptors. It should be noted that activins share sequence homology and therefore antibodies that bind to one activin (e.g., activin A) may bind to one or more additional activins (e.g., activin B, activin AB, activin C, activin E, activin AC). In some embodiments, an anti-activin antibody binds to at least activin A and activin B. In some embodiments, an anti-activin antibody is a multispecific antibody (e.g., bi-specific antibody) that binds to one or more additional ligands [e.g., GDF11, GDF8, GDF3, BMP6, and BMP10] and/or binds to one or more type I and/or type II receptors (e.g., ActRIIB and ALK4). In some embodiments, the disclosure relates to combinations of antibodies, as well as uses thereof, wherein the combination of antibodies comprises an anti-activin antibody and one or more additional antibodies that bind to, for example, different ligands [e.g., GDF8, GDF11, GDF3, BMP6, and BMP10] and/or bind to one or more type I and/or type II receptors (e.g., ActRIIB and ALK4).

In certain aspects, an ALK4:ActRIIB antagonist antibody, or combination of antibodies, of the disclosure is an antibody that inhibits at least GDF3. Therefore, in some embodiments, an ALK4:ActRIIB antagonist antibody, or combination of antibodies, binds to at least GDF3. As used herein, a GDF3 antibody (anti-GDF3 antibody) generally refers to an antibody that binds to GDF3 with sufficient affinity such that the antibody is useful as a diagnostic and/or therapeutic agent in targeting GDF3. In certain embodiments, the extent of binding of an anti-GDF3 antibody to an unrelated, non-GDF3 protein is less than about 10%, 9%, 8%, 7%, 6%, 5%, 4%, 3%, 2%, or less than about 1% of the binding of the antibody to GDF3 as measured, for example, by a radioimmunoassay (RIA), Biacore, or other protein-protein interaction or binding affinity assay. In certain embodiments, an anti-GDF3 antibody binds to an epitope of GDF3 that is conserved among GDF3 from different species. In certain preferred embodiments, an anti-GDF3 antibody binds to human GDF3. In other preferred embodiments, an anti-GDF3 antibody may inhibit GDF3 from binding to a cognate type I and/or type II receptor (e.g., ActRIIB and ALK4) and thus inhibit GDF3-mediated signaling (e.g., Smad signaling) via these receptors. In some embodiments, an anti-GDF3 antibody is a multispecific antibody (e.g., bi-specific antibody) that binds to one or more additional ligands [e.g., GDF11, GDF8, activin (e.g., activin A, activin B, activin C, activin E, activin AB, activin AC), BMP6, and BMP10] and/or binds to one or more type I and/or type II receptors (e.g., ActRIIB and ALK4). In some embodiments, the disclosure relates to combinations of antibodies, as well as uses thereof, wherein the combination of antibodies comprises an anti-GDF3 antibody and one or more additional antibodies that bind to, for example, different ligands [e.g., GDF11, GDF8, activin (e.g., activin A, activin B, activin C, activin E, activin AB, activin AC) BMP6, and BMP10] and/or bind to one or more type I and/or type II receptors (e.g., ActRIIB and ALK4).

In certain aspects, an ALK4:ActRIIB antagonist antibody, or combination of antibodies, of the disclosure is an antibody that inhibits at least BMP6. Therefore, in some embodiments, an ALK4:ActRIIB antagonist antibody, or combination of antibodies, binds to at least BMP6. As used herein, a BMP6 antibody (anti-BMP6 antibody) generally refers to an antibody that binds to BMP6 with sufficient affinity such that the antibody is useful as a diagnostic and/or therapeutic agent in targeting BMP6. In certain embodiments, the extent of binding of an anti-BMP6 antibody to an unrelated, non-BMP6 protein is less than about 10%, 9%, 8%, 7%, 6%, 5%, 4%, 3%, 2%, or less than about 1% of the binding of the antibody to BMP6 as measured, for example, by a radioimmunoassay (RIA), Biacore, or other protein-protein interaction or binding affinity assay. In certain embodiments, an anti-BMP6 antibody binds to an epitope of BMP6 that is conserved among BMP6 from different species. In certain preferred embodiments, an anti-BMP6 antibody binds to human BMP6. In other preferred embodiments, an anti-BMP6 antibody may inhibit BMP6 from binding to a cognate type I and/or type II receptor (e.g., ActRIIB and ALK4) and thus inhibit BMP6-mediated signaling (e.g., Smad signaling) via these receptors. In some embodiments, an anti-BMP6 antibody is a multispecific antibody (e.g., bi-specific antibody) that binds to one or more additional ligands [e.g., GDF11, GDF8, activin (e.g., activin A, activin B, activin C, activin E, activin AB, activin AC), GDF3, and BMP10] and/or binds to one or more type I and/or type II receptors (e.g., ActRIIB and ALK4). In some embodiments, the disclosure relates to combinations of antibodies, as well as uses thereof, wherein the combination of antibodies comprises an anti-BMP6 antibody and one or more additional antibodies that bind to, for example, different ligands [e.g., GDF11, GDF8, activin (e.g., activin A, activin B, activin C, activin E, activin AB, activin AC) GDF3, and BMP10] and/or bind to one or more type I and/or type II receptors (e.g., ActRIIB and ALK4).

In certain aspects, an ALK4:ActRIIB antagonist antibody, or combination of antibodies, of the disclosure is an antibody that inhibits at least BMP10. Therefore, in some embodiments, an ALK4:ActRIIB antagonist antibody, or combination of antibodies, binds to at least BMP10. As used herein, a BMP10 antibody (anti-BMP10 antibody) generally refers to an antibody that binds to BMP10 with sufficient affinity such that the antibody is useful as a diagnostic and/or therapeutic agent in targeting BMP10. In certain embodiments, the extent of binding of an anti-BMP10 antibody to an unrelated, non-BMP10 protein is less than about 10%, 9%, 8%, 7%, 6%, 5%, 4%, 3%, 2%, or less than about 1% of the binding of the antibody to BMP10 as measured, for example, by a radioimmunoassay (RIA), Biacore, or other protein-protein interaction or binding affinity assay. In certain embodiments, an anti-BMP10 antibody binds to an epitope of BMP10 that is conserved among BMP10 from different species. In certain preferred embodiments, an anti-BMP10 antibody binds to human BMP10. In other preferred embodiments, an anti-BMP10 antibody may inhibit BMP10 from binding to a cognate type I and/or type II receptor (e.g., ActRIIB and ALK4) and thus inhibit BMP10-mediated signaling (e.g., Smad signaling) via these receptors. In some embodiments, an anti-BMP10 antibody is a multispecific antibody (e.g., bi-specific antibody) that binds to one or more additional ligands [e.g., GDF11, GDF8, activin (e.g., activin A, activin B, activin C, activin E, activin AB, activin AC), GDF3, and BMP6] and/or binds to one or more type I and/or type II receptors (e.g., ActRIIB and ALK4). In some embodiments, the disclosure relates to combinations of antibodies, as well as uses thereof, wherein the combination of antibodies comprises an anti-BMP10 antibody and one or more additional antibodies that bind to, for example, different ligands [e.g., GDF11, GDF8, activin (e.g., activin A, activin B, activin C, activin E, activin AB, activin AC) GDF3, and BMP6] and/or bind to one or more type I and/or type II receptors (e.g., ActRIIB and ALK4).

In other aspects, an ALK4:ActRIIB antagonist antibody, or combination of antibodies, of the disclosure is an antibody that inhibits at least ActRIIB Therefore, in some embodiments, an ActRII antagonist antibody, or combination of antibodies, binds to at least ActRIIB As used herein, an ActRIIB antibody (anti-ActRIIB antibody) generally refers to an antibody that binds to ActRIIB with sufficient affinity such that the antibody is useful as a diagnostic and/or therapeutic agent in targeting ActRIIB In certain embodiments, the extent of binding of an anti-ActRIIB antibody to an unrelated, non-ActRIIB protein is less than about 10%, 9%, 8%, 7%, 6%, 5%, 4%, 3%, 2%, or less than about 1% of the binding of the antibody to ActRIIB as measured, for example, by a radioimmunoassay (RIA), Biacore, or other protein-protein interaction or binding affinity assay. In certain embodiments, an anti-ActRIIB antibody binds to an epitope of ActRIIB that is conserved among ActRIIB from different species. In certain preferred embodiments, an anti-ActRIIB antibody binds to human ActRIIB In other preferred embodiments, an anti-ActRIIB antibody may inhibit one or more ligands [e.g., GDF8, activin (e.g., activin A, activin B, activin C, activin E, activin AB, activin AC) GDF3, BMP6, and BMP10] from binding to ActRIIB It should be noted that ActRIIB has sequence homology to ActRIIA and therefore antibodies that bind to ActRIIB, in some cases, may also bind to and/or inhibit ActRIIA. In some embodiments, an anti-ActRIIB antibody is a multispecific antibody (e.g., bi-specific antibody) that binds to ActRIIB and one or more ligands [e.g., GDF8, activin (e.g., activin A, activin B, activin C, activin E, activin AB, activin AC) GDF3, BMP6, and BMP10]. In some embodiments, an anti-ActRIIB antibody is a multispecific antibody (e.g., bi-specific antibody) that binds to ActRIIB and ALK4. In some embodiments, the disclosure relates to combinations of antibodies, as well as uses thereof, wherein the combination of antibodies comprises at least an anti-ActRIIB antibody and at least an ALK4 antibody. In some embodiments, the disclosure relates to combinations of antibodies, as well as uses thereof, wherein the combination of antibodies comprises an anti-ActRIIB antibody and one or more additional antibodies that bind to, for example, one or more ligands [e.g., GDF8, activin (e.g., activin A, activin B, activin C, activin E, activin AB, activin AC) GDF3, BMP6, and BMP10] and ALK4.

In certain aspects, an ALK4:ActRIIB antagonist antibody, or combination of antibodies, of the disclosure is an antibody that inhibits at least ALK4. Therefore, in some embodiments, an ALK4:ActRIIB antagonist antibody, or combination of antibodies, binds to at least ALK4. As used herein, an ALK4 antibody (anti-ALK4 antibody) generally refers to an antibody that binds to ALK4 with sufficient affinity such that the antibody is useful as a diagnostic and/or therapeutic agent in targeting ALK4. In certain embodiments, the extent of binding of an anti-ALK4 antibody to an unrelated, non-ALK4 protein is less than about 10%, 9%, 8%, 7%, 6%, 5%, 4%, 3%, 2%, or less than about 1% of the binding of the antibody to ALK4 as measured, for example, by a radioimmunoassay (RIA), Biacore, or other protein-protein interaction or binding affinity assay. In certain embodiments, an anti-ALK4 antibody binds to an epitope of ALK4 that is conserved among ALK4 from different species. In certain preferred embodiments, an anti-ALK4 antibody binds to human ALK4. In other preferred embodiments, an anti-ALK4 antibody may inhibit one or more ligands [e.g., GDF8, activin (e.g., activin A, activin B, activin C, activin E, activin AB, activin AC) GDF3, BMP6, BMP10, and BMP9] from binding to ALK4. In some embodiments, an anti-ALK4 antibody is a multispecific antibody (e.g., bi-specific antibody) that binds to ALK4 and one or more ligands [e.g., GDF8, activin (e.g., activin A, activin B, activin C, activin E, activin AB, activin AC) GDF3, BMP6, and BMP10] and/or ActRIIB In some embodiments, the disclosure relates to combinations of antibodies, as well as uses thereof, wherein the combination of antibodies comprises an anti-ALK4 antibody and one or more additional antibodies that bind to, for example, one or more ligands [e.g., GDF8, activin (e.g., activin A, activin B, activin C, activin E, activin AB, activin AC) GDF3, BMP6, and BMP10] and/or ALK4.

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g., scFv); and multispecific antibodies formed from antibody fragments. See, e.g., Hudson et al. (2003) Nat. Med. 9:129-134; Plückthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894, 5,587,458, and 5,869,046. Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In preferred embodiments, the antibodies of the present disclosure are isolated antibodies.

Diabodies are antibody fragments with two antigen-binding sites that may be bivalent or bispecific. See, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448. Triabodies and tetrabodies are also described in Hudson et al. (2003) Nat. Med. 9:129-134.

Single-domain antibodies are antibody fragments comprising all or a portion of the heavy-chain variable domain or all or a portion of the light-chain variable domain of an antibody. In certain embodiments, a single-domain antibody is a human single-domain antibody. See, e.g., U.S. Pat. No. 6,248,516.

Antibody fragments can be made by various techniques, including but not limited to proteolytic digestion of an intact antibody as well as production by recombinant host cells (e.g., *E. coli* or phage), as described herein.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, $IgG_1$, $IgG_2$, $IgG_3$, $IgG_4$, $IgA_1$, and $IgA_2$. The heavy-chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a $K_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, surface plasmon resonance (Biacore™ assay), radiolabeled antigen binding assay (RIA), and ELISA. In some embodiments, antibodies of the present disclosure bind to their target antigens [e.g., ActRIIB ALK4, GDF8, activin (e.g., activin A, activin B, activin C, activin E, activin AB, activin AC) GDF3, BMP6, and BMP10] with at least a $K_D$ of $1\times10^{-7}$ or stronger, $1\times10^{-8}$ or stronger, $1\times10^{-9}$ or stronger, $1\times10^{-10}$ or stronger, $1\times10^{-11}$ or stronger, $1\times10^{-12}$ or stronger, $1\times10^{-13}$ or stronger, or $1\times10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radiolabeled antigen (e.g., $^{125}$I-labeled) in the presence of a titration series of unlabeled antigen, then capturing bound antigen with an anti-Fab antibody-coated plate [see, e.g., Chen et al. (1999) J. Mol. Biol. 293:865-881]. To establish conditions for the assay, multi-well plates (e.g., MICROTITER® from Thermo Scientific) are coated (e.g., overnight) with a capturing anti-Fab antibody (e.g., from Cappel Labs) and subsequently blocked with bovine serum albumin, preferably at room temperature (e.g., approximately 23° C.). In a non-adsorbent plate, radiolabeled antigen are mixed with serial dilutions of a Fab of interest [e.g., consistent with assessment of the anti-VEGF antibody, Fab-12, in Presta et al., (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE® 3000 (Biacore, Inc., Piscataway, N.J.) with immobilized antigen CM5 chips at about 10 response units (RU). Briefly, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NHS) according to the supplier's instructions. For example, an antigen can be diluted with 10 mM sodium acetate, pH 4.8, to 5 μg/ml (about 0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at at a flow rate of approximately 25 μl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. [see, e.g., Chen et al., (1999) J. Mol. Biol. 293:865-881]. If the on-rate exceeds, for example, $10^6$ $M^{-1}$ $s^{-1}$ by the surface plasmon resonance assay above, then the on-rate can be determined by using a fluorescent quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophometer (Aviv Instruments) or a 8000-series SLM-AMINCO® spectrophotometer (ThermoSpectronic) with a stirred cuvette.

The nucleic acid and amino acid sequences of human ActRIIB ALK4, GDF8, activin (e.g., activin A, activin B, activin C, activin E, activin AB, activin AC) GDF3, BMP6, and BMP10 are well known in the art and thus antibody antagonists for use in accordance with this disclosure may be routinely made by the skilled artisan based on the knowledge in the art and teachings provided herein.

In certain embodiments, an antibody provided herein is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) Proc. Natl. Acad. Sci. USA, 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

Humanized antibodies and methods of making them are reviewed, for example, in Almagro and Fransson (2008) Front. Biosci. 13:1619-1633 and are further described, for example, in Riechmann et al., (1988) Nature 332:323-329; Queen et al. (1989) Proc. Nat'l Acad. Sci. USA 86:10029-10033; U.S. Pat. Nos. 5,821,337, 7,527,791, 6,982,321, and 7,087,409; Kashmiri et al., (2005) Methods 36:25-34 [describing SDR (a-CDR) grafting]; Padlan, Mol. Immunol. (1991) 28:489-498 (describing "resurfacing"); Dall'Acqua et al. (2005) Methods 36:43-60 (describing "FR shuffling"); Osbourn et al. (2005) Methods 36:61-68; and Klimka et al. Br. J. Cancer (2000) 83:252-260 (describing the "guided selection" approach to FR shuffling).

Human framework regions that may be used for humanization include but are not limited to: framework regions selected using the "best-fit" method [see, e.g., Sims et al. (1993) J. Immunol. 151:2296]; framework regions derived from the consensus sequence of human antibodies of a particular subgroup of light-chain or heavy-chain variable regions [see, e.g., Carter et al. (1992) Proc. Natl. Acad. Sci. USA, 89:4285; and Presta et al. (1993) J. Immunol., 151: 2623]; human mature (somatically mutated) framework regions or human germline framework regions [see, e.g., Almagro and Fransson (2008) Front. Biosci. 13:1619-1633]; and framework regions derived from screening FR libraries [see, e.g., Baca et cd., (1997) J. Biol. Chem. 272:10678-10684; and Rosok et cd., (1996) J. Biol. Chem. 271:22611-22618].

In certain embodiments, an antibody provided herein is a human antibody. Human antibodies can be produced using various techniques known in the art. Human antibodies are described generally in van Dijk and van de Winkel (2001) Curr. Opin. Pharmacol. 5: 368-74 and Lonberg (2008) Curr. Opin. Immunol. 20:450-459.

Human antibodies may be prepared by administering an immunogen [e.g., ActRIIB, ALK4, GDF8, activin (e.g., activin A, activin B, activin C, activin E, activin AB, activin AC) GDF3, BMP6, and BMP10] to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals, see, for example, Lonberg (2005) Nat. Biotechnol. 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE® technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described [see, e.g., Kozbor J. Immunol., (1984) 133: 3001; Brodeur et al. (1987) Monoclonal Antibody Production Techniques and Applications, pp. 51-63, Marcel Dekker, Inc., New York; and Boerner et al. (1991) J. Immunol., 147: 86]. Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, Xiandai Mianyixue (2006) 26(4):265-268 (2006) (describing human-human hybridomas). Human hybridoma technology (Trioma technology) is also described in Vollmers and Brandlein (2005) Histol. Histopathol., 20(3):927-937 (2005) and Vollmers and Brandlein (2005) Methods Find Exp. Clin. Pharmacol., 27(3):185-91.

Human antibodies provided herein may also be generated by isolating Fv clone variable-domain sequences selected from human-derived phage display libraries. Such variable-domain sequences may then be combined with a desired human constant domain. Techniques for selecting human antibodies from antibody libraries are described herein.

For example, antibodies of the present disclosure may be isolated by screening combinatorial libraries for antibodies with the desired activity or activities. A variety of methods are known in the art for generating phage-display libraries and screening such libraries for antibodies possessing the desired binding characteristics. Such methods are reviewed, for example, in Hoogenboom et al. (2001) in Methods in Molecular Biology 178:1-37, O'Brien et al., ed., Human Press, Totowa, N.J. and further described, for example, in the McCafferty et al. (1991) Nature 348:552-554; Clackson et al., (1991) Nature 352: 624-628; Marks et al. (1992) J. Mol. Biol. 222:581-597; Marks and Bradbury (2003) in Methods in Molecular Biology 248:161-175, Lo, ed., Human Press, Totowa, N.J.; Sidhu et al. (2004) J. Mol. Biol. 338(2):299-310; Lee et al. (2004) J. Mol. Biol. 340(5):1073-1093; Fellouse (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen [e.g., ActRIIB ALK4, GDF8, activin (e.g., activin A, activin B, activin C, activin E, activin AB, activin AC) GDF3, BMP6, and BMP10] without the requirement of constructing hybridomas. Alternatively, the naive repertoire can be cloned (e.g., from human) to provide a single source of antibodies directed against a wide range of non-self and also self-antigens without any immunization as described by Griffiths et al. (1993) EMBO J, 12: 725-734. Finally, naive libraries can also be made synthetically by cloning un-rearranged V-gene segments from stem cells and using PCR primers containing random sequence to encode the highly variable CDR3 regions and to accomplish rearrangement in vitro, as described by Hoogenboom and Winter (1992) J. Mol. Biol., 227: 381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In certain embodiments, an antibody provided herein is a multispecific antibody, for example, a bispecific antibody. Multispecific antibodies (typically monoclonal antibodies) have binding specificities for at least two different epitopes (e.g., two, three, four, five, or six or more) on one or more (e.g., two, three, four, five, six or more) antigens.

Engineered antibodies with three or more functional antigen binding sites, including "octopus antibodies," are also included herein (see, e.g., US 2006/0025576A1).

In certain embodiments, the antibodies disclosed herein are monoclonal antibodies. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from GDF11, anti-protein/anti-peptide antisera or monoclonal antibodies can be made by standard protocols [see, e.g., Antibodies: A Laboratory Manual (1988) ed. by Harlow and Lane, Cold Spring Harbor Press]. A mammal, such as a mouse, hamster, or rabbit can be immunized with an immunogenic form of the GDF11 polypeptide, an antigenic fragment which is capable of eliciting an antibody response, or a fusion protein. Techniques for conferring immunogenicity on a protein or peptide include conjugation to carriers or other techniques well known in the art. An immunogenic portion of a GDF11 polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of GDF11, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique [see, e.g., Kohler and Milstein (1975) Nature, 256: 495-497], the human B cell hybridoma technique [see, e.g., Kozbar et al. (1983) Immunology Today, 4:72], and the EBV-hybridoma technique to produce human monoclonal antibodies [Cole et al. (1985) Monoclonal Antibodies and Cancer Therapy, Alan R. Liss, Inc. pp. 77-96]. Hybridoma cells can be screened immunochemically for production of antibodies specifically reactive with a GDF11 polypeptide, and monoclonal antibodies isolated from a culture comprising such hybridoma cells.

In certain embodiments, one or more amino acid modifications may be introduced into the Fc region of an antibody provided herein thereby generating an Fc-region variant. The Fc-region variant may comprise a human Fc-region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet for which certain effector functions [e.g., complement-dependent cytotoxicity (CDC) and antibody-dependent cellular cytotoxicity (ADCC)] are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in, for example, Ravetch and Kinet (1991) Annu. Rev. Immunol. 9:457-492. Non-limiting examples of in vitro assays to assess ADCC activity of a molecule of interest are described in U.S. Pat. No. 5,500,362; Hellstrom, I. et al. (1986) Proc. Nat'l Acad. Sci. USA 83:7059-7063; Hellstrom, I et al. (1985) Proc. Nat'l Acad. Sci. USA 82:1499-1502; U.S. Pat. No. 5,821,337; and Bruggemann, M. et al. (1987) J. Exp. Med. 166:1351-1361. Alternatively, non-radioactive assay methods may be employed (e.g., ACTI™, non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) Proc. Nat'l Acad. Sci. USA 95:652-656. C1q binding assays may also be carried out to confirm that the antibody is unable to bind C1q and hence lacks CDC activity [see, e.g., C1q and C3c binding ELISA in WO 2006/029879 and WO 2005/100402]. To assess complement activation, a CDC assay may be performed [see, e.g., Gazzano-Santoro et al. (1996) J. Immunol. Methods 202:163; Cragg, M. S. et al. (2003) Blood 101:1045-1052; and Cragg, M. S, and M. J. Glennie (2004) Blood 103:2738-2743]. FcRn binding and in vivo clearance/half-life determinations can also be performed using methods known in the art [see, e.g., Petkova, S. B. et al. (2006) Int. Immunol. 18(12):1759-1769].

Antibodies of the present disclosure with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine-engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy-chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into, and/or substitutions of residues within, the amino acid sequences of the antibody and/or binding polypeptide. Any combination of deletion, insertion, and substitution can be made to arrive at the final construct, provided that the final construct possesses the desired characteristics, e.g., target-binding (ActRIIB, ALK4, GDF8, activin (e.g., activin A, activin B, activin C, activin E, activin AB, activin AC) GDF3, BMP6, and BMP10 binding).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury (2008) Methods Mol. Biol. 207:179-196 (2008)), and/or SDRs (a-CDRs), with the resulting variant VH or VL being tested for binding affinity. Affinity maturation by constructing and reselecting from secondary libraries has been described in the art [see, e.g., Hoogenboom et al., in Methods in Molecular Biology 178:1-37, O'Brien et al., ed., Human Press, Totowa, N.J., (2001)]. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two, or three amino acid substitutions.

A useful method for identification of residues or regions of the antibody and/or the binding polypeptide that may be targeted for mutagenesis is called "alanine scanning mutagenesis", as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody or binding polypeptide with antigen is affected. Further substitutions may be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues may be targeted or eliminated as candidates for substitution. Variants may be screened to determine whether they contain the desired properties.

Amino-acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional non-proteinaceous moieties that are known in the art and readily available. The moieties suitable for derivatization of the antibody and/or binding polypeptide include but are not limited to water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

5. Small Molecule Antagonists

In other aspects, the present disclosure relates to an ALK4:ActRIIB antagonist (inhibitor) that is small molecule, or combination of small molecules. ALK4:ActRIIB antagonist small molecules may inhibit to one or more ALK4:ActRIIB-associated ligands [e.g., GDF11, GDF8, activin (e.g., activin A, activin B, activin C, activin E, activin AB, activin AC) GDF3, BMP6, and BMP10], one or more type I and/or type II receptors (e.g., ActRIIB and ALK4), or one or more downstream signaling components (e.g., Smads 2 and/or 3). In particular, the disclosure provides methods of using an ALK4:ActRIIB antagonist small molecules, or combination of ALK4:ActRIIB antagonist small molecules, alone or in combination with one or more additional supportive therapies and/or active agents, to achieve a desired effect in a subject in need thereof (e.g., treating SMA, particularly preventing or reducing the severity of one or more complication of SMA).

In some embodiments, an ALK4:ActRIIB antagonist is a small molecule antagonist, or combination of small molecule antagonists, that inhibits at least GDF11. In some embodiments, a small molecule antagonist, or combination of small molecule antagonists, that inhibits GDF11 further inhibits one or more ligands [e.g., GDF8, activin (e.g., activin A, activin B, activin C, activin E, activin AB, activin AC), GDF3, BMP6, and BMP10], ALK4 and/or ActRIIB In some embodiments, an ALK4:ActRIIB antagonist is a small molecule antagonist, or combination of small molecule antagonists, that inhibits at least GDF8. In some embodiments, a small molecule antagonist, or combination of small molecule antagonists, that inhibits GDF8 further inhibits one or more ligands [e.g., GDF11, activin (e.g., activin A, activin B, activin C, activin E, activin AB, activin AC), GDF3, BMP6, and BMP10], ALK4 and/or ActRIIB In some embodiments, an ALK4:ActRIIB antagonist is a small molecule antagonist, or combination of small molecule antagonists, that inhibits at least activin (e.g., activin A, activin B, activin C, activin E, activin AB, and activin AE). In some embodiments, a small molecule antagonist, or combination of small molecule antagonists, that inhibits activin further inhibits one or more ligands [e.g., GDF11, GDF8, GDF3, BMP6, and BMP10], ActRIIB, and/or ALK4. In some embodiments, an ALK4:ActRIIB antagonist is a small molecule antagonist, or combination of small molecule antagonists, that inhibits at least GDF3. In some embodiments, a small molecule antagonist, or combination of small molecule antagonists, that inhibits GDF3 further inhibits one or more ligands [e.g., GDF11, GDF8, activin (e.g., activin A, activin B, activin C, activin E, activin AB, activin AC), BMP6, and/or BMP10], ActRIIB, and/or ALK4. In some embodiments, an ALK4:ActRIIB antagonist is a small molecule antagonist, or combination of small molecule antagonists, that inhibits at least BMP6. In some embodiments, a small molecule antagonist, or combination of small molecule antagonists, that inhibits BMP6 further inhibits one or more ligands [e.g., GDF11, GDF8, activin (e.g., activin A, activin B, activin C, activin E, activin AB, activin AC), GDF3, and/or BMP10], ActRIIB, and/or ALK4. In some embodiments, an ALK4:ActRIIB antagonist is a small molecule antagonist, or combination of small molecule antagonists, that inhibits at least BMP10. In some embodiments, a small molecule antagonist, or combination of small molecule antagonists, that inhibits BMP10 further inhibits one or more ligands [e.g., GDF11, GDF8, activin (e.g., activin A, activin B, activin C, activin E, activin AB, activin AC), GDF3, and BMP6], ActRIIB, and/or ALK4. In some embodiments, an ALK4:ActRIIB antagonist is a small molecule antagonist, or combination of small molecule antagonists, that inhibits at least ActRIIB In some embodiments, a small molecule antagonist, or combination of small molecule antagonists, that inhibits ActRIIB further inhibits one or more ligands [e.g., GDF11, GDF8, activin (e.g., activin A, activin B, activin C, activin E, activin AB, activin AC), GDF3, BMP6, and/or BMP10] and/or ALK4. In some embodiments, an ActRII antagonist is a small molecule antagonist, or combination of small molecule antagonists, that inhibits at least ALK4. In some embodiments, a small molecule antagonist, or combination of small molecule antagonists, that inhibits ALK4 further inhibits one or more ligands [e.g., GDF11, GDF8, activin (e.g., activin A, activin B, activin C, activin E, activin AB, activin AC), GDF3, BMP6, and BMP10] and/or ActRIIB.

Small molecule antagonists can be direct or indirect inhibitors. For example, an indirect small molecule antagonist, or combination of small molecule antagonists, may inhibit the expression (e.g., transcription, translation, cellular secretion, or combinations thereof) of at least one or more ligands [e.g., GDF8, activin (e.g., activin A, activin B, activin C, activin E, activin AB, activin AC) GDF3, BMP6, and/or BMP10], one or more type I and/or type II receptors (e.g., ActRIIB and ALK4), or one or more ActRII downstream signaling components (e.g., Smads 2 and/or 3). Alternatively, a direct small molecule ALK4:ActRIIB antagonist, or combination of small molecule antagonists, may directly bind to, for example, one or more of one or more ligands [e.g., GDF8, activin (e.g., activin A, activin B, activin C, activin E, activin AB, activin AC) GDF3, BMP6, and BMP10], one or more type I and/or type II receptors (e.g., ActRIIB and ALK4), or one or more ActRII downstream signaling components (e.g., Smads 2 and/or 3). Combinations of one or more indirect and one or more direct small molecule antagonists may be used in accordance with the methods disclosed herein.

Binding organic small molecule antagonists of the present disclosure may be identified and chemically synthesized using known methodology (see, e.g., PCT Publication Nos. WO 00/00823 and WO 00/39585). In general, small molecule antagonists of the disclosure are usually less than about 2000 daltons in size, alternatively less than about 1500, 750, 500, 250 or 200 daltons in size, wherein such organic small molecules that are capable of binding, preferably specifically, to a polypeptide as described herein. Such small molecule antagonists may be identified without undue experimentation using well-known techniques. In this regard, it is noted that techniques for screening organic small molecule libraries for molecules that are capable of binding to a polypeptide target are well-known in the art (see, e.g., international patent publication Nos. WO00/00823 and WO00/39585).

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, and acid chlorides.

6. Nucleotide Antagonists

In other aspects, the present disclosure relates to an ALK4:ActRIIB antagonist (inhibitor) that is a polynucleotide, or combination of polynucleotides. ALK4:ActRIIB antagonist polynucleotides may inhibit to one or more ALK4:ActRIIB-associated ligands [e.g., GDF11, GDF8, activin (e.g., activin A, activin B, activin C, activin E, activin AB, activin AC) GDF3, BMP6, and BMP10], one or more type I and/or type II receptors (e.g., ActRIIB and ALK4), or one or more downstream signaling components (e.g., Smads 2 and/or 3). In particular, the disclosure provides methods of using an ALK4:ActRIIB antagonist polynucleotide, or combination of ALK4:ActRIIB antagonist polynucleotides, alone or in combination with one or more additional supportive therapies and/or active agents, to achieve a desired effect in a subject in need thereof (e.g., treating SMA, particularly preventing or reducing the severity of one or more complications of SMA).

In some embodiments, an ALK4:ActRIIB antagonist is a polynucleotide antagonist, or combination of polynucleotide antagonists, that inhibits at least GDF11. In some embodiments, a polynucleotide antagonist, or combination of polynucleotide antagonists, that inhibits GDF11 further inhibits one or more ligand [e.g., GDF8, activin (e.g., activin A, activin B, activin C, activin E, activin AB, activin AC), GDF3, BMP6, and BMP10], ActRIIB, and/or ALK4. In some embodiments, an ALK4:ActRIIB antagonist is a polynucleotide antagonist, or combination of polynucleotide antagonists, that inhibits at least GDF8. In some embodiments, a polynucleotide antagonist, or combination of polynucleotide antagonists, that inhibits GDF8 further inhibits one or more ligand [e.g., GDF11, activin (e.g., activin A, activin B, activin C, activin E, activin AB, activin AC), GDF3, BMP6, and BMP10], ActRIIB, and/or ALK4. In some embodiments, an ALK4:ActRIIB antagonist is a polynucleotide antagonist, or combination of polynucleotide antagonists, that inhibits at least activin (e.g., activin A, activin B, activin C, activin E, activin AB, and activin AE). In some embodiments, a polynucleotide antagonist, or combination of polynucleotide antagonists, that inhibits activin further inhibits one or more ligand [e.g., GDF11, GDF8, GDF3, BMP6, and BMP10], ActRIIB, and/or ALK4. In some embodiments, an ALK4:ActRIIB polynucleotide is a polynucleotide antagonist, or combination of polynucleotide antagonists, that inhibits at least GDF3. In some embodiments, a polynucleotide, or combination of polynucleotide antagonists, that inhibits GDF3 further inhibits one or more ligand [e.g., GDF11, GDF8, activin (e.g., activin A, activin B, activin C, activin E, activin AB, activin AC), BMP6, and BMP10], ActRIIB, and/or ALK4. In some embodiments, an ALK4:ActRIIB antagonist is a polynucleotide antagonist, or combination of polynucleotide antagonists, that inhibits at least BMP6. In some embodiments, a polynucleotide antagonist, or combination of polynucleotide antagonists, that inhibits BMP6 further inhibits one or more ligand [e.g., GDF11, GDF8, activin (e.g., activin A, activin B, activin C, activin E, activin AB, activin AC), GDF3, and BMP10], ActRIIB, and/or ALK4. In some embodiments, an ALK4:ActRIIB antagonist is a polynucleotide antagonist, or combination of polynucleotide antagonists, that inhibits at least BMP10. In some embodiments, a polynucleotide antagonist, or combination of polynucleotide antagonists, that inhibits BMP10 further inhibits one or more ligand [e.g., GDF11, GDF8, activin (e.g., activin A, activin B, activin C, activin E, activin AB, activin AC), GDF3, and BMP6], ActRIIB, and/or ALK4. In some embodiments, an ActRII antagonist is a polynucleotide antagonist, or combination of polynucleotide antagonists, that inhibits at least ActRIIB In some embodiments, a polynucleotide antagonist, or combination of polynucleotide antagonists, that inhibits ActRIIB further inhibits one or more ligand [e.g., GDF11, GDF8, activin (e.g., activin A, activin B, activin C, activin E, activin AB, activin AC), GDF3, BMP6, and BMP10] and/or ALK4. In some embodiments, an ALK4:ActRIIB antagonist is a polynucleotide antagonist, or combination of polynucleotide antagonists, that inhibits at least ALK4. In some embodiments, a polynucleotide antagonist, or combination of polynucleotide antagonists, that inhibits ALK4 further inhibits one or more ligand [e.g., GDF11, GDF8, activin (e.g., activin A, activin B, activin C, activin E, activin AB, activin AC), GDF3, BMP6, and BMP10] and/or ActRIIB The polynucleotide antagonists of the present disclosure may be an antisense nucleic acid, an RNAi molecule [e.g., small interfering RNA (siRNA), small-hairpin RNA (shRNA), microRNA (miRNA)], an aptamer and/or a ribozyme. The nucleic acid and amino acid sequences of human ALK4, ActRIIB, GDF11, GDF8, activin (e.g., activin A, activin B, activin C, activin E, activin AB, activin AC) GDF3, BMP6, and BMP10 are known in the art and thus polynucleotide antagonists for use in accordance with methods of the present disclosure may be routinely made by the skilled artisan based on the knowledge in the art and teachings provided herein.

For example, antisense technology can be used to control gene expression through antisense DNA or RNA, or through triple-helix formation. Antisense techniques are discussed, for example, in Okano (1991) J. Neurochem. 56:560; Oligodeoxynucleotides as Antisense Inhibitors of Gene Expression, CRC Press, Boca Raton, Fla. (1988). Triple helix formation is discussed in, for instance, Cooney et al. (1988) Science 241:456; and Dervan et al., (1991) Science 251: 1300. The methods are based on binding of a polynucleotide to a complementary DNA or RNA. In some embodiments, the antisense nucleic acids comprise a single-stranded RNA or DNA sequence that is complementary to at least a portion of an RNA transcript of a desired gene. However, absolute complementarity, although preferred, is not required.

A sequence "complementary to at least a portion of an RNA," referred to herein, means a sequence having sufficient complementarity to be able to hybridize with the RNA, forming a stable duplex; in the case of double-stranded antisense nucleic acids of a gene disclosed herein, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well [see, e.g., Wagner, R., (1994) Nature 372:333-335]. Thus, oligonucleotides complementary to either the 5'- or 3'-untranslated, noncoding regions of a gene of the disclosure, could be used in an antisense approach to inhibit translation of an endogenous mRNA. Polynucleotides complementary to the 5'-untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-untranslated, 3'-untranslated, or coding regions of an mRNA of the disclosure, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

In one embodiment, the antisense nucleic acid of the present disclosure is produced intracellularly by transcription from an exogenous sequence. For example, a vector or a portion thereof, is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the SV40 early promoter region [see, e.g., Benoist and Chambon (1981) Nature 29:304-310], the promoter contained in the 3' long terminal repeat of Rous sarcoma virus [see, e.g., Yamamoto et al. (1980) Cell 22:787-797], the herpes thymidine promoter [see, e.g., Wagner et al. (1981) Proc. Natl. Acad. Sci. U.S.A. 78:1441-1445], and the regulatory sequences of the metallothionein gene [see, e.g., Brinster, et al. (1982) Nature 296:39-42].

In some embodiments, the polynucleotide antagonists are interfering RNA or RNAi molecules that target the expression of one or more genes. RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double-stranded RNA duplex of 10 to 50 nucleotides in length, which interferes with the expression of a target gene which is sufficiently complementary (e.g. at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short-hairpin RNA (shRNA); also short-interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. [Genes & Dev. (2002) 16:948-958, 2002] have used small RNA molecules folded into hairpins as a means to effect RNAi. Accordingly, such short hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double-stranded RNA (dsRNA) products of the DICER RNase and, in any event, have the same capacity for inhibiting expression of a specific gene. The shRNA can be expressed from a lentiviral vector. An miRNA is a single-stranded RNA of about 10 to 70 nucleotides in length that are initially transcribed as pre-miRNA characterized by a "stem-loop" structure and which are subsequently processed into mature miRNA after further processing through the RISC.

Molecules that mediate RNAi, including without limitation siRNA, can be produced in vitro by chemical synthesis (Hohjoh, FEBS Lett 521:195-199, 2002), hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as *E. coli* RNase III (Yang et al., Proc Natl Acad Sci USA 99:9942-9947, 2002).

According to another aspect, the disclosure provides polynucleotide antagonists including but not limited to, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof.

In some embodiments, the polynucleotide antagonists of the disclosure are aptamers. Aptamers are nucleic acid molecules, including double-stranded DNA and single-stranded RNA molecules, which bind to and form tertiary structures that specifically bind to a target molecule, such as a ALK4, ActRIIB, GDF11, GDF8, activin (e.g., activin A, activin B, activin C, activin E, activin AB, activin AC) GDF3, BMP6, and/or BMP10 polypeptide. The generation and therapeutic use of aptamers are well established in the art. See, e.g., U.S. Pat. No. 5,475,096. Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096, 5,580,737, 5,567,588, 5,707,796, 5,763,177, 6,011,577, and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Typically, such binding molecules are separately administered to the animal [see, e.g., O'Connor (1991) J. Neurochem. 56:560], but such binding molecules can also be expressed in vivo from polynucleotides taken up by a host cell and expressed in vivo [see, e.g., Oligodeoxynucleotides as Antisense Inhibitors of Gene Expression, CRC Press, Boca Raton, Fla. (1988)].

7. Screening Assays

In certain aspects, the present disclosure relates to the use of ALK4:ActRIIB heteromultimers to identify compounds (agents) which are ALK4:ActRIIB antagonists. Compounds identified through this screening can be tested to assess their ability to modulate tissues such as bone and muscle, to assess their ability to modulate tissue growth in vivo or in vitro. These compounds can be tested, for example, in animal models (SMA models of disease).

There are numerous approaches to screening for therapeutic agents for modulating tissue growth by targeting TGFβ superfamily ligand signaling (e.g., SMAD signaling). In certain embodiments, high-throughput screening of compounds can be carried out to identify agents that perturb TGFβ superfamily receptor-mediated effects on a selected cell line. In certain embodiments, the assay is carried out to screen and identify compounds that specifically inhibit or reduce binding of an ALK4:ActRIIB heteromultimer to a binding partner including for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGβ31, TGβ32, TGβ33, activin A, activin B, activin AB, activin AC, nodal, glial cell-derived neurotrophic factor (GDNF), neurturin, artemin, persephin, MIS, and Lefty. Alternatively, the assay can be used to identify compounds that enhance binding of an AALK4:ActRIIB heteromultimer to a binding partner such as a ligand. In a further embodiment, the compounds can be identified by their ability to interact with an ALK4:ActRIIB heteromultimer.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S-transferase (GST), photoactivatible crosslinkers or any combinations thereof.

In many drug-screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ALK4:ActRIIB heteromultimer to a binding partner including for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGβ31, TGβ32, TGβ33, activin A, activin B, activin AB, activin AC, nodal, glial cell-derived neurotrophic factor (GDNF), neurturin, artemin, persephin, MIS, and Lefty.

Merely to illustrate, in an exemplary screening assay of the present disclosure, the compound of interest is contacted with an isolated and purified ALK4:ActRIIB heteromultimer which is ordinarily capable of binding to a TGFβ superfamily ligand, as appropriate for the intention of the assay. To the mixture of the compound and ALK4:ActRIIB heteromultimer is then added to a composition containing the appropriate ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGβ31, TGβ32, TGβ33, activin A, activin B, activin C, activin E, activin AB, activin AC, nodal, glial cell-derived neurotrophic factor (GDNF), neurturin, artemin, persephin, MIS, and Lefty). Detection and quantification of heteromultimer-superfamily ligand complexes provides a means for determining the compound's efficacy at inhibiting (or potentiating) complex formation between the ALK4:ActRIIB heteromultimer and its binding protein. The efficacy of the compound can be assessed by generating dose-response curves from data obtained using various concentrations of the test compound. Moreover, a control assay can also be performed to provide a baseline for comparison. For example, in a control assay, isolated and purified ligand is added to a composition containing the ALK4:ActRIIB heteromultimer, and the formation of heteromultimer-ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Binding of an ALK4:ActRIIB heteromultimer to another protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ALK4:ActRIIB heteromultimer and/or a binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between an ALK4:ActRIIB heteromultimer and a binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two-hybrid assay," for identifying agents that disrupt or potentiate interaction between ALK4:ActRIIB heteromultimer and a binding partner. See, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present disclosure contemplates the use of reverse two-hybrid systems to identify compounds (e.g., small molecules or peptides) that dissociate interactions between an ALK4:ActRIIB heteromultimer and a binding protein [Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368].

In certain embodiments, the subject compounds are identified by their ability to interact with an ALK4:ActRIIB heteromultimer. The interaction between the compound and the ALK4:ActRIIB heteromultimer may be covalent or non-covalent. For example, such interaction can be identified at the protein level using in vitro biochemical methods, including photo-crosslinking, radiolabeled ligand binding, and affinity chromatography [Jakoby W B et al. (1974) Methods in Enzymology 46:1]. In certain cases, the compounds may be screened in a mechanism-based assay, such as an assay to detect compounds which bind to an ALK4:ActRIIB heteromultimer. This may include a solid-phase or fluid-phase binding event. Alternatively, the gene encoding an ALK4:ActRIIB heteromultimer can be transfected with a reporter system (e.g., β-galactosidase, luciferase, or green fluorescent protein) into a cell and screened against the library preferably by high-throughput screening or with individual members of the library. Other mechanism-based binding assays may be used; for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

8. Exemplary Therapeutic Uses

As demonstrated by the examples, an ALK4:ActRIIB antagonist (e.g., an ALK4:ActRIIB heterodimer) can be used to increase muscle mass and strength as well as increase bone mineral density in a spinal muscular atrophy (SMA) model. These data support the use of ALK4:ActRIIB antagonist therapy prolong ambulation and slow bone loss in patients with SMA. Therefore, in some embodiments, the present disclosure relates to ALK4:ActRIIB antagonists (e.g., ALK4:ActRIIB heterodimers) that may be used to treat patients with SMA, particularly preventing or reducing the severity of one or more complications of SMA. The terms "subject," an "individual," or a "patient" are interchangeable throughout the specification. Any of the ALK4:ActRIIB antagonists of the disclosure can potentially be employed individually or in combination for therapeutic uses disclosed herein. For example, an ALK4:ActRIIB antagonist may be used in combination with one or more additional active agent or supportive therapy for treating SMA. The methods described herein are particularly aimed at therapeutic and prophylactic treatments of mammals including, for example, rodents, primates, and humans.

As used herein, a therapeutic that "prevents" ("preventing") a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" ("treat") as used herein includes amelioration or elimination of the condition once it has been established. In either case, prevention or treatment may be discerned in the diagnosis provided by a physician or other health care provider and the intended result of administration of the therapeutic agent.

In general, treatment or prevention of a disease or condition as described in the present disclosure is achieved by administering an ALK4:ActRIIB antagonist of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

Spinal muscular atrophy is linked to a genetic mutation in the SMN1 gene [Brzustowicz, L. M. et al. (1990) Nature 344 (6266): 540-541.] Human chromosome 5 contains two nearly identical genes at location 5q13: a telomeric copy SMN1 and a centromeric copy SMN2. In healthy individuals, the SMN1 gene codes the survival of motor neuron protein (SMN) which, as its name suggests, plays a crucial role in survival of motor neurons. The SMN2 gene, on the other hand undergoes alternative splicing at the junction of intron 6 to exon 8, with only 10-20% of SMN2 transcripts coding a fully functional SMN protein and 80-90% of transcripts resulting in a truncated protein compound (SMNA7) which is rapidly degraded in the cell.

In individuals affected by SMA, the SMN1 gene is mutated in such a way that it is unable to correctly code the SMN protein—due to either a deletion occurring at exon 7 or to other point mutations (frequently resulting in the functional conversion of the SMN1 sequence into SMN2). Fortunately, almost all people have at least one functional copy of the SMN2 gene, which still codes small amounts of SMN protein—around 10-20% of the normal level—allowing some neurons to survive. However, reduced availability of the SMN protein results in gradual death of motor neuron cells, particularly in the anterior horn of spinal cord and the brain. Muscles that depend on these motor neurons for regulation have decreased innervation (also called denervation) and therefore have decreased central nervous system control. Decreased impulse transmission through the motor neurons leads to decreased contractile activity of the denervated muscle. Consequently, denervated muscles undergo progressive atrophy. Muscles of lower extremities are usually affected first, followed by muscles of upper extremities, spine and neck and, in more severe cases, pulmonary and mastication muscles. Proximal muscles are generally affected earlier and to a greater degree than distal.

SMA manifests over a wide range of severity, affecting infants through adults. The disease spectrum is divided into several types based on the age of onset of symptoms or with the highest attained milestone of motor development.

SMA1 (also known as Werdnig-Hoffmann disease) is a severe form of the disease that manifests in the first months of life, usually with a quick and unexpected onset ("floppy baby syndrome"). Rapid motor neuron death causes inefficiency of the major bodily organs, particularly especially of the respiratory system often leading to pneumonia-induced respiratory failure. Babies diagnosed with SMA type 1 do not generally live past two years of age. In some patients, death may occur as early as within weeks of birth (sometimes these most severe cases are termed SMA type 0). With proper respiratory support, those with milder SMA type I phenotypes, which account for around 10% of SMA1 cases, are known to live into adolescence and adulthood. In some embodiments, the disclosure relates to ALK4:ActRIIB antagonists for treating SMA1, particularly preventing or delaying onset and/or decreasing severity of one or more complications of SMA1.

SMA2 (also known as Dubowitx disease) is an intermediate form of the disease that affects children. Most SMA2 patients cannot stand or walk but are able to maintain a sitting position at least some period of time in their life. The onset of weakness is usually noticed some time between 6 and 18 months. The progress is known to vary greatly, some people gradually grow weaker over time while others through careful maintenance avoid any progression. Scoliosis may be present in SMA2 children, and correction with a brace may help improve respiration. Resipiatory complications are common amount SMA2 patients and are a significant cause of mortality. Life expectancy is somewhat reduced but most people with SMA2 live well into adulthood. In some embodiments, the disclosure relates to ALK4:ActRIIB antagonists for treating SMA2, particularly preventing or delaying onset and/or decreasing severity of one or more complications of SMA2.

SMA3 (also known as Kugelberg-Welander disease) is the juvenile form of the disease, usually manifests after 12 months of age. In general, people with SMA3 are able to walk without support at some period time in their life, although many later lose this ability. Respiratory involvement is less noticeable in SMA3, and life expectancy is normal or near normal. In some embodiments, the disclosure relates to treating SMA3, particularly preventing or delaying onset and/or decreasing severity of one or more complications of SMA3.

SMA4 is the adult-onset form of the disease (sometimes classified as a late-onset SMA type 3), usually manifesting after the third decade of life. In general, SMA4 patients experience gradual weakening of muscles, mainly in proximal muscles of the extremities. Frequently, SMA4 disease progression results in patients requiring wheelchair for mobility. Other complications are rare in SMA4 patients, and life expectancy is generally unaffected. In some embodiments, the disclosure relates to ALK4:ActRIIB antagonists for treating SMA4, particularly preventing or delaying onset and/or decreasing severity of one or more complications of SMA4.

The severity of SMA complications generally depends to how well the remaining SMN2 genes can make up for the loss of function of SMN1. This is partly related to the number of SMN2 gene copies present on the chromosome. While healthy individuals often carry two SMN2 gene copies, people with SMA may have between 1 and 4 (or even more) copies. Normally greater number of SMN2 copies in a patient is correlated with milder disease severity. Thus, most SMA type I babies have one or two SMN2 copies; people with SMA II and III usually have at least three SMN2 copies; and people with SMA IV normally have at least four copies. SMA-associated complications vary greatly depending on the type of SMA and stage of disease. SMA complications include, for example: areflexia, particularly in the extremities; overall muscle weakness; respiratory complications; respiratory failure; respiratory insufficiency; poor muscle tone; limpness or a tendency to flop; difficulty in achieving developmental milestones; difficulty sitting, standing, and/walking; loss of strength of respiratory muscles, often resulting in weak cough, weak cry, accumulation of secretions in lungs or throat, and/or respiratory distress; fasciculations of the tongue; bone loss (e.g., low bone mineral density) and/or weakness; and difficulty sucking or swallowing, often resulting in poor feeding. In some embodiments, the disclosure relates to ALK4:ActRIIB antagonists for treating one or more complication of SMA, particularly preventing or delaying onset and/or decreasing severity of one or more complications of SMA.

The Children's Hospital of Philadelphia Infant Test of Neuromuscular Disorders (CHOP INTEND) is a validated, 16-item, 64-point scale shown to be reliable in SMA Type I subjects. CHOP INTEND was derived in part from the Test of Infant Motor Performance (TIMP, see below) and was designed to measure motor function in weak infants with neuromuscular disease. It includes both active movements, spontaneous or goal-directed, and elicited reflexive movements, and assesses head, neck, trunk, and proximal and distal limb strength. CHOP INTEND does not include respiratory or feeding assessments, but it has been structured to move from easiest to hardest. The grading includes lower scores (gravity eliminated) and higher scores (antigravity movements). The typical symptomatic SMA Type I infant has a CHOP INTEND score of approximately 20-22 points on the 0-64 point scale. In the studies from both the PNCR68 and the NeuroNEXT SMA study, no infants with 2 copies of SMN2 had a baseline value over 40 points. In the recently conducted NeuroNEXT SMA infant biomarker study, a total of 23 SMA infants and 14 control infants were assessed. The average CHOP INTEND score for SMA infants who had 2 copies of SMN2 was 20.2 (SD=7.4, n=16, range=10-33) and the maximum score in this subgroup was 33, a finding consistent with the results of the PNCR type I SMA natural history study. In some embodiments, ALK4:ActRIIB antagonists of the disclosure may be used to treat SMA patients, wherein the treatment results in at least a 4-point in motor function in accordance with CHOP INTEND. For example, treatment may result in at least a 4, 5, 6, 7, 8, 9, 10, 11, 12, 13, 14, 15, 20, 25, 30, 35, 40, 45, 50, 55, or 60 point increase in motor function in accordance with CHOP INTEND.

The Hammersmith Infant Neurological Examination (HINE) is a neurological examination for infants between 2 and 24 months of age and consists of 37 items divided into 3 sections. Section I: Neurological Examination, includes assessments of cranial nerve function, posture, movements, tone, reflexes, and reactions. Section II assesses developmental milestones: head control, sitting, voluntary grasp, ability to kick, rolling, crawling, standing, and walking. Section III is a behavioural scale assessing the state of consciousness, emotional state, and social orientation. The HINE was utilized as an exploratory outcome measure in the Ionis CS3A open label infant SMA type I study of nusinersen, and because it was found to be informative, it evolved into a primary outcome measure in the randomized sham-controlled ENDEAR (CS3B) study. Each physical examination finding or milestone can be scored using a numerical scale, and therefore a global score can be created. In some embodiments, ALK4:ActRIIB antagonists of the disclosure may be used to treat SMA patients, wherein the treatment results in at least a 2-point in motor function in accordance with HIND. For example, treatment may result in at least a 4, 5, 6, 7, 8, 9, 10, 11, 12, 13, 14, 15, 20, 25, 30, 35, 40, 45, 50, 55, or 60 point increase in motor function in accordance with HIND.

The Test of Infant Motor Performance Screening Items (TIMPSI) is a 29-item, 99-point scale that has been shown to be valid and reproducible in infants with type I SMA. It tests rolling and crawling but does not test sitting. It includes many items administered in a prone position, which is not tolerated well by type I infants. It was utilized in the recent NeuroNEXT SMA infant biomarker study as a measure to screen the participating SMA and healthy infants' motor performance. Subjects who scored less than 41 on the TIMPSI were then evaluated using CHOP INTEND, and subjects who scored 41 or greater on the TIMPSI were evaluated using the Alberta Infant Motor Scale (AIMS, see below). The average TIMPSI score for the SMA cohort was 34.9 points, significantly lower than the average score for healthy controls (66.1, range=50-96). SMA infants with 2 copies of SMN2 had an average TIMPSI score of 27.2 (SD=8.0, n=16, range=15-49). In some embodiments, ALK4:ActRIIB antagonists of the disclosure may be used to treat SMA patients, wherein the treatment results in at least a 2-point in motor function in accordance with TIMPSI. For example, treatment may result in at least a 4, 5, 6, 7, 8, 9, 10, 11, 12, 13, 14, 15, 20, 25, 30, 35, 40, 45, 50, 55, 60, 65, 70, 75, or 80 point increase in motor function in accordance with TIMPSI.

The Bayley Scales of Infant Development (Bayley-III) includes assessment of motor function (gross and fine) as well as assessment of cognition and language (receptive and expressive) in infants and young children from 0-42 months. The Bayley-III language assessment is divided into expressive and receptive subtests; when these two subtests are combined, a composite score is determined. Similarly, the Bayley-III motor assessment includes scale scores for fine motor and gross motor development as well as a composite score. It has normative data, but in older/stronger children it takes a long time to administer. The main advantage of the Bayley scale is that it can also assess fine motor function, cognition and language; further, it can measure not only the acquisition of a milestone but also define when it was acquired. It has been used in the AveXis gene therapy type 1 trial. In some embodiments, ALK4:ActRIIB antagonists of the disclosure may be used to treat SMA patients, wherein the treatment results in at least a 2-point in motor function in accordance with Bayley-III. For example, treatment may result in at least a 4, 5, 6, 7, 8, 9, 10, 11, 12, 13, 14, 15, 20, 25, 30, 35, 40, 45, 50, 55, 60, 65, 70, 75, or 80 point increase in motor function in accordance with Bayley-III.

In some embodiments, the disclosure relates to methods of treating SMA, particularly preventing or delaying onset of and/or reducing the severity of one or more complications of SMA, comprising administering an ALK4:ActRIIB antagonist in combination with one or more additional active agents or supportive therapies for treating SMA.

As used herein, "in combination with", "combinations of", or "conjoint administration" refers to any form of administration such that additional therapies (e.g., second, third, fourth, etc.) are still effective in the body (e.g., multiple compounds are simultaneously effective in the patient, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more ALK4:ActRIIB antagonist of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired.

Since the underlying genetic cause of SMA was identified [Lefebvre et al. (1995) Cell. 80 (1): 155-165], several therapeutic approaches have been proposed and investigated that primarily focus on increasing the availability of SMN protein in motor neurons. The main research directions include: SMN1 gene replacement, SMN2 alternative splicing modulation, SMN2 gene activation, SMN stabilization, neuroprotection, and muscle restoration. In some embodiments, the disclosure relates to methods of treating SMA, particularly preventing or delaying onset of and/or reducing the severity of one or more complications of SMA, comprising administering an ALK4:ActRIIB antagonist in combination with one or more additional therapeutic approaches selected from: SMN1 gene replacement, SMN2 alternative splicing modulation, SMN2 gene activation, SMN stabilization, neuroprotection, and muscle restoration.

Nusinersen is the only approved drug to treat spinal muscular atrophy. It is an antisense drug that administered directly to the central nervous system using an intrathecal injection. Like other antisense drugs, there is a risk of abnormalities in blood clotting and a reduction in platelets as well as a risk of kidney damage. In clinical trials, people treated with nusinersen had an increased risk of upper and lower respiratory infections and congestion, ear infections, constipation, aspiration, teething, and scoliosis. In some embodiments, the disclosure relates to methods of treating SMA, particularly preventing or delaying onset of and/or reducing the severity of one or more complications of SMA, comprising administering an ALK4:ActRIIB antagonist in combination with nusinersen.

In general, gene therapy in SMA aims at restoring the SMN1 gene function through inserting specially crafted nucleotide sequence (a SMN1 transgene) into the cell nucleus using a viral vector; scAAV-9 and scAAV-10 are the primary viral vectors under investigation. For example, AVXS-101 uses self-complementary scAAV-9 as a vector to deliver the SMN1 transgene. Early results from an AVXS-101 clinical study show improvement in treated infants compared to the natural course of the disorder.

In general, SMN2 alternative splicing modulation approaches aim at modifying the alternative splicing of the SMN2 to force it to code for higher percentage of full-length SMN protein. Sometimes it is also called gene conversion, because it attempts to convert the SMN2 gene functionally into SMN1 gene. Splicing modulators have reached clinical stage development include, for example, branaplam (LMI070), RG7916, RG3039 (Quinazoline495), and RG7800. Basic research has also identified other compounds which modified SMN2 splicing in vitro including, for example, sodium orthovanadate and aclarubicin. Other Morpholino-type antisense oligonucleotides with the same cellular target as nusinersen remain a subject of intense research.

In general, SMN2 gene activation approaches aim at increasing expression (activity) of the SMN2 gene, thus increasing the amount of full-length SMN protein available. Oral salbutamol (albuterol), a popular asthma medicine, showed therapeutic potential in SMA both in vitro and in three small-scale clinical trials involving patients with SMA types 2 and 3, besides offering respiratory benefits. Other compounds that have shown promise in SMN2 gene activation include, for example, butyrates (sodium butyrate and sodium phenylbutyrate), valproic, hydroxycarbamide (hydroxyurea), histone deacetylase inhibitors, benzamide M344, hydroxamic acids (e.g., CBHA, SBHA, entinostat, panobinostat trichostatin A, and vorinostat), prolactin[as well as natural polyphenol compounds (e.g., resveratrol and curcumin), and p38 pathway activators (e.g., celecoxib).

In general, SMN stabilization aims at stabilizing the SMNA7 protein, the short-lived defective protein coded by the SMN2 gene, so that it is able to sustain neuronal cells. SMN stabilization agents that have been considered include, for example, aminoglycosides and indoprofen.

In general, neuroprotective drugs aim at enabling the survival of motor neurons even with low levels of SMN protein. For example, olesoxime is a proprietary neuroprotective compound which showed stabilizing effects in a phase II-III clinical trial involving people with SMA types 2 and 3. Other neuroprotective drugs that have been considered include, for example, thyrotropin-releasing hormone, riluzole, and β-lactam antibiotics (e.g., ceftriaxone).

In general, muscle restoration approaches aim to counter the effect of SMA by targeting the muscle tissue instead of neurons. For example, CK-2127107 (CK-107) is a skeletal troponin activator that is used to increasing muscle reactivity despite lowered neural signaling.

There are several supportive therapies for managing the various complications associated with SMA. For example, weak spine muscles may lead to development of kyphosis, scoliosis and other orthopaedic problems. Spine fusion is sometimes performed in people with SMA I/II once they reach the age of 8-10 to relieve the pressure of a deformed spine on the lungs. People with SMA might also benefit greatly from various forms of physiotherapy and occupational therapy.

Orthotic devices can be used to support the body and to aid walking. For example, orthotics such as AFO's (ankle foot orthosis) are used to stabilize the foot and to aid gait, TLSO's (thoracic lumbar sacral orthosis) are used to stabilize the torso. Assistive technologies may help in managing movement and daily activity and greatly increase the quality of life.

Respiratory system requires utmost attention in SMA as once weakened it never fully recovers. Weakened pulmonary muscles in people with SMA type I/II can make breathing more difficult and pose a risk of hypoxiation, especially in sleep when muscles are more relaxed. Impaired cough reflex poses a constant risk of respiratory infection and pneumonia. Non-invasive ventilation (BiPAP) is frequently used and tracheostomy may be sometimes performed in more severe cases. Booth of these methods of ventilation prolong survival in a comparable degree, although tracheostomy prevents speech development.

Difficulties in jaw opening, chewing and swallowing food might put people with SMA at risk of malnutrition. A feeding tube or gastrostomy can be necessary in SMA type I and people with more severe type II. Additionally, metabolic abnormalities resulting from SMA impair β-oxidation of fatty acids in muscles and can lead to organic acidemia and consequent muscle damage, especially when fasting. It is suggested that people with SMA, especially those with more severe forms of the disease, reduce intake of fat and avoid prolonged fasting (i.e., eat more frequently than healthy people).

An ALK4:ActRIIB antagonist of the disclosure may be conjointly administered with other bone-active pharmaceutical agents. ALK4:ActRIIB antagonists may be particularly advantageous if administered with other bone-active agents. A patient may benefit from conjointly receiving an ALK4:ActRIIB antagonist and taking calcium supplements, vitamin D, appropriate exercise and/or, in some cases, other medication. Examples of other medications include, bisphosphonates (alendronate, ibandronate and risedronate), calcitonin, estrogens, parathyroid hormone and raloxifene. The bisphosphonates (alendronate, ibandronate and risedronate), calcitonin, estrogens and raloxifene affect the bone remodeling cycle and are classified as anti-resorptive medications. Bone remodeling consists of two distinct stages: bone resorption and bone formation. Anti-resorptive medications slow or stop the bone-resorbing portion of the bone-remodeling cycle but do not slow the bone-forming portion of the cycle. As a result, new formation continues at a greater rate than bone resorption, and bone density may increase over time. Teriparatide, a form of parathyroid hormone, increases the rate of bone formation in the bone remodeling cycle. Alendronate is approved for both the prevention (5 mg per day or 35 mg once a week) and treatment (10 mg per day or 70 mg once a week) of postmenopausal osteoporosis. Alendronate reduces bone loss, increases bone density and reduces the risk of spine, wrist and hip fractures. Alendronate also is approved for treatment of glucocorticoid-induced osteoporosis in men and women as a result of long-term use of these medications (i.e., prednisone and cortisone) and for the treatment of osteoporosis in men. Alendronate plus vitamin D is approved for the treatment of osteoporosis in postmenopausal women (70 mg once a week plus vitamin D), and for treatment to improve bone mass in men with osteoporosis. Ibandronate is approved for the prevention and treatment of postmenopausal osteoporosis. Taken as a once-a-month pill (150 mg), ibandronate should be taken on the same day each month. Ibandronate reduces bone loss, increases bone density and reduces the risk of spine fractures. Risedronate is approved for the prevention and treatment of postmenopausal osteoporosis. Taken daily (5 mg dose) or weekly (35 mg dose or 35 mg dose with calcium), risedronate slows bone loss, increases bone density and reduces the risk of spine and non-spine fractures. Risedronate also is approved for use by men and women to prevent and/or treat glucocorticoid-induced osteoporosis that results from long-term use of these medications (i.e., prednisone or cortisone). Calcitonin is a naturally occurring hormone involved in calcium regulation and bone metabolism. In women who are more than 5 years beyond menopause, calcitonin slows bone loss, increases spinal bone density, and may relieve the pain associated with bone fractures. Calcitonin reduces the risk of spinal fractures. Calcitonin is available as an injection (50-100 IU daily) or nasal spray (200 IU daily).

A patient may also benefit from conjointly receiving an ALK4:ActRIIB antagonist and additional bone-active medications. Estrogen therapy (ET)/hormone therapy (HT) is approved for the prevention of osteoporosis. ET has been shown to reduce bone loss, increase bone density in both the spine and hip, and reduce the risk of hip and spinal fractures in postmenopausal women. ET is administered most commonly in the form of a pill or skin patch that delivers a low dose of approximately 0.3 mg daily or a standard dose of approximately 0.625 mg daily and is effective even when started after age 70. When estrogen is taken alone, it can increase a woman's risk of developing cancer of the uterine lining (endometrial cancer). To eliminate this risk, healthcare providers prescribe the hormone progestin in combination with estrogen (hormone replacement therapy or HT) for those women who have an intact uterus. ET/HT relieves menopause symptoms and has been shown to have a beneficial effect on bone health. Side effects may include vaginal bleeding, breast tenderness, mood disturbances and gallbladder disease. Raloxifene, 60 mg a day, is approved for the prevention and treatment of postmenopausal osteoporosis. It is from a class of drugs called Selective Estrogen Receptor Modulators (SERMs) that have been developed to provide the beneficial effects of estrogens without their potential disadvantages. Raloxifene increases bone mass and reduces the risk of spine fractures. Data are not yet available to demonstrate that raloxifene can reduce the risk of hip and other non-spine fractures. Teriparatide, a form of parathyroid hormone, is approved for the treatment of osteoporosis in postmenopausal women and men who are at high risk for a fracture. This medication stimulates new bone formation and significantly increases bone mineral density. In postmenopausal women, fracture reduction was noted in the spine, hip, foot, ribs and wrist. In men, fracture reduction was noted in the spine, but there were insufficient data to evaluate fracture reduction at other sites. Teriparatide is self-administered as a daily injection for up to 24 months.

9. Pharmaceutical Compositions

In certain aspects, ALK4:ActRIIB antagonists of the present disclosure can be administered alone or as a component of a pharmaceutical formulation (also referred to as a therapeutic composition or pharmaceutical composition). A pharmaceutical formation refers to a preparation which is in such form as to permit the biological activity of an active ingredient (e.g., an agent of the present disclosure) contained therein to be effective and which contains no additional components which are unacceptably toxic to a subject to which the formulation would be administered. The subject compounds may be formulated for administration in any convenient way for use in human or veterinary medicine. For example, one or more agents of the present disclosure may be formulated with a pharmaceutically acceptable carrier. A pharmaceutically acceptable carrier refers to an ingredient in a pharmaceutical formulation, other than an active ingredient, which is generally nontoxic to a subject. A pharmaceutically acceptable carrier includes, but is not limited to, a buffer, excipient, stabilizer, and/or preservative. In general, pharmaceutical formulations for use in the present disclosure are in a pyrogen-free, physiologically-acceptable form when administered to a subject. Therapeutically useful agents other than those described herein, which may optionally be included in the formulation as described above, may be administered in combination with the subject agents in the methods of the present disclosure.

In certain embodiments, compositions will be administered parenterally [e.g., by intravenous (I.V.) injection, intraarterial injection, intraosseous injection, intramuscular injection, intrathecal injection, subcutaneous injection, or intradermal injection]. Pharmaceutical compositions suitable for parenteral administration may comprise one or more agents of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use. Injectable solutions or dispersions may contain antioxidants, buffers, bacteriostats, suspending agents, thickening agents, or solutes which render the formulation isotonic with the blood of the intended recipient. Examples of suitable aqueous and nonaqueous carriers which may be employed in the pharmaceutical formulations of the present disclosure include water, ethanol, polyols (e.g., glycerol, propylene glycol, polyethylene glycol, etc.), vegetable oils (e.g., olive oil), injectable organic esters (e.g., ethyl oleate), and suitable mixtures thereof. Proper fluidity can be maintained, for example, by the use of coating materials (e.g., lecithin), by the maintenance of the required particle size in the case of dispersions, and by the use of surfactants.

In some embodiments, a therapeutic method of the present disclosure includes administering the pharmaceutical composition systemically, or locally, from an implant or device. Further, the pharmaceutical composition may be encapsulated or injected in a form for delivery to a target tissue site (e.g., bone marrow or muscle). In certain embodiments, compositions of the present disclosure may include a matrix capable of delivering one or more of the agents of the present disclosure to a target tissue site (e.g., bone marrow or muscle), providing a structure for the developing tissue and optimally capable of being resorbed into the body. For example, the matrix may provide slow release of one or more agents of the present disclosure. Such matrices may be formed of materials presently in use for other implanted medical applications.

The choice of matrix material may be based on one or more of: biocompatibility, biodegradability, mechanical properties, cosmetic appearance, and interface properties. The particular application of the subject compositions will define the appropriate formulation. Potential matrices for the compositions may be biodegradable and chemically defined calcium sulfate, tricalciumphosphate, hydroxyapatite, polylactic acid, and polyanhydrides. Other potential materials are biodegradable and biologically well-defined including, for example, bone or dermal collagen. Further matrices are comprised of pure proteins or extracellular matrix components. Other potential matrices are non-biodegradable and chemically defined including, for example, sintered hydroxyapatite, bioglass, aluminates, or other ceramics. Matrices may be comprised of combinations of any of the above mentioned types of material including, for example, polylactic acid and hydroxyapatite or collagen and tricalciumphosphate. The bioceramics may be altered in composition (e.g., calcium-aluminate-phosphate) and processing to alter one or more of pore size, particle size, particle shape, and biodegradability.

In certain embodiments, pharmaceutical compositions of present disclosure can be administered topically. "Topical application" or "topically" means contact of the pharmaceutical composition with body surfaces including, for example, the skin, wound sites, and mucous membranes. The topical pharmaceutical compositions can have various application forms and typically comprises a drug-containing layer, which is adapted to be placed near to or in direct contact with the tissue upon topically administering the composition. Pharmaceutical compositions suitable for topical administration may comprise one or more one or more ALK4:ActRIIB antagonists of the disclosure in combination formulated as a liquid, a gel, a cream, a lotion, an ointment, a foam, a paste, a putty, a semi-solid, or a solid. Compositions in the liquid, gel, cream, lotion, ointment, foam, paste, or putty form can be applied by spreading, spraying, smearing, dabbing or rolling the composition on the target tissue. The compositions also may be impregnated into sterile dressings, transdermal patches, plasters, and bandages. Compositions of the putty, semi-solid or solid forms may be deformable. They may be elastic or non-elastic (e.g., flexible or rigid). In certain aspects, the composition forms part of a composite and can include fibers, particulates, or multiple layers with the same or different compositions.

Topical compositions in the liquid form may include pharmaceutically acceptable solutions, emulsions, microemulsions, and suspensions. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof].

Topical gel, cream, lotion, ointment, semi-solid or solid compositions may include one or more thickening agents, such as a polysaccharide, synthetic polymer or protein-based polymer. In one embodiment of the invention, the gelling agent herein is one that is suitably nontoxic and gives the desired viscosity. The thickening agents may include polymers, copolymers, and monomers of: vinylpyrrolidones, methacrylamides, acrylamides N-vinylimidazoles, carboxy vinyls, vinyl esters, vinyl ethers, silicones, polyethyleneoxides, polyethyleneglycols, vinylalcohols, sodium acrylates, acrylates, maleic acids, NN-dimethylacrylamides, diacetone acrylamides, acrylamides, acryloyl morpholine, pluronic, collagens, polyacrylamides, polyacrylates, polyvinyl alcohols, polyvinylenes, polyvinyl silicates, polyacrylates substituted with a sugar (e.g., sucrose, glucose, glucosamines, galactose, trehalose, mannose, or lactose), acylamidopropane sulfonic acids, tetramethoxyorthosilicates, methyltrimethoxyorthosilicates, tetraalkoxyorthosilicates, trialkoxyorthosilicates, glycols, propylene glycol, glycerine, polysaccharides, alginates, dextrans, cyclodextrin, celluloses, modified celluloses, oxidized celluloses, chitosans, chitins, guars, carrageenans, hyaluronic acids, inulin, starches, modified starches, agarose, methylcelluloses, plant gums, hylaronans, hydrogels, gelatins, glycosaminoglycans, carboxymethyl celluloses, hydroxyethyl celluloses, hydroxy propyl methyl celluloses, pectins, low-methoxy pectins, cross-linked dextrans, starch-acrylonitrile graft copolymers, starch sodium polyacrylate, hydroxyethyl methacrylates, hydroxyl ethyl acrylates, polyvinylene, polyethylvinylethers, polymethyl methacrylates, polystyrenes, polyurethanes, polyalkanoates, polylactic acids, polylactates, poly (3-hydroxybutyrate), sulfonated hydrogels, AMPS (2-acrylamido-2-methyl-1-propanesulfonic acid), SEM (sulfoethylmethacrylate), SPM (sulfopropyl methacrylate), SPA (sulfopropyl acrylate), N,N-dimethyl-N-methacryloxyethyl-N-(3-sulfopropyl)ammonium betaine, methacryllic acid amidopropyl-dimethyl ammonium sulfobetaine, SPI (itaconic acid-bis(1-propyl sulfonizacid-3) ester di-potassium salt), itaconic acids, AMBC (3-acrylamido-3-methylbutanoic acid), beta-carboxyethyl acrylate (acrylic acid dimers), and maleic anhydride-methylvinyl ether polymers, derivatives thereof, salts thereof, acids thereof, and combinations thereof. In certain embodiments, pharmaceutical compositions of present disclosure can be administered orally, for example, in the form of capsules, cachets, pills, tablets, lozenges (using a flavored basis such as sucrose and acacia or tragacanth), powders, granules, a solution or a suspension in an aqueous or non-aqueous liquid, an oil-in-water or water-in-oil liquid emulsion, or an elixir or syrup, or pastille (using an inert base, such as gelatin and glycerin, or sucrose and acacia), and/or a mouth wash, each containing a predetermined amount of a compound of the present disclosure and optionally one or more other active ingredients. A compound of the present disclosure and optionally one or more other active ingredients may also be administered as a bolus, electuary, or paste.

In solid dosage forms for oral administration (e.g., capsules, tablets, pills, dragees, powders, and granules), one or more compounds of the present disclosure may be mixed with one or more pharmaceutically acceptable carriers including, for example, sodium citrate, dicalcium phosphate, a filler or extender (e.g., a starch, lactose, sucrose, glucose, mannitol, and silicic acid), a binder (e.g. carboxymethylcellulose, an alginate, gelatin, polyvinyl pyrrolidone, sucrose, and acacia), a humectant (e.g., glycerol), a disintegrating agent (e.g., agar-agar, calcium carbonate, potato or tapioca starch, alginic acid, a silicate, and sodium carbonate), a solution retarding agent (e.g. paraffin), an absorption accelerator (e.g. a quaternary ammonium compound), a wetting agent (e.g., cetyl alcohol and glycerol monostearate), an absorbent (e.g., kaolin and bentonite clay), a lubricant (e.g., a talc, calcium stearate, magnesium stearate, solid polyethylene glycols, sodium lauryl sulfate), a coloring agent, and mixtures thereof. In the case of capsules, tablets, and pills, the pharmaceutical formulation (composition) may also comprise a buffering agent. Solid compositions of a similar type may also be employed as fillers in soft and hard-filled gelatin capsules using one or more excipients including, e.g., lactose or a milk sugar as well as a high molecular-weight polyethylene glycol.

Liquid dosage forms for oral administration of the pharmaceutical composition may include pharmaceutically acceptable emulsions, microemulsions, solutions, suspensions, syrups, and elixirs. In addition to the active ingredient (s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof]. Besides inert diluents, the oral formulation can also include an adjuvant including, for example, a wetting agent, an emulsifying and suspending agent, a sweetening agent, a flavoring agent, a coloring agent, a perfuming agent, a preservative agent, and combinations thereof.

Suspensions, in addition to the active compounds, may contain suspending agents including, for example, an ethoxylated isostearyl alcohol, polyoxyethylene sorbitol, a sorbitan ester, microcrystalline cellulose, aluminum metahydroxide, bentonite, agar-agar, tragacanth, and combinations thereof.

Prevention of the action and/or growth of microorganisms may be ensured by the inclusion of various antibacterial and antifungal agents including, for example, paraben, chlorobutanol, and phenol sorbic acid.

In certain embodiments, it may be desirable to include an isotonic agent including, for example, a sugar or sodium chloride into the compositions. In addition, prolonged absorption of an injectable pharmaceutical form may be brought about by the inclusion of an agent that delay absorption including, for example, aluminum monostearate and gelatin.

It is understood that the dosage regimen will be determined by the attending physician considering various factors which modify the action of the one or more of the agents of the present disclosure. In the case of a ALK4:ActRIIB antagonist that promotes red blood cell formation, various factors may include, but are not limited to, the patient's red blood cell count, hemoglobin level, the desired target red blood cell count, the patient's age, the patient's sex, the patient's diet, the severity of any disease that may be contributing to a depressed red blood cell level, the time of administration, and other clinical factors. The addition of other known active agents to the final composition may also affect the dosage. Progress can be monitored by periodic assessment of one or more of red blood cell levels, hemoglobin levels, reticulocyte levels, and other indicators of the hematopoietic process.

In certain embodiments, the present disclosure also provides gene therapy for the in vivo production of one or more of the agents of the present disclosure. Such therapy would achieve its therapeutic effect by introduction of the agent sequences into cells or tissues having one or more of the disorders as listed above. Delivery of the agent sequences can be achieved, for example, by using a recombinant expression vector such as a chimeric virus or a colloidal dispersion system. Preferred therapeutic delivery of one or more of agent sequences of the disclosure is the use of targeted liposomes.

Various viral vectors which can be utilized for gene therapy as taught herein include adenovirus, herpes virus, vaccinia, or an RNA virus (e.g., a retrovirus). The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing one or more of the agents of the present disclosure.

Alternatively, tissue culture cells can be directly transfected with plasmids encoding the retroviral structural genes (gag, pol, and env), by conventional calcium phosphate transfection. These cells are then transfected with the vector plasmid containing the genes of interest. The resulting cells release the retroviral vector into the culture medium.

Another targeted delivery system for one or more of the agents of the present disclosure is a colloidal dispersion system. Colloidal dispersion systems include, for example, macromolecule complexes, nanocapsules, microspheres, beads, and lipid-based systems including oil-in-water emulsions, micelles, mixed micelles, and liposomes. In certain embodiments, the preferred colloidal system of this disclosure is a liposome. Liposomes are artificial membrane vesicles which are useful as delivery vehicles in vitro and in vivo. RNA, DNA, and intact virions can be encapsulated within the aqueous interior and be delivered to cells in a biologically active form [Fraley, et al. (1981) Trends Biochem. Sci., 6:77]. Methods for efficient gene transfer using a liposome vehicle are known in the art [Mannino, et al. (1988) Biotechniques, 6:682, 1988].

The composition of the liposome is usually a combination of phospholipids, which may include a steroid (e.g. cholesterol). The physical characteristics of liposomes depend on pH, ionic strength, and the presence of divalent cations. Other phospholipids or other lipids may also be used including, for example a phosphatidyl compound (e.g., phosphatidylglycerol, phosphatidylcholine, phosphatidylserine, phosphatidylethanolamine, a sphingolipid, a cerebroside, and a ganglioside), egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of an ALK4:ActRIIB Heterodimer

Soluble ALK4-Fc:ActRIIB-Fc heteromeric complexes comprising the extracellular domains of human ActRIIB and human ALK4, which are each separately fused to an Fc domain with a linker positioned between the extracellular domain and the Fc domain, were constructed. The individual constructs are referred to as ActRIIB-Fc fusion polypeptide and ALK4-Fc fusion polypeptide, respectively, and the sequences for each are provided below.

A methodology for promoting formation of ALK4-Fc:ActRIIB-Fc heteromeric complexes, as opposed to ActRIIB-Fc or ALK4-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIB-Fc and ALK4-Fc polypeptide sequences of SEQ ID NOs: 39-41 and 42-44, respectively, one Fc domain is altered to introduce cationic amino acids at the interaction face, while the other Fc domain is altered to introduce anionic amino acids at the interaction face. ActRIIB-Fc fusion polypeptide and ALK4-Fc fusion polypeptide each employ the tissue plasminogen activator (TPA) leader:

```
                                        (SEQ ID NO: 38)
        MDAMKRGLCCVLLLCGAVFVSP.
```

The ActRIIB-Fc polypeptide sequence (SEQ ID NO: 39) is shown below:

```
                                                    (SEQ ID NO: 39)
  1  MDAMKRGLCC VLLLCGAVFV SPGASGRGEA ETRECIYYNA NWELERTNQS

 51  GLERCEGEQD KRLHCYASWR NSSGTIELVK KGCWLDDFNC YDRQECVATE

101  ENPQVYFCCC EGNFCNERFT HLPEAGGPEV TYEPPPTAPT GGGTHTCPPC

151  PAPELLGGPS VFLFPPKPKD TLMISRTPEV TCVVVDVSHE DPEVKFNWYV

201  DGVEVHNAKT KPREEQYNST YRVVSVLTVL HQDWLNGKEY KCKVSNKALP

251  APIEKTISKA KGQPREPQVY TLPPSRKEMT KNQVSLTCLV KGFYPSDIAV

301  EWESNGQPEN NYKTTPPVLK SDGSFFLYSK LTVDKSRWQQ GNVFSCSVMH

351  EALHNHYTQK SLSLSPGK
```

The leader (signal) sequence and linker are underlined. To promote formation of ALK4-Fc:ActRIIB-Fc heterodimer rather than either of the possible homodimeric complexes, two amino acid substitutions (replacing acidic amino acids with lysine) can be introduced into the Fc domain of the ActRIIB fusion protein as indicated by doubleunderline above. The amino acid sequence of SEQ ID NO: 39 may optionally be provided with lysine (K) removed from the C-terminus.

This ActRIIB-Fc fusion protein is encoded by the following nucleic acid sequence (SEQ ID NO: 40):

```
                                                      (SEQ ID NO: 40)
   1    ATGGATGCAA TGAAGAGAGG GCTCTGCTGT GTGCTGCTGC TGTGTGGAGC

  51    AGTCTTCGTT TCGCCCGGCG CCTCTGGGCG TGGGGAGGCT GAGACACGGG

 101    AGTGCATCTA CTACAACGCC AACTGGGAGC TGGAGCGCAC CAACCAGAGC

 151    GGCCTGGAGC GCTGCGAAGG CGAGCAGGAC AAGCGGCTGC ACTGCTACGC

 201    CTCCTGGCGC AACAGCTCTG GCACCATCGA GCTCGTGAAG AAGGGCTGCT

 251    GGCTAGATGA CTTCAACTGC TACGATAGGC AGGAGTGTGT GGCCACTGAG

 301    GAGAACCCCC AGGTGTACTT CTGCTGCTGT GAAGGCAACT TCTGCAACGA

 351    GCGCTTCACT CATTTGCCAG AGGCTGGGGG CCCGGAAGTC ACGTACGAGC

 401    CACCCCCGAC AGCCCCCACC GGTGGTGGAA CTCACACATG CCCACCGTGC

 451    CCAGCACCTG AACTCCTGGG GGGACCGTCA GTCTTCCTCT TCCCCCCAAA

 501    ACCCAAGGAC ACCCTCATGA TCTCCCGGAC CCCTGAGGTC ACATGCGTGG

 551    TGGTGGACGT GAGCCACGAA GACCCTGAGG TCAAGTTCAA CTGGTACGTG

 601    GACGGCGTGG AGGTGCATAA TGCCAAGACA AAGCCGCGGG AGGAGCAGTA

 651    CAACAGCACG TACCGTGTGG TCAGCGTCCT CACCGTCCTG CACCAGGACT

 701    GGCTGAATGG CAAGGAGTAC AAGTGCAAGG TCTCCAACAA AGCCCTCCCA

 751    GCCCCCATCG AGAAAACCAT CTCCAAAGCC AAAGGGCAGC CCCGAGAACC

 801    ACAGGTGTAC ACCCTGCCCC CATCCCGGAA GGAGATGACC AAGAACCAGG

 851    TCAGCCTGAC CTGCCTGGTC AAAGGCTTCT ATCCCAGCGA CATCGCCGTG

 901    GAGTGGGAGA GCAATGGGCA GCCGGAGAAC AACTACAAGA CCACGCCTCC

 951    CGTGCTGAAG TCCGACGGCT CCTTCTTCCT CTATAGCAAG CTCACCGTGG

1001    ACAAGAGCAG GTGGCAGCAG GGGAACGTCT TCTCATGCTC CGTGATGCAT

1051    GAGGCTCTGC ACAACCACTA CACGCAGAAG AGCCTCTCCC TGTCTCCGGG

1101    TAAA
```

The mature ActRIIB-Fc fusion polypeptide (SEQ ID NO: 41) is as follows, and may optionally be provided with lysine (K) removed from the C-terminus.

```
                                                      (SEQ ID NO: 41)
   1    GRGEAETREC IYYNANWELE RTNQSGLERC EGEQDKRLHC YASWRNSSGT

  51    IELVKKGCWL DDFNCYDRQE CVATEENPQV YFCCCEGNFC NERFTHLPEA

 101    GGPEVTYEPP PTAPTGGGTH TCPPCPAPEL LGGPSVFLFP PKPKDTLMIS

 151    RTPEVTCVVV DVSHEDPEVK FNWYVDGVEV HNAKTKPREE QYNSTYRVVS

 201    VLTVLHQDWL NGKEYKCKVS NKALPAPIEK TISKAKGQPR EPQVYTLPPS

 251    RKEMTKNQVS LTCLVKGFYP SDIAVEWESN GQPENNYKTT PPVLKSDGSF

 301    FLYSKLTVDK SRWQQGNVFS CSVMHEALHN HYTQKSLSLS PGK
```

The complementary form of ALK4-Fc fusion polypeptide (SEQ ID NO: 42) is as follows:

(SEQ ID NO: 42)

```
1    MDAMKRGLCC VLLLCGAVFV SPGASGPRGV QALLCACTSC LQANYTCETD
51   GACMVSIFNL DGMEHHVRTC IPKVELVPAG KPFYCLSSED LRNTHCCYTD
101  YCNRIDLRVP SGHLKEPEHP SMWGPVETGG GTHTCPPCPA PELLGGPSVF
151  LFPPKPKDTL MISRTPEVTC VVVDVSHEDP EVKFNWYVDG VEVHNAKTKP
201  REEQYNSTYR VVSVLTVLHQ DWLNGKEYKC KVSNKALPAP IEKTISKAKG
251  QPREPQVYTL PPSREEMTKN QVSLTCLVKG FYPSDIAVEW ESNGQPENNY
301  DTTPPVLDSD GSFFLYSDLT VDKSRWQQGN VFSCSVMHEA LHNHYTQKSL
351  SLSPG
```

The leader sequence and linker are underlined. To guide heterodimer formation with the ActRIIB-Fc fusion polypeptide of SEQ ID NOs: 39 and 41 above, two amino acid substitutions (replacing lysines with aspartic acids) can be introduced into the Fc domain of the ALK4-Fc fusion polypeptide as indicated by doubleunderline above. The amino acid sequence of SEQ ID NO: 42 may optionally be provided with lysine (K) added at the C-terminus.

This ALK4-Fc fusion protein is encoded by the following nucleic acid (SEQ ID NO: 43):

(SEQ ID NO: 43)

```
1    ATGGATGCAA TGAAGAGAGG GCTCTGCTGT GTGCTGCTGC TGTGTGGAGC
51   AGTCTTCGTT TCGCCCGGCG CCTCCGGGCC CCGGGGGGTC CAGGCTCTGC
101  TGTGTGCGTG CACCAGCTGC CTCCAGGCCA ACTACACGTG TGAGACAGAT
151  GGGGCCTGCA TGGTTTCCAT TTTCAATCTG GATGGGATGG AGCACCATGT
201  GCGCACCTGC ATCCCCAAAG TGGAGCTGGT CCCTGCCGGG AAGCCCTTCT
251  ACTGCCTGAG CTCGGAGGAC CTGCGCAACA CCCACTGCTG CTACACTGAC
301  TACTGCAACA GGATCGACTT GAGGGTGCCC AGTGGTCACC TCAAGGAGCC
351  TGAGCACCCG TCCATGTGGG GCCCGGTGGA GACCGGTGGT GGAACTCACA
401  CATGCCCACC GTGCCCAGCA CCTGAACTCC TGGGGGGACC GTCAGTCTTC
451  CTCTTCCCCC CAAAACCCAA GGACACCCTC ATGATCTCCC GGACCCCTGA
501  GGTCACATGC GTGGTGGTGG ACGTGAGCCA CGAAGACCCT GAGGTCAAGT
551  TCAACTGGTA CGTGGACGGC GTGGAGGTGC ATAATGCCAA GACAAAGCCG
601  CGGGAGGAGC AGTACAACAG CACGTACCGT GTGGTCAGCG TCCTCACCGT
651  CCTGCACCAG GACTGGCTGA ATGGCAAGGA GTACAAGTGC AAGGTCTCCA
701  ACAAAGCCCT CCCAGCCCCC ATCGAGAAAA CCATCTCCAA AGCCAAAGGG
751  CAGCCCCGAG AACCACAGGT GTACACCCTG CCCCCATCCC GGGAGGAGAT
801  GACCAAGAAC CAGGTCAGCC TGACCTGCCT GGTCAAAGGC TTCTATCCCA
851  GCGACATCGC CGTGGAGTGG GAGAGCAATG GGCAGCCGGA GAACAACTAC
901  GACACCACGC CTCCCGTGCT GGACTCCGAC GGCTCCTTCT TCCTCTATAG
951  CGACCTCACC GTGGACAAGA GCAGGTGGCA GCAGGGGAAC GTCTTCTCAT
1001 GCTCCGTGAT GCATGAGGCT CTGCACAACC ACTACACGCA GAAGAGCCTC
1051 TCCCTGTCTC CGGGT
```

The mature ALK4-Fc fusion protein sequence (SEQ ID NO: 44) is as follows and may optionally be provided with lysine (K) added at the C-terminus.

```
                                                    (SEQ ID NO: 44)
  1    SGPRGVQALL CACTSCLQAN YTCETDGACM VSIFNLDGME HHVRTCIPKV

 51    ELVPAGKPFY CLSSEDLRNT HCCYTDYCNR IDLRVPSGHL KEPEHPSMWG

101    PVETGGGTHT CPPCPAPELL GGPSVFLFPP KPKDTLMISR TPEVTCVVVD

151    VSHEDPEVKF NWYVDGVEVH NAKTKPREEQ YNSTYRVVSV LTVLHQDWLN

201    GKEYKCKVSN KALPAPIEKT ISKAKGQPRE PQVYTLPPSR EEMTKNQVSL

251    TCLVKGFYPS DIAVEWESNG QPENNYDTTP PVLDSDGSFF LYSDLTVDKS

301    RWQQGNVFSC SVMHEALHNH YTQKSLSLSP G
```

The ActRIIB-Fc and ALK4-Fc proteins of SEQ ID NO: 41 and SEQ ID NO: 44, respectively, may be co-expressed and purified from a CHO cell line, to give rise to a heteromeric complex comprising ALK4-Fc:ActRIIB-Fc.

In another approach to promote the formation of heteromultimer complexes using asymmetric Fc fusion proteins the Fc domains are altered to introduce complementary hydrophobic interactions and an additional intermolecular disulfide bond as illustrated in the ActRIIB-Fc and ALK4-Fc polypeptide sequences of SEQ ID NOs: 45-46 and 47-48, respectively. The ActRIIB-Fc fusion polypeptide and ALK4-Fc fusion polypeptide each employ the tissue plasminogen activator (TPA) leader:

```
                              (SEQ ID NO: 38)
       MDAMKRGLCCVLLLCGAVFVSP.
```

The ActRIIB-Fc polypeptide sequence (SEQ ID NO: 45) is shown below:

```
                                                    (SEQ ID NO: 45)
  1    MDAMKRGLCC VLLLCGAVFV SPGASGRGEA ETRECIYYNA NWELERTNQS

 51    GLERCEGEQD KRLHCYASWR NSSGTIELVK KGCWLDDFNC YDRQECVATE

101    ENPQVYFCCC EGNFCNERFT HLPEAGGPEV TYEPPPTAPT GGGTHTCPPC

151    PAPELLGGPS VFLFPPKPKD TLMISRTPEV TCVVVDVSHE DPEVKFNWYV

201    DGVEVHNAKT KPREEQYNST YRVVSVLTVL HQDWLNGKEY KCKVSNKALP

251    APIEKTISKA KGQPREPQVY TLPPCREEMT KNQVSLWCLV KGFYPSDIAV

301    EWESNGQPEN NYKTTPPVLD SDGSFFLYSK LTVDKSRWQQ GNVFSCSVMH

351    EALHNHYTQK SLSLSPGK
```

The leader (signal) sequence and linker are underlined. To promote formation of the ALK4-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by doubleunderline above. The amino acid sequence of SEQ ID NO: 45 may optionally be provided with lysine (K) removed from the C-terminus.

The mature ActRIIB-Fc fusion polypeptide is as follows:

```
                                                  (SEQ ID NO: 46)
  1     GRGEAETREC IYYNANWELE RTNQSGLERC EGEQDKRLHC YASWRNSSGT

 51     IELVKKGCWL DDFNCYDRQE CVATEENPQV YFCCCEGNFC NERFTHLPEA

101     GGPEVTYEPP PTAPTGGGTH TCPPCPAPEL LGGPSVFLFP PKPKDTLMIS

151     RTPEVTCVVV DVSHEDPEVK FNWYVDGVEV HNAKTKPREE QYNSTYRVVS

201     VLTVLHQDWL NGKEYKCKVS NKALPAPIEK TISKAKGQPR EPQVYTLPPC

251     REEMTKNQVS LWCLVKGFYP SDIAVEWESN GQPENNYKTT PPVLDSDGSF

301     FLYSKLTVDK SRWQQGNVFS CSVMHEALHN HYTQKSLSLS PGK
```

The complementary form of ALK4-Fc fusion polypeptide (SEQ ID NO: 47) is as follows and may optionally be provided with lysine (K) removed from the C-terminus.

```
                                                  (SEQ ID NO: 47)
  1     MDAMKRGLCC VLLLCGAVFV SPGASGPRGV QALLCACTSC LQANYTCETD

 51     GACMVSIFNL DGMEHHVRTC IPKVELVPAG KPFYCLSSED LRNTHCCYTD

101     YCNRIDLRVP SGHLKEPEHP SMWGPVETGG GTHTCPPCPA PELLGGPSVF

151     LFPPKPKDTL MISRTPEVTC VVVDVSHEDP EVKFNWYVDG VEVHNAKTKP

201     REEQYNSTYR VVSVLTVLHQ DWLNGKEYKC KVSNKALPAP IEKTISKAKG

251     QPREPQVCTL PPSREEMTKN QVSLSCAVKG FYPSDIAVEW ESNGQPENNY

301     KTTPPVLDSD GSFFLVSKLT VDKSRWQQGN VFSCSVMHEA LHNHYTQKSL

351     SLSPGK
```

The leader sequence and the linker are underlined. To guide heterodimer formation with the ActRIIB-Fc fusion polypeptide of SEQ ID NOs: 45 and 46 above, four amino acid substitutions can be introduced into the Fc domain of the ALK4 fusion polypeptide as indicated by doubleunderline above. The amino acid sequence of SEQ ID NO: 47 may optionally be provided with lysine (K) removed from the C-terminus.

The mature ALK4-Fc fusion protein sequence is as follows and may optionally be provided with lysine (K) removed from the C-terminus.

```
                                                  (SEQ ID NO: 48)
  1     SGPRGVQALL CACTSCLQAN YTCETDGACM VSIFNLDGME HHVRTCIPKV

 51     ELVPAGKPFY CLSSEDLRNT HCCYTDYCNR IDLRVPSGHL KEPEHPSMWG

101     PVETGGGTHT CPPCPAPELL GGPSVFLFPP KPKDTLMISR TPEVTCVVVD

151     VSHEDPEVKF NWYVDGVEVH NAKTKPREEQ YNSTYRVVSV LTVLHQDWLN

201     GKEYKCKVSN KALPAPIEKT ISKAKGQPRE PQVCTLPPSR EEMTKNQVSL

251     SCAVKGFYPS DIAVEWESNG QPENNYKTTP PVLDSDGSFF LVSKLTVDKS

301     RWQQGNVFSC SVMHEALHNH YTQKSLSLSP GK
```

ActRIIB-Fc and ALK4-Fc proteins of SEQ ID NO: 46 and SEQ ID NO: 48, respectively, may be co-expressed and purified from a CHO cell line, to give rise to a heteromeric complex comprising ALK4-Fc:ActRIIB-Fc.

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography, cation exchange chromatography, and epitope-based affinity chromatography (e.g., with an antibody or functionally equivalent ligand directed against an epitope on ALK4 or ActRIIB) The purification could be completed with viral filtration and buffer exchange.

In another approach to promote the formation of heteromultimer complexes using asymmetric Fc fusion proteins, the Fc domains are altered to introduce complementary hydrophobic interactions, an additional intermolecular disulfide bond, and electrostatic differences between the two Fc domains for facilitating purification based on net molecular charge, as illustrated in the ActRIIB-Fc and ALK4-Fc polypeptide sequences of SEQ ID NOs: 70-73 and 74-77, respectively. The ActRIIB-Fc fusion polypeptide and ALK4-Fc fusion polypeptide each employ the tissue plasminogen activator (TPA) leader: MDAMKRGLCCVLLLCGAVFVSP (SEQ ID NO: 38).

The ActRIIB-Fc polypeptide sequence (SEQ ID NO: 70) is shown below:

```
                                            (SEQ ID NO: 70)
  1  MDAMKRGLCC VLLLCGAVFV SPGASGRGEA ETRECIYYNA NWELERTNQS
 51  GLERCEGEQD KRLHCYASWR NSSGTIELVK KGCWLDDFNC YDRQECVATE
101  ENPQVYFCCC EGNFCNERFT HLPEAGGPEV TYEPPPTAPT GGGTHTCPPC
151  PAPELLGGPS VFLFPPKPKD TLMISRTPEV TCVVVDVSHE DPEVKFNWYV
201  DGVEVHNAKT KPREEQYNST YRVVSVLTVL HQDWLNGKEY KCKVSNKALP
251  APIEKTISKA KGQPREPQVY TLPPCREEMT ENQVSLWCLV KGFYPSDIAV
301  EWESNGQPEN NYKTTPPVLD SDGSFFLYSK LTVDKSRWQQ GNVFSCSVMH
351  EALHNHYTQD SLSLSPG
```

The leader sequence and linker are underlined. To promote formation of the ALK4-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by doubleunderline above. To facilitate purification of the ALK4-Fc:ActRIIB-Fc heterodimer, two amino acid substitutions (replacing lysines with acidic amino acids) can also be introduced into the Fc domain of the fusion protein as indicated by doubleunderline above. The amino acid sequence of SEQ ID NO: 70 may optionally be provided with a lysine added at the C-terminus.

This ActRIIB-Fc fusion protein is encoded by the following nucleic acid (SEQ ID NO: 71):

```
                                            (SEQ ID NO: 71)
  1  ATGGATGCAA TGAAGAGAGG GCTCTGCTGT GTGCTGCTGC TGTGTGGAGC
 51  AGTCTTCGTT TCGCCCGGCG CCTCTGGGCG TGGGGAGGCT GAGACACGGG
101  AGTGCATCTA CTACAACGCC AACTGGGAGC TGGAGCGCAC CAACCAGAGC
151  GGCCTGGAGC GCTGCGAAGG CGAGCAGGAC AAGCGGCTGC ACTGCTACGC
201  CTCCTGGCGC AACAGCTCTG GCACCATCGA GCTCGTGAAG AAGGGCTGCT
251  GGCTAGATGA CTTCAACTGC TACGATAGGC AGGAGTGTGT GGCCACTGAG
301  GAGAACCCCC AGGTGTACTT CTGCTGCTGT GAAGGCAACT TCTGCAACGA
351  GCGCTTCACT CATTTGCCAG AGGCTGGGGG CCCGGAAGTC ACGTACGAGC
```

-continued

```
 401  CACCCCCGAC AGCCCCCACC GGTGGTGGAA CTCACACATG CCCACCGTGC
 451  CCAGCACCTG AACTCCTGGG GGGACCGTCA GTCTTCCTCT TCCCCCCAAA
 501  ACCCAAGGAC ACCCTCATGA TCTCCCGGAC CCCTGAGGTC ACATGCGTGG
 551  TGGTGGACGT GAGCCACGAA GACCCTGAGG TCAAGTTCAA CTGGTACGTG
 601  GACGGCGTGG AGGTGCATAA TGCCAAGACA AAGCCGCGGG AGGAGCAGTA
 651  CAACAGCACG TACCGTGTGG TCAGCGTCCT CACCGTCCTG CACCAGGACT
 701  GGCTGAATGG CAAGGAGTAC AAGTGCAAGG TCTCCAACAA AGCCCTCCCA
 751  GCCCCCATCG AGAAAACCAT CTCCAAAGCC AAAGGGCAGC CCCGAGAACC
 801  ACAGGTGTAC ACCCTGCCCC CATGCCGGGA GGAGATGACC GAGAACCAGG
 851  TCAGCCTGTG GTGCCTGGTC AAAGGCTTCT ATCCCAGCGA CATCGCCGTG
 901  GAGTGGGAGA GCAATGGGCA GCCGGAGAAC AACTACAAGA CCACGCCTCC
 951  CGTGCTGGAC TCCGACGGCT CCTTCTTCCT CTATAGCAAG CTCACCGTGG
1001  ACAAGAGCAG GTGGCAGCAG GGGAACGTCT TCTCATGCTC CGTGATGCAT
1051  GAGGCTCTGC ACAACCACTA CACGCAGGAC AGCCTCTCCC TGTCTCCGGG
1101  T
```

The mature ActRIIB-Fc fusion polypeptide is as follows (SEQ ID NO: 72) and may optionally be provided with a lysine added to the C-terminus.

```
                                                     (SEQ ID NO: 72)
  1  GRGEAETREC IYYNANWELE RTNQSGLERC EGEQDKRLHC YASWRNSSGT
 51  IELVKKGCWL DDFNCYDRQE CVATEENPQV YFCCCEGNFC NERFTHLPEA
101  GGPEVTYEPP PTAPTGGGTH TCPPCPAPEL LGGPSVFLFP PKPKDTLMIS
151  RTPEVTCVVV DVSHEDPEVK FNWYVDGVEV HNAKTKPREE QYNSTYRVVS
201  VLTVLHQDWL NGKEYKCKVS NKALPAPIEK TISKAKGQPR EPQVYTLPPC
251  REEMTENQVS LWCLVKGFYP SDIAVEWESN GQPENNYKTT PPVLDSDGSF
301  FLYSKLTVDK SRWQQGNVFS CSVMHEALHN HYTQDSLSLS PG
```

This ActRIIB-Fc fusion polypeptide is encoded by the following nucleic acid (SEQ ID NO: 73):

```
                                                     (SEQ ID NO: 73)
   1  GGGCGTGGGG AGGCTGAGAC ACGGGAGTGC ATCTACTACA ACGCCAACTG
  51  GGAGCTGGAG CGCACCAACC AGAGCGGCCT GGAGCGCTGC GAAGGCGAGC
 101  AGGACAAGCG GCTGCACTGC TACGCCTCCT GGCGCAACAG CTCTGGCACC
 151  ATCGAGCTCG TGAAGAAGGG CTGCTGGCTA GATGACTTCA ACTGCTACGA
 201  TAGGCAGGAG TGTGTGGCCA CTGAGGAGAA CCCCCAGGTG TACTTCTGCT
 251  GCTGTGAAGG CAACTTCTGC AACGAGCGCT TCACTCATTT GCCAGAGGCT
 301  GGGGGCCCGG AAGTCACGTA CGAGCCACCC CCGACAGCCC CCACCGGTGG
 351  TGGAACTCAC ACATGCCCAC CGTGCCCAGC ACCTGAACTC CTGGGGGGAC
 401  CGTCAGTCTT CCTCTTCCCC CCAAAACCCA AGGACACCCT CATGATCTCC
 451  CGGACCCCTG AGGTCACATG CGTGGTGGTG GACGTGAGCC ACGAAGACCC
 501  TGAGGTCAAG TTCAACTGGT ACGTGGACGG CGTGGAGGTG CATAATGCCA
```

-continued

```
551   AGACAAAGCC GCGGGAGGAG CAGTACAACA GCACGTACCG TGTGGTCAGC
601   GTCCTCACCG TCCTGCACCA GGACTGGCTG AATGGCAAGG AGTACAAGTG
651   CAAGGTCTCC AACAAAGCCC TCCCAGCCCC CATCGAGAAA ACCATCTCCA
701   AAGCCAAAGG GCAGCCCCGA GAACCACAGG TGTACACCCT GCCCCCATGC
751   CGGGAGGAGA TGACCGAGAA CCAGGTCAGC CTGTGGTGCC TGGTCAAAGG
801   CTTCTATCCC AGCGACATCG CCGTGGAGTG GGAGAGCAAT GGGCAGCCGG
851   AGAACAACTA CAAGACCACG CCTCCCGTGC TGGACTCCGA CGGCTCCTTC
901   TTCCTCTATA GCAAGCTCAC CGTGGACAAG AGCAGGTGGC AGCAGGGGAA
951   CGTCTTCTCA TGCTCCGTGA TGCATGAGGC TCTGCACAAC CACTACACGC
1001  AGGACAGCCT CTCCCTGTCT CCGGGT
```

The complementary form of ALK4-Fc fusion polypeptide (SEQ ID NO: 74) is as follows and may optionally be provided with lysine removed from the C-terminus.

```
                                                       (SEQ ID NO: 74)
1     MDAMKRGLCC VLLLCGAVFV SPGASGPRGV QALLCACTSC LQANYTCETD
51    GACMVSIFNL DGMEHHVRTC IPKVELVPAG KPFYCLSSED LRNTHCCYTD
101   YCNRIDLRVP SGHLKEPEHP SMWGPVETGG GTHTCPPCPA PELLGGPSVF
151   LFPPKPKDTL MISRTPEVTC VVVDVSHEDP EVKFNWYVDG VEVHNAKTKP
201   REEQYNSTYR VVSVLTVLHQ DWLNGKEYKC KVSNKALPAP IEKTISKAKG
251   QPREPQVCTL PPSREEMTKN QVSLSCAVKG FYPSDIAVEW ESRGQPENNY
301   KTTPPVLDSR GSFFLVSKLT VDKSRWQQGN VFSCSVMHEA LHNHYTQKSL
351   SLSPGK
```

The leader sequence and the linker are underlined. To guide heterodimer formation with the ActRIIB-Fc fusion polypeptide of SEQ ID NOs: 70 and 72 above, four amino acid substitutions (replacing a tyrosine with a cysteine, a threonine with a serine, a leucine with an alanine, and a tyrosine with a valine) can be introduced into the Fc domain of the ALK4 fusion polypeptide as indicated by doubleunderline above. To facilitate purification of the ALK4-Fc:ActRIIB-Fc heterodimer, two amino acid substitutions (replacing an asparagine with an arginine and an aspartate with an arginine) can also be introduced into the Fc domain of the ALK4-Fc fusion polypeptide as indicated by doubleunderline above. The amino acid sequence of SEQ ID NO: 74 may optionally be provided with lysine removed from the C-terminus.

This ALK4-Fc fusion polypeptide is encoded by the following nucleic acid (SEQ ID NO: 75):

```
                                                       (SEQ ID NO: 75)
1     ATGGATGCAA TGAAGAGAGG GCTCTGCTGT GTGCTGCTGC TGTGTGGAGC
51    AGTCTTCGTT TCGCCCGGCG CCTCCGGGCC CCGGGGGGTC CAGGCTCTGC
101   TGTGTGCGTG CACCAGCTGC CTCCAGGCCA ACTACACGTG TGAGACAGAT
151   GGGGCCTGCA TGGTTTCCAT TTTCAATCTG GATGGGATGG AGCACCATGT
201   GCGCACCTGC ATCCCCAAAG TGGAGCTGGT CCCTGCCGGG AAGCCCTTCT
251   ACTGCCTGAG CTCGGAGGAC CTGCGCAACA CCCACTGCTG CTACACTGAC
301   TACTGCAACA GGATCGACTT GAGGGTGCCC AGTGGTCACC TCAAGGAGCC
351   TGAGCACCCG TCCATGTGGG GCCCGGTGGA GACCGGTGGT GGAACTCACA
401   CATGCCCACC GTGCCCAGCA CCTGAACTCC TGGGGGGACC GTCAGTCTTC
451   CTCTTCCCCC CAAAACCCAA GGACACCCTC ATGATCTCCC GGACCCCTGA
501   GGTCACATGC GTGGTGGTGG ACGTGAGCCA CGAAGACCCT GAGGTCAAGT
```

-continued

```
551   TCAACTGGTA CGTGGACGGC GTGGAGGTGC ATAATGCCAA GACAAAGCCG
601   CGGGAGGAGC AGTACAACAG CACGTACCGT GTGGTCAGCG TCCTCACCGT
651   CCTGCACCAG GACTGGCTGA ATGGCAAGGA GTACAAGTGC AAGGTCTCCA
701   ACAAAGCCCT CCCAGCCCCC ATCGAGAAAA CCATCTCCAA AGCCAAAGGG
751   CAGCCCCGAG AACCACAGGT GTGCACCCTG CCCCCATCCC GGGAGGAGAT
801   GACCAAGAAC CAGGTCAGCC TGTCCTGCGC CGTCAAAGGC TTCTATCCCA
851   GCGACATCGC CGTGGAGTGG GAGAGCCGCG GGCAGCCGGA GAACAACTAC
901   AAGACCACGC CTCCCGTGCT GGACTCCCGC GGCTCCTTCT TCCTCGTGAG
951   CAAGCTCACC GTGGACAAGA GCAGGTGGCA GCAGGGGAAC GTCTTCTCAT
1001  GCTCCGTGAT GCATGAGGCT CTGCACAACC ACTACACGCA GAAGAGCCTC
1051  TCCCTGTCTC CGGGTAAA
```

The mature ALK4-Fc fusion polypeptide sequence is as follows (SEQ ID NO: 76) and may optionally be provided with lysine removed from the C-terminus.

```
                                              (SEQ ID NO: 76)
1     SGPRGVQALL CACTSCLQAN YTCETDGACM VSIFNLDGME HHVRTCIPKV
51    ELVPAGKPFY CLSSEDLRNT HCCYTDYCNR IDLRVPSGHL KEPEHPSMWG
101   PVETGGGTHT CPPCPAPELL GGPSVFLFPP KPKDTLMISR TPEVTCVVVD
151   VSHEDPEVKF NWYVDGVEVH NAKTKPREEQ YNSTYRVVSV LTVLHQDWLN
201   GKEYKCKVSN KALPAPIEKT ISKAKGQPRE PQVCTLPPSR EEMTKNQVSL
251   SCAVKGFYPS DIAVEWESRG QPENNYKTTP PVLDSRGSFF LVSKLTVDKS
301   RWQQGNVFSC SVMHEALHNH YTQKSLSLSP GK
```

This ALK4-Fc fusion polypeptide is encoded by the following nucleic acid (SEQ ID NO: 77):

```
                                                 (SEQ ID NO: 77)
1     TCCGGGCCCC GGGGGGTCCA GGCTCTGCTG TGTGCGTGCA CCAGCTGCCT
51    CCAGGCCAAC TACACGTGTG AGACAGATGG GGCCTGCATG GTTTCCATTT
101   TCAATCTGGA TGGGATGGAG CACCATGTGC GCACCTGCAT CCCCAAAGTG
151   GAGCTGGTCC CTGCCGGGAA GCCCTTCTAC TGCCTGAGCT CGGAGGACCT
201   GCGCAACACC CACTGCTGCT ACACTGACTA CTGCAACAGG ATCGACTTGA
251   GGGTGCCCAG TGGTCACCTC AAGGAGCCTG AGCACCCGTC CATGTGGGGC
301   CCGGTGGAGA CCGGTGGTGG AACTCACACA TGCCCACCGT GCCCAGCACC
351   TGAACTCCTG GGGGGACCGT CAGTCTTCCT CTTCCCCCCA AAACCCAAGG
401   ACACCCTCAT GATCTCCCGG ACCCCTGAGG TCACATGCGT GGTGGTGGAC
451   GTGAGCCACG AAGACCCTGA GGTCAAGTTC AACTGGTACG TGGACGGCGT
501   GGAGGTGCAT AATGCCAAGA CAAAGCCGCG GGAGGAGCAG TACAACAGCA
551   CGTACCGTGT GGTCAGCGTC CTCACCGTCC TGCACCAGGA CTGGCTGAAT
601   GGCAAGGAGT ACAAGTGCAA GGTCTCCAAC AAAGCCCTCC CAGCCCCCAT
651   CGAGAAAACC ATCTCCAAAG CCAAAGGGCA GCCCCGAGAA CCACAGGTGT
701   GCACCCTGCC CCCATCCCGG GAGGAGATGA CCAAGAACCA GGTCAGCCTG
751   TCCTGCGCCG TCAAAGGCTT CTATCCCAGC GACATCGCCG TGGAGTGGGA
```

-continued

```
801     GAGCCGCGGG CAGCCGGAGA ACAACTACAA GACCACGCCT CCCGTGCTGG

851     ACTCCCGCGG CTCCTTCTTC CTCGTGAGCA AGCTCACCGT GGACAAGAGC

901     AGGTGGCAGC AGGGGAACGT CTTCTCATGC TCCGTGATGC ATGAGGCTCT

951     GCACAACCAC TACACGCAGA AGAGCCTCTC CCTGTCTCCG GGTAAA
```

ActRIIB-Fc and ALK4-Fc proteins of SEQ ID NO: 72 and SEQ ID NO: 76, respectively, may be co-expressed and purified from a CHO cell line, to give rise to a heteromeric complex comprising ALK4-Fc:ActRIIB-Fc.

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography, cation exchange chromatography, epitope-based affinity chromatography (e.g., with an antibody or functionally equivalent ligand directed against an epitope on ALK4 or ActRIIB), and multimodal chromatography (e.g., with resin containing both electrostatic and hydrophobic ligands). The purification could be completed with viral filtration and buffer exchange.

In another approach to promote the formation of heteromultimer complexes using asymmetric Fc fusion proteins, the Fc domains are altered to introduce complementary hydrophobic interactions, an additional intermolecular disulfide bond, and a histidine-to-arginine substitution specifically in the ActRIIB-Fc polypeptide chain for facilitating purification based on protein A affinity, as illustrated in the ActRIIB-Fc polypeptide sequences of SEQ ID NOs: 78-81 and the ALK4-Fc polypeptide sequences of SEQ ID NOs: 47, 48, 82, and 83. The ActRIIB-Fc fusion polypeptide and ALK4-Fc fusion polypeptide each employ the TPA leader:

(SEQ ID NO: 38)
MDAMKRGLCCVLLLCGAVFVSP.

The ActRIIB-Fc polypeptide sequence (SEQ ID NO: 78) is shown below:

(SEQ ID NO: 78)

```
  1     MDAMKRGLCC VLLLCGAVFV SPGASGRGEA ETRECIYYNA NWELERTNQS

 51     GLERCEGEQD KRLHCYASWR NSSGTIELVK KGCWLDDFNC YDRQECVATE

101     ENPQVYFCCC EGNFCNERFT HLPEAGGPEV TYEPPPTAPT GGGTHTCPPC

151     PAPELLGGPS VFLFPPKPKD TLMISRTPEV TCVVVDVSHE DPEVKFNWYV

201     DGVEVHNAKT KPREEQYNST YRVVSVLTVL HQDWLNGKEY KCKVSNKALP

251     APIEKTISKA KGQPREPQVY TLPPCREEMT KNQVSLWCLV KGFYPSDIAV

301     EWESNGQPEN NYKTTPPVLD SDGSFFLYSK LTVDKSRWQQ GNVFSCSVMH

351     EALHNRYTQK SLSLSPGK
```

The leader sequence and linker are underlined. To promote formation of the ALK4-Fc:ActRIIB-Fc heterodimer rather than either of the possible homodimeric complexes, two amino acid substitutions (replacing a serine with a cysteine and a threonine with a trytophan) can be introduced into the Fc domain of the ActRIIB-Fc fusion polypeptide as indicated by doubleunderline above. Another amino acid substitution (replacing histidine with arginine) can also be introduced into the Fc domain of the fusion protein as indicated by doubleunderline above to facilitate purification of the ALK4-Fc:ActRIIB-Fc heterodimer. The amino acid sequence of SEQ ID NO: 78 may optionally be provided with lysine removed from the C-terminus.

This ActRIIB-Fc fusion protein is encoded by the following nucleic acid (SEQ ID NO: 79):

```
                                                    (SEQ ID NO: 79)
   1  ATGGATGCAA TGAAGAGAGG GCTCTGCTGT GTGCTGCTGC TGTGTGGAGC
  51  AGTCTTCGTT TCGCCCGGCG CCTCTGGGCG TGGGGAGGCT GAGACACGGG
 101  AGTGCATCTA CTACAACGCC AACTGGGAGC TGGAGCGCAC CAACCAGAGC
 151  GGCCTGGAGC GCTGCGAAGG CGAGCAGGAC AAGCGGCTGC ACTGCTACGC
 201  CTCCTGGCGC AACAGCTCTG GCACCATCGA GCTCGTGAAG AAGGGCTGCT
 251  GGCTAGATGA CTTCAACTGC TACGATAGGC AGGAGTGTGT GGCCACTGAG
 301  GAGAACCCCC AGGTGTACTT CTGCTGCTGT GAAGGCAACT TCTGCAACGA
 351  GCGCTTCACT CATTTGCCAG AGGCTGGGGG CCCGGAAGTC ACGTACGAGC
 401  CACCCCCGAC AGCCCCCACC GGTGGTGGAA CTCACACATG CCCACCGTGC
 451  CCAGCACCTG AACTCCTGGG GGGACCGTCA GTCTTCCTCT TCCCCCCAAA
 501  ACCCAAGGAC ACCCTCATGA TCTCCCGGAC CCCTGAGGTC ACATGCGTGG
 551  TGGTGGACGT GAGCCACGAA GACCCTGAGG TCAAGTTCAA CTGGTACGTG
 601  GACGGCGTGG AGGTGCATAA TGCCAAGACA AAGCCGCGGG AGGAGCAGTA
 651  CAACAGCACG TACCGTGTGG TCAGCGTCCT CACCGTCCTG CACCAGGACT
 701  GGCTGAATGG CAAGGAGTAC AAGTGCAAGG TCTCCAACAA AGCCCTCCCA
 751  GCCCCCATCG AGAAAACCAT CTCCAAAGCC AAAGGGCAGC CCCGAGAACC
 801  ACAGGTGTAC ACCCTGCCCC CATGCCGGGA GGAGATGACC AAGAACCAGG
 851  TCAGCCTGTG GTGCCTGGTC AAAGGCTTCT ATCCCAGCGA CATCGCCGTG
 901  GAGTGGGAGA GCAATGGGCA GCCGGAGAAC AACTACAAGA CCACGCCTCC
 951  CGTGCTGGAC TCCGACGGCT CCTTCTTCCT CTATAGCAAG CTCACCGTGG
1001  ACAAGAGCAG GTGGCAGCAG GGGAACGTCT TCTCATGCTC CGTGATGCAT
1051  GAGGCTCTGC ACAACCGCTA CACGCAGAAG AGCCTCTCCC TGTCTCCGGG
1101  TAAA
```

The mature ActRIIB-Fc fusion polypeptide is as follows (SEQ ID NO: 80) and may optionally be provided with lysine removed from the C-terminus.

```
                                                    (SEQ ID NO: 80)
   1  GRGEAETREC IYYNANWELE RTNQSGLERC EGEQDKRLHC YASWRNSSGT
  51  IELVKKGCWL DDFNCYDRQE CVATEENPQV YFCCCEGNFC NERFTHLPEA
 101  GGPEVTYEPP PTAPTGGGTH TCPPCPAPEL LGGPSVFLFP PKPKDTLMIS
 151  RTPEVTCVVV DVSHEDPEVK FNWYVDGVEV HNAKTKPREE QYNSTYRVVS
 201  VLTVLHQDWL NGKEYKCKVS NKALPAPIEK TISKAKGQPR EPQVYTLPPC
 251  REEMTKNQVS LWCLVKGFYP SDIAVEWESN GQPENNYKTT PPVLDSDGSF
 301  FLYSKLTVDK SRWQQGNVFS CSVMHEALHN RYTQKSLSLS PGK
```

This ActRIIB-Fc fusion polypeptide is encoded by the following nucleic acid (SEQ ID NO: 81):

```
                                                (SEQ ID NO: 81)
   1  GGGCGTGGGG AGGCTGAGAC ACGGGAGTGC ATCTACTACA ACGCCAACTG

  51  GGAGCTGGAG CGCACCAACC AGAGCGGCCT GGAGCGCTGC GAAGGCGAGC

 101  AGGACAAGCG GCTGCACTGC TACGCCTCCT GGCGCAACAG CTCTGGCACC

 151  ATCGAGCTCG TGAAGAAGGG CTGCTGGCTA GATGACTTCA ACTGCTACGA

 201  TAGGCAGGAG TGTGTGGCCA CTGAGGAGAA CCCCCAGGTG TACTTCTGCT

 251  GCTGTGAAGG CAACTTCTGC AACGAGCGCT TCACTCATTT GCCAGAGGCT

 301  GGGGGCCCGG AAGTCACGTA CGAGCCACCC CCGACAGCCC CCACCGGTGG

 351  TGGAACTCAC ACATGCCCAC CGTGCCCAGC ACCTGAACTC CTGGGGGGAC

 401  CGTCAGTCTT CCTCTTCCCC CCAAAACCCA AGGACACCCT CATGATCTCC

 451  CGGACCCCTG AGGTCACATG CGTGGTGGTG GACGTGAGCC ACGAAGACCC

 501  TGAGGTCAAG TTCAACTGGT ACGTGGACGG CGTGGAGGTG CATAATGCCA

 551  AGACAAAGCC GCGGGAGGAG CAGTACAACA GCACGTACCG TGTGGTCAGC

 601  GTCCTCACCG TCCTGCACCA GGACTGGCTG AATGGCAAGG AGTACAAGTG

 651  CAAGGTCTCC AACAAAGCCC TCCCAGCCCC CATCGAGAAA ACCATCTCCA

 701  AAGCCAAAGG GCAGCCCCGA GAACCACAGG TGTACACCCT GCCCCCATGC

 751  CGGGAGGAGA TGACCAAGAA CCAGGTCAGC CTGTGGTGCC TGGTCAAAGG

 801  CTTCTATCCC AGCGACATCG CCGTGGAGTG GGAGAGCAAT GGGCAGCCGG

 851  AGAACAACTA CAAGACCACG CCTCCCGTGC TGGACTCCGA CGGCTCCTTC

 901  TTCCTCTATA GCAAGCTCAC CGTGGACAAG AGCAGGTGGC AGCAGGGGAA

 951  CGTCTTCTCA TGCTCCGTGA TGCATGAGGC TCTGCACAAC CGCTACACGC

1001  AGAAGAGCCT CTCCCTGTCT CCGGGTAAA
```

The complementary form of ALK4-Fc fusion polypeptide is SEQ ID NO: 47 (shown above), which contains four amino acid substitutions to guide heterodimer formation with the ActRIIB-Fc fusion polypeptide of SEQ ID NOs: 78 and 80 and may optionally be provided with lysine removed from the C-terminus.

This ALK4-Fc fusion polypeptide is encoded by the following nucleic acid (SEQ ID NO: 82):

```
                                                 (SEQ ID NO: 82)
   1   ATGGATGCAA TGAAGAGAGG GCTCTGCTGT GTGCTGCTGC TGTGTGGAGC

  51   AGTCTTCGTT TCGCCCGGCG CCTCCGGGCC CCGGGGGGTC CAGGCTCTGC

 101   TGTGTGCGTG CACCAGCTGC CTCCAGGCCA ACTACACGTG TGAGACAGAT

 151   GGGGCCTGCA TGGTTTCCAT TTTCAATCTG GATGGGATGG AGCACCATGT

 201   GCGCACCTGC ATCCCCAAAG TGGAGCTGGT CCCTGCCGGG AAGCCCTTCT

 251   ACTGCCTGAG CTCGGAGGAC CTGCGCAACA CCCACTGCTG CTACACTGAC

 301   TACTGCAACA GGATCGACTT GAGGGTGCCC AGTGGTCACC TCAAGGAGCC

 351   TGAGCACCCG TCCATGTGGG GCCCGGTGGA GACCGGTGGT GGAACTCACA

 401   CATGCCCACC GTGCCCAGCA CCTGAACTCC TGGGGGGACC GTCAGTCTTC

 451   CTCTTCCCCC CAAAACCCAA GGACACCCTC ATGATCTCCC GGACCCCTGA

 501   GGTCACATGC GTGGTGGTGG ACGTGAGCCA CGAAGACCCT GAGGTCAAGT
```

-continued

```
551   TCAACTGGTA CGTGGACGGC GTGGAGGTGC ATAATGCCAA GACAAAGCCG
601   CGGGAGGAGC AGTACAACAG CACGTACCGT GTGGTCAGCG TCCTCACCGT
651   CCTGCACCAG GACTGGCTGA ATGGCAAGGA GTACAAGTGC AAGGTCTCCA
701   ACAAAGCCCT CCCAGCCCCC ATCGAGAAAA CCATCTCCAA AGCCAAAGGG
751   CAGCCCCGAG AACCACAGGT GTGCACCCTG CCCCCATCCC GGGAGGAGAT
801   GACCAAGAAC CAGGTCAGCC TGTCCTGCGC CGTCAAAGGC TTCTATCCCA
851   GCGACATCGC CGTGGAGTGG GAGAGCAATG GGCAGCCGGA GAACAACTAC
901   AAGACCACGC CTCCCGTGCT GGACTCCGAC GGCTCCTTCT TCCTCGTGAG
951   CAAGCTCACC GTGGACAAGA GCAGGTGGCA GCAGGGGAAC GTCTTCTCAT
1001  GCTCCGTGAT GCATGAGGCT CTGCACAACC ACTACACGCA GAAGAGCCTC
1051  TCCCTGTCTC CGGGTAAA
```

The mature ALK4-Fc fusion polypeptide sequence is SEQ ID NO: 48 (shown above) and may optionally be provided with lysine removed from the C-terminus.

This ALK4-Fc fusion polypeptide is encoded by the following nucleic acid (SEQ ID NO: 83):

```
                                                (SEQ ID NO: 83)
1     TCCGGGCCCC GGGGGGTCCA GGCTCTGCTG TGTGCGTGCA CCAGCTGCCT
51    CCAGGCCAAC TACACGTGTG AGACAGATGG GGCCTGCATG GTTTCCATTT
101   TCAATCTGGA TGGGATGGAG CACCATGTGC GCACCTGCAT CCCCAAAGTG
151   GAGCTGGTCC CTGCCGGGAA GCCCTTCTAC TGCCTGAGCT CGGAGGACCT
201   GCGCAACACC CACTGCTGCT ACACTGACTA CTGCAACAGG ATCGACTTGA
251   GGGTGCCCAG TGGTCACCTC AAGGAGCCTG AGCACCCGTC CATGTGGGGC
301   CCGGTGGAGA CCGGTGGTGG AACTCACACA TGCCCACCGT GCCCAGCACC
351   TGAACTCCTG GGGGGACCGT CAGTCTTCCT CTTCCCCCCA AAACCCAAGG
401   ACACCCTCAT GATCTCCCGG ACCCCTGAGG TCACATGCGT GGTGGTGGAC
451   GTGAGCCACG AAGACCCTGA GGTCAAGTTC AACTGGTACG TGGACGGCGT
501   GGAGGTGCAT AATGCCAAGA CAAAGCCGCG GGAGGAGCAG TACAACAGCA
551   CGTACCGTGT GGTCAGCGTC CTCACCGTCC TGCACCAGGA CTGGCTGAAT
601   GGCAAGGAGT ACAAGTGCAA GGTCTCCAAC AAAGCCCTCC CAGCCCCCAT
651   CGAGAAAACC ATCTCCAAAG CCAAAGGGCA GCCCCGAGAA CCACAGGTGT
701   GCACCCTGCC CCCATCCCGG GAGGAGATGA CCAAGAACCA GGTCAGCCTG
751   TCCTGCGCCG TCAAAGGCTT CTATCCCAGC GACATCGCCG TGGAGTGGGA
801   GAGCAATGGG CAGCCGGAGA ACAACTACAA GACCACGCCT CCCGTGCTGG
851   ACTCCGACGG CTCCTTCTTC CTCGTGAGCA AGCTCACCGT GGACAAGAGC
901   AGGTGGCAGC AGGGGAACGT CTTCTCATGC TCCGTGATGC ATGAGGCTCT
951   GCACAACCAC TACACGCAGA AGAGCCTCTC CCTGTCTCCG GGTAAA
```

ActRIIB-Fc and ALK4-Fc proteins of SEQ ID NO: 80 and SEQ ID NO: 48, respectively, may be co-expressed and purified from a CHO cell line, to give rise to a heteromeric complex comprising ALK4-Fc:ActRIIB-Fc.

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography and epitope-based affinity chromatography (e.g., with an antibody or functionally equivalent ligand directed against an epitope on ALK4 or ActRIIB), and multimodal chromatography (e.g., with resin containing both electrostatic and hydrophobic ligands). The purification could be completed with viral filtration and buffer exchange.

Example 2. Ligand Binding Profile of ALK4-Fc:ActRIIB-Fc Heterodimer Compared to ActRIIB-Fc Homodimer and ALK4-Fc Homodimer A Biacore™-based binding assay was used to compare ligand binding selectivity of the ALK4-Fc:ActRIIB-Fc heterodimeric complex described above with that of ActRIIB-Fc and ALK4-Fc homodimer complexes. The ALK4-Fc:ActRIIB-Fc heterodimer, ActRIIB-Fc homodimer, and ALK4-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted by gray shading.

Ligand binding profile of ALK4-Fc: ActRIIB-Fc heterodimer compared to ActRIIB-Fc homodimer and ALK4-Fc homodimer

| | ActRIIB-Fc homodimer | | | ALK4-Fc homodimer | | | ALK4-Fc: ActRIIB-Fc heterodimer | | |
|---|---|---|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | $2.3 \times 10^{-4}$ | 19 | $5.8 \times 10^5$ | $1.2 \times 10^{-2}$ | 20000 | $1.3 \times 10^7$ | $1.5 \times 10^{-4}$ | 12 |
| Activin B | $5.1 \times 10^6$ | $1.0 \times 10^{-4}$ | 20 | | No binding | | $7.1 \times 10^6$ | $4.0 \times 10^{-5}$ | 6 |
| BMP6 | $3.2 \times 10^7$ | $6.8 \times 10^{-3}$ | 190 | | — | | $2.0 \times 10^6$ | $5.5 \times 10^{-3}$ | 2700 |
| BMP9 | $1.4 \times 10^7$ | $1.1 \times 10^{-3}$ | 77 | | — | | Transient* | | 3400 |
| BMP10 | $2.3 \times 10^7$ | $2.6 \times 10^{-4}$ | 11 | | — | | $5.6 \times 10^7$ | $4.1 \times 10^{-3}$ | 74 |
| GDF3 | $1.4 \times 10^6$ | $2.2 \times 10^{-3}$ | 1500 | | — | | $3.4 \times 10^6$ | $1.7 \times 10^{-2}$ | 4900 |
| GDF8 | $8.3 \times 10^5$ | $2.3 \times 10^{-4}$ | 280 | $1.3 \times 10^5$ | $1.9 \times 10^{-3}$ | 15000† | $3.9 \times 10^5$ | $2.1 \times 10^{-4}$ | 550 |
| GDF11 | $5.0 \times 10^7$ | $1.1 \times 10^{-4}$ | 2 | $5.0 \times 10^6$ | $4.8 \times 10^{-3}$ | 270† | $3.8 \times 10^7$ | $1.1 \times 10^{-4}$ | 3 |

Figure 4:
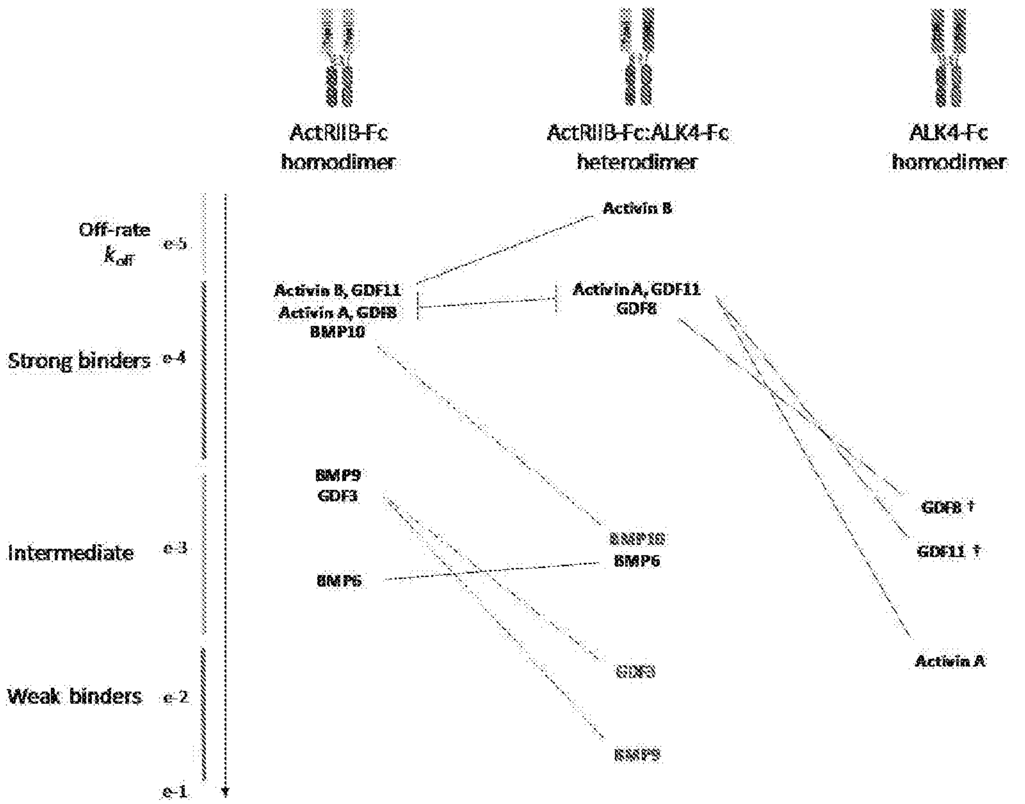
FIG. 4 shows comparative ligand binding data for an ALK4-Fc:ActRIIB-Fc heterodimeric protein complex compared to ActRIIB-Fc homodimer and ALK4-Fc homodimer. For each protein complex, ligands are ranked by $k_{off}$, a kinetic constant that correlates well with ligand signaling inhibition, and listed in descending order of binding affinity (ligands bound most tightly are listed at the top). At left, yellow, red, green, and blue lines indicate magnitude of the off-rate constant. Solid black lines indicate ligands whose binding to heterodimer is enhanced or unchanged compared with homodimer, whereas dashed red lines indicate substantially reduced binding compared with homodimer. As shown, the ALK4-Fc:ActRIIB-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. Like ActRIIB-Fc homodimer, the heterodimer retains intermediate-level binding to BMP6.

*Indeterminate due to transient nature of interaction
†Very low signal
—Not tested These comparative binding data demonstrate that ALK4-Fc:ActRIIB-Fc heterodimer has an altered binding profile/selectivity relative to either ActRIIB-Fc or ALK4-Fc homodimers. ALK4-Fc:ActRIIB-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. In particular, BMP9 displays low or no observable affinity for ALK4-Fc:ActRIIB-Fc heterodimer, whereas this ligand binds strongly to ALK4-Fc:ActRIIB-Fc heterodimer. Like the ActRIIB-Fc homodimer, the heterodimer retains intermediate-level binding to BMP6. See FIG. 4.

In addition, an A-204 Reporter Gene Assay was used to evaluate the effects of ALK4-Fc:ActRIIB-Fc heterodimer and ActRIIB-Fc:ActRIIB-Fc homodimer on signaling by activin A, activin B, GDF11, GDF8, BMP10, and BMP9. Cell line: Human Rhabdomyosarcoma (derived from muscle). Reporter vector: pGL3(CAGA)12 (as described in Dennler et al, 1998, EMBO 17: 3091-3100). The CAGA12 motif is present in TGF-beta responsive genes (PAI-1 gene), so this vector is of general use for factors signaling through Smad2 and 3. An exemplary A-204 Reporter Gene Assay is outlined below.

Day 1: Split A-204 cells into 48-well plate.

Day 2: A-204 cells transfected with 10 ug pGL3(CAGA)12 or pGL3(CAGA)12(10 ug)+pRLCMV (1 ug) and Fugene.

Day 3: Add factors (diluted into medium+0.1% BSA). Inhibitors need to be pre-incubated with Factors for about one hr before adding to cells. About six hrs later, cells are rinsed with PBS and then lysed.

Following the above steps, applicant performed a Luciferase assay.

Figure 7:
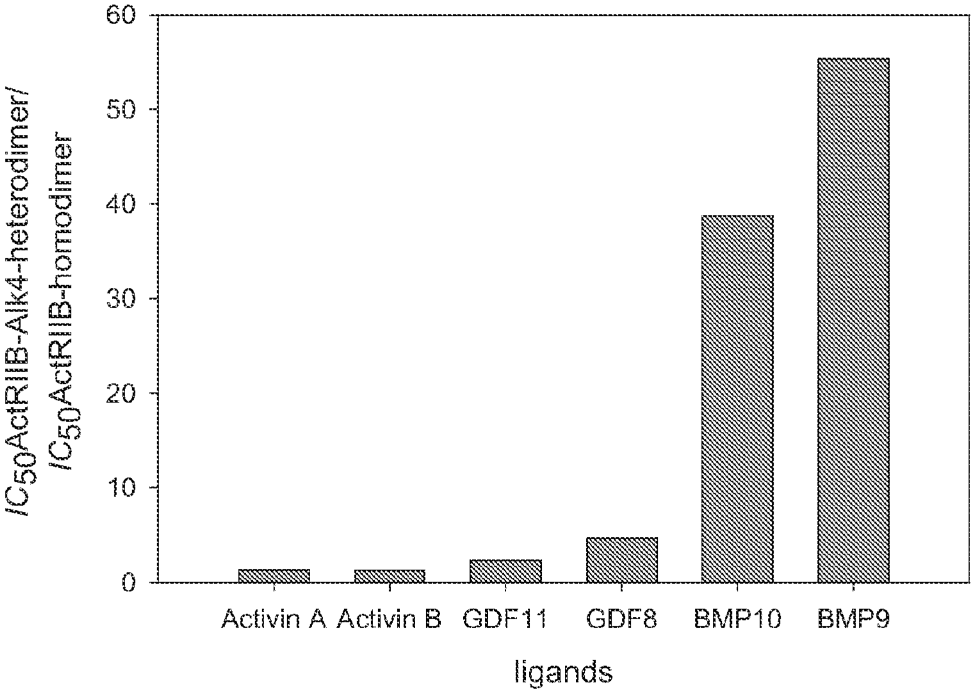
FIG. 7 shows comparative ALK4-Fc:ActRIIB-Fc heterodimer/ActRIIB-Fc:ActRIIB-Fc homodimer $IC_{50}$ data as determined by an A-204 Reporter Gene Assay as described herein. ALK4-Fc:ActRIIB-Fc heterodimer inhibits activin A, activin B, GDF8, and GDF11 signaling pathways similarly to the ActRIIB-Fc:ActRIIB-Fc homodimer. However, ALK4-Fc:ActRIIB-Fc heterodimer inhibition of BMP9 and BMP10 signaling pathways is significantly reduced compared to the ActRIIB-Fc:ActRIIB-Fc homodimer. These data demonstrate that ALK4:ActRIIB heterodimers are more selective antagonists of activin A, activin B, GDF8, and GDF11 compared to corresponding ActRIIB:ActRIIB homodimers.

Both the ALK4-Fc:ActRIIB-Fc heterodimer and ActRIIB-Fc:ActRIIB-Fc homodimer were determined to be potent inhibitors of activin A, activin B, GDF11, and GDF8 in this assay. In particular, as can be seen in the comparative homodimer/heterodimer $IC_{50}$ data illustrated in FIG. 7, ALK4-Fc:ActRIIB-Fc heterodimer inhibits activin A, activin B, GDF8, and GDF11 signaling pathways similarly to the ActRIIB-Fc:ActRIIB-Fc homodimer. However, ALK4-Fc:ActRIIB-Fc heterodimer inhibition of BMP9 and BMP10 signaling pathways is significantly reduced compared to the ActRIIB-Fc:ActRIIB-Fc homodimer. This data is consistent with the above-discussed binding data in which it was observed that both the ALK4-Fc:ActRIIB-Fc heterodimer and ActRIIB-Fc:ActRIIB-Fc homodimer display strong binding to activin A, activin B, GDF8, and GDF11, but BMP10 and BMP9 have significantly reduced affinity for the ALK4-Fc:ActRIIB-Fc heterodimer compared to the ActRIIB-Fc:ActRIIB-Fc homodimer.

To reduce the risk of potential adverse immune-related events in mouse studies described herein, ALK4-Fc:ActRIIB-Fc heterodimers were generated using the human ALK4 and human ActRIIB extracellular domains and linker domains as described above but were instead fused to mouse Fc fusion domains. The mouse Fc fusion domains were modified as described above to promote heteromultimer formation. This construct is designated as ALK4-mFc:ActRIIB-mFc.

Together, these data therefore demonstrate that ALK4-Fc:ActRIIB-Fc heterodimer is a more selective antagonist of activin B, activin A, GDF8, and GDF11 compared to ActRIIB-Fc homodimer. Accordingly, an ALK4-Fc:ActRIIB-Fc heterodimer will be more useful than an ActRIIB-Fc homodimer in certain applications where such selective antagonism is advantageous. Examples include therapeutic applications where it is desirable to retain antagonism of one or more of activin A, activin B, activin AB, GDF8, and GDF11 but minimize antagonism of one or more of BMP9, BMP10, GDF3, and BMP6.

Example 3. ALK4:ActRIIB Heteromultimer Treatment Improves Muscle Strength and Bone Mass in a Spinal Muscular Atrophy Model Motor neuron diseases (MND) such as spinal muscular atrophy (SMA) are characterized by loss of motor neurons resulting in muscular atrophy and weakness. Muscle weakness and bone loss are primary outcomes in patients with MND and result in decreased ambulation and increased morbidity. Therefore, therapeutic interventions are necessary that could increase muscle strength, reduce bone loss and prolong ambulation. The effects of the ALK4-mFc:ActRIIB-mFc was assessed in the SMA C/C mouse model [Min Liu et al. (2016) PLOS ONE. DOI:10.1371/journal.pone.0166803].

SMA C/C mice (21-week old, n=16) were randomized to receive either vehicle (PBS) or ALK4-mFc:ActRIIB-mFc. Dorsiflexion and tibialis anterior (TA) muscle contractility during isometric contraction was assessed by both in vivo and in situ methods. Bone mineral density (BMD) was measured by dual-energy x-ray absorptiometry. In ALK4-mFc:ActRIIB-mFc treated SMA animals, TA muscle mass was increased by 62% ($p<0.001$) and its physiological cross-sectional area (pCSA) was increased by 50% ($p<0.001$) compared to control mice. The increase in muscle mass correlated with an increase in strength, with maximum tetanic force improving by 25% ($p<0.01$) compared to control mice. The maximum rate of contraction and relaxation were accelerated by 28% and 38% respectively ($p<0.001$) in the ALK4-mFc:ActRIIB-mFc treated mice compared to vehicle group. The longitudinal alteration of dorsiflexion force after 6 weeks treatment compared to baseline was a −24% reduction in the vehicle group, compared to a 78% increase with ALK4-mFc:ActRIIB-mFc treatment. BMD of ALK4-mFc:ActRIIB-mFc treated SMA mice was improved by 11% compared with vehicle group ($p<0.001$).

Taken together, the data demonstrate that ALK4-mFc:ActRIIB-mFc therapy sustained muscle and bone parameters in SMA C/C mice. Therefore, the data indicate that ALK4-mFc:ActRIIB-mFc, and potentially other ALK4:ActRIIB antagonists, may be used as a therapy to treat SMA, particularly prolong ambulation and slow bone loss in SMA patients.

We claim:

1. A method of treating spinal muscular atrophy (SMA) in a patient in need thereof, comprising administering to the patient an effective amount of a recombinant ALK4:ActRIIB heteromultimer comprising at least one ALK4-Fc fusion protein and at least one ActRIIB-Fc fusion protein, wherein (A) the at least one ALK4-Fc fusion protein comprises an ALK4 polypeptide and an IgG1 Fc domain polypeptide, wherein the ALK4 polypeptide comprises an amino acid sequence selected from (i) an amino acid sequence at least 90% identical to amino acid residues 34-101 of SEQ ID NO: 9; and (ii) an amino acid sequence at least 90% identical to SEQ ID NO: 10; and (B) the at least one ActRIIB-Fc fusion protein comprises an ActRIIB polypeptide and an IgG1 Fc domain polypeptide, wherein the ActRIIB polypeptide comprises an amino acid sequence selected from (i) an amino acid sequence at least 90% identical to amino acid residues 29-109 of SEQ ID NO: 1;

(ii) an amino acid sequence at least 90% identical to SEQ ID NO: 2;

(iii) an amino acid sequence least sequence 90% identical to SEQ ID NO: 3;

(iv) an amino acid sequence as set forth in SEQ ID NO: 5;

(v) an amino acid as set forth in SEQ ID NO: 6;

wherein the Fc domain polypeptide of (a) one of the ALK4-Fc and the ActRIIB-Fc fusion proteins has an amino acid sequence of SEQ ID NO: 23 and the other has an amino acid sequence of SEQ ID NO: 24;

(b) one of the ALK4-Fc and the ActRIIB-Fc fusion proteins has an amino acid sequence of SEQ ID NO: 25 and the other has an amino acid sequence of SEQ ID NO: 26;

(c) one of the ALK4-Fc and the ActRIIB-Fc fusion proteins has an amino acid sequence of SEQ ID NO: 27 and the other has an amino acid sequence of SEQ ID NO: 28;

wherein the Fc domain polypeptide of one of the ALK4-Fc and the ActRIIB-Fc fusion proteins is optionally substituted at position H213 by an arginine (H213R); or (d) one of the ALK4-Fc and the ActRIIB-Fc fusion proteins has an amino acid sequence of SEQ ID NO: 66 and the other has an amino acid sequence of SEQ ID NO: 67;

wherein in (a)-(d), the Fc domain polypeptide may optionally be provided with the lysine (K) residue removed from the C-terminus.

2. The method of claim 1, wherein the method prevents or reduces the severity of one or more complications of SMA selected from the group consisting of: areflexia; overall muscle weakness; respiratory complications; respiratory failure; respiratory insufficiency; poor muscle tone; limpness or a tendency to flop; difficulty in achieving developmental milestones; difficulty in sitting, standing, or walking; loss of strength of respiratory muscles; fasciculation of the tongue; bone loss or weakness; difficulty in sucking or swallowing.

3. The method of claim 1, wherein patient has SMA3.

4. The method of claim 1, wherein the method increases bone mineral density in the patient.

5. The method of claim 1, wherein the method increases muscle mass in the patient.

6. The method of claim 1, wherein the method increases muscle strength in the patient.

7. The method of claim 1, wherein the method results in improvement in motor milestones according to Section 2 of the Hammersmith Infant Neurologic Exam (HINE).

8. The method of claim 7, wherein the method results in at least a 2-point increase in ability to kick in accordance with Section 2 of HINE.

9. The method of claim 7, wherein the method results in at least a 1-point increase in the motor milestones of head control, rolling, sitting, crawling, standing, voluntary grasp, or walking in accordance with section 2 of HINE.

10. The method of claim 1, wherein the method results in improvement in motor function according to the Children's Hospital of Philadelphia Infant Test of Neuromuscular Disorders (CHOP Intend).

11. The method of claim 10, wherein the method results in at least a 4-point increase in motor function in accordance with CHOP Intend.

12. The method of claim 1, wherein the method further comprises administration of an additional active agent or supportive therapy for treating SMA.

13. The method of claim 12, wherein the additional active agent is nusinersen.

14. The method of claim 12, wherein the additional active agent or supportive therapy is selected from the group consisting of: SMN1 gene replacement, SMN2 alternative splicing modulation, SMN2 gene activation, a histone deacetylase inhibitor, benzamide M344, a hydroxamic acid, prolactin, a natural polyphenol compound, a p38 pathway activator, SMN stabilization, neuroprotection, thyrotropin-releasing hormone, riluzole, a beta-lactam antibiotic, and muscle restoration.

15. The method of claim 1, wherein the ActRIIB extracellular domain polypeptide does not comprise an acidic amino acid at the position corresponding to L79 of SEQ ID NO: 1.

16. The method of claim 1, wherein the ALK4-Fc fusion protein further comprises a linker domain positioned between the ALK4 domain and the Fc domain and/or the ActRIIB fusion protein further comprises a linker domain positioned between the ActRIIB domain and the Fc domain.

17. The method of claim 16, wherein the linker domain is selected from: TGGG (SEQ ID NO: 17), TGGGG (SEQ ID NO: 15), SGGGG (SEQ ID NO: 16), GGGGS (SEQ ID NO: 58), GGG (SEQ ID NO: 13), GGGG (SEQ ID NO: 14), SGGG (SEQ ID NO: 18), and GGGGS (SEQ ID NO: 58).

18. The method of claim 1, wherein the ALK4-Fc fusion protein comprises an amino acid sequence selected from:

a. an amino acid sequence that is at least 95% identical to SEQ ID NO: 44;

b. an amino acid sequence that is at least 95% identical to SEQ ID NO: 48; and c. an amino acid sequence that is at least 95% identical to SEQ ID NO: 76.

19. The method of claim 1, wherein the ActRIIB-Fc fusion protein comprises an amino acid sequence selected from:

a. an amino acid sequence that is at least 95% identical to SEQ ID NO: 41;

b. an amino acid sequence that is at least 95% identical to SEQ ID NO: 46;

c. an amino acid sequence that is at least 95% identical to SEQ ID NO: 72; and d. an amino acid sequence that is at least 95% identical to SEQ ID NO: 80.

20. The method of claim 1, wherein the ALK4-Fc fusion protein comprises an amino acid sequence that is at least 90% identical to SEQ ID NO: 44 and the ActRIIB-Fc fusion protein comprises an amino acid sequence that is at least 90% identical to SEQ ID NO: 41.

21. The method of claim 1, wherein the ALK4-Fc fusion protein comprises an amino acid sequence that is identical to SEQ ID NO: 44 and the ActRIIB-Fc fusion protein comprises an amino acid sequence that is identical to SEQ ID NO: 41.

22. The method of claim 1, wherein the ALK4-Fc fusion protein comprises an amino acid sequence that is at least 90% identical to SEQ ID NO: 48 and the ActRIIB-Fc fusion protein comprises an amino acid sequence that is at least 90% identical to SEQ ID NO: 46.

23. The method of claim 1, wherein the ALK4-Fc fusion protein comprises an amino acid sequence that is identical to SEQ ID NO: 48 and the ActRIIB-Fc fusion protein comprises an amino acid sequence that is identical to SEQ ID NO: 46.

24. The method of claim 1, wherein the ALK4-Fc fusion protein comprises an amino acid sequence that is at least 90% identical to SEQ ID NO: 76 and the ActRIIB-Fc fusion protein comprises an amino acid sequence that is at least 90% identical to SEQ ID NO: 72.

25. The method of claim 1, wherein the ALK4-Fc fusion protein comprises an amino acid sequence that is identical to SEQ ID NO: 76 and the ActRIIB-Fc fusion protein comprises an amino acid sequence that is identical to SEQ ID NO: 72.

26. The method of claim 1, wherein the ALK4-Fc fusion protein comprises an amino acid sequence that is at least 90% identical to SEQ ID NO: 48 and the ActRIIB-Fc fusion protein comprises an amino acid sequence that is at least 90% identical to SEQ ID NO: 80.

27. The method of claim 1, wherein the ALK4-Fc fusion protein comprises an amino acid sequence that is identical to SEQ ID NO: 48 and the ActRIIB-Fc fusion protein comprises an amino acid sequence that is identical to SEQ ID NO: 80.

28. The method of claim 2, wherein the areflexia is in the extremities.

29. The method of claim 2, wherein the loss of strength of respiratory muscles results in weak cough, weak cry, accumulation of secretions in lungs or throat, or respiratory distress.

30. The method of claim 2, wherein the difficulty in sucking or swallowing results in poor feeding.

* * * * *